United States Patent
Yuen

(10) Patent No.: US 7,485,636 B2
(45) Date of Patent: Feb. 3, 2009

(54) THERAPEUTIC PYRAZOLO[3,4-B]PYRIDINES AND INDAZOLES

(75) Inventor: Po-Wai Yuen, Ann Arbor, MI (US)

(73) Assignee: Pfizer Inc., New York, NY (US)

( * ) Notice: Subject to any disclaimer, the term of this patent is extended or adjusted under 35 U.S.C. 154(b) by 142 days.

(21) Appl. No.: 11/446,277

(22) Filed: Jun. 2, 2006

(65) Prior Publication Data

US 2006/0217376 A1    Sep. 28, 2006

Related U.S. Application Data

(63) Continuation of application No. 11/287,759, filed on Nov. 28, 2005, now Pat. No. 7,423,054.

(60) Provisional application No. 60/631,386, filed on Nov. 29, 2004.

(51) Int. Cl.
A61K 31/535    (2006.01)
C07D 413/12    (2006.01)

(52) U.S. Cl. ................... 514/234.5; 544/140
(58) Field of Classification Search ............ 544/140; 514/234.5
See application file for complete search history.

(56) References Cited

U.S. PATENT DOCUMENTS

| | | |
|---|---|---|
| 3,428,634 A | 2/1969 | Palazzo |
| 3,488,353 A | 1/1970 | Archer |
| 3,678,059 A | 7/1972 | Gschwend et al. |
| 3,681,382 A | 8/1972 | Gschwend |
| 4,474,964 A | 10/1984 | Ibuki et al. |
| 4,549,023 A | 10/1985 | Ibuki et al. |
| 4,585,869 A | 4/1986 | Ibuki et al. |
| 4,670,447 A | 6/1987 | Strupczewski |
| 4,710,573 A | 12/1987 | Strupczewski |
| 4,758,668 A | 7/1988 | Strupczewski |
| 4,775,761 A | 10/1988 | Strupczewski |
| 4,806,649 A | 2/1989 | Strupczewski |
| 4,853,470 A | 8/1989 | Strupczewski |
| 4,933,460 A | 6/1990 | Strupczewski |
| 4,954,503 A | 9/1990 | Strupczewski et al. |
| 4,957,916 A | 9/1990 | Kennis et al. |
| 4,999,356 A | 3/1991 | Strupczewski et al. |
| 5,015,740 A | 5/1991 | Kennis et al. |
| 5,077,405 A | 12/1991 | Strupczewski et al. |
| 5,134,236 A | 7/1992 | Strupczewski et al. |
| 5,348,968 A | 9/1994 | Lavielle et al. |
| 5,494,908 A | 2/1996 | O'Malley et al. |
| 5,538,984 A | 7/1996 | Villalobos et al. |
| 5,580,982 A | 12/1996 | O'Malley et al. |
| 5,681,954 A | 10/1997 | Yamamoto et al. |
| 5,750,542 A | 5/1998 | Villalobos et al. |
| 5,756,754 A | 5/1998 | O'Malley et al. |
| 5,780,475 A | 7/1998 | Baker et al. |
| 5,854,247 A | 12/1998 | Baker et al. |
| 5,925,766 A | 7/1999 | O'Malley et al. |
| 5,965,582 A | 10/1999 | Lebaut et al. |
| 5,973,156 A | 10/1999 | Chambers et al. |
| 5,977,116 A | 11/1999 | Castro Pineiro et al. |
| 5,998,415 A | 12/1999 | Chambers et al. |
| 6,046,203 A | 4/2000 | O'Malley et al. |
| 6,054,456 A | 4/2000 | Ladduwahetty et al. |
| 6,166,023 A | 12/2000 | Schindler et al. |
| 6,166,027 A | 12/2000 | Straub et al. |
| 6,326,382 B1 | 12/2001 | Villalobos et al. |
| 6,329,412 B1 | 12/2001 | Goldstein et al. |
| 6,387,940 B1 | 5/2002 | Straub et al. |
| 6,391,872 B1 | 5/2002 | Marfat |
| 6,410,740 B1 | 6/2002 | Straub et al. |
| 6,414,009 B1 | 7/2002 | Straub et al. |
| 6,451,805 B1 | 9/2002 | Straub et al. |
| 6,462,068 B1 | 10/2002 | Straub et al. |
| 6,465,467 B1 | 10/2002 | Nilsson et al. |
| 6,498,255 B2 | 12/2002 | Villalobos et al. |
| 6,541,484 B2 | 4/2003 | Collins et al. |

(Continued)

FOREIGN PATENT DOCUMENTS

DE    3338903    5/1985

(Continued)

OTHER PUBLICATIONS

FDA mulls drug to slow late-stage Alzheimer's [online], [retrieved on Sep. 23, 2003]. Retrieved from the internet, URL <http://www.cnn.com/2003/HEALTH/conditions/09/24/alzheimers.drug.ap/index.html>.*

(Continued)

*Primary Examiner*—Rebecca L Anderson
(74) *Attorney, Agent, or Firm*—Gregg C. Benson; James T. Jones

(57) ABSTRACT

The present invention provides for compounds of Formula I:

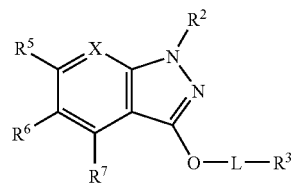

Figure 1:
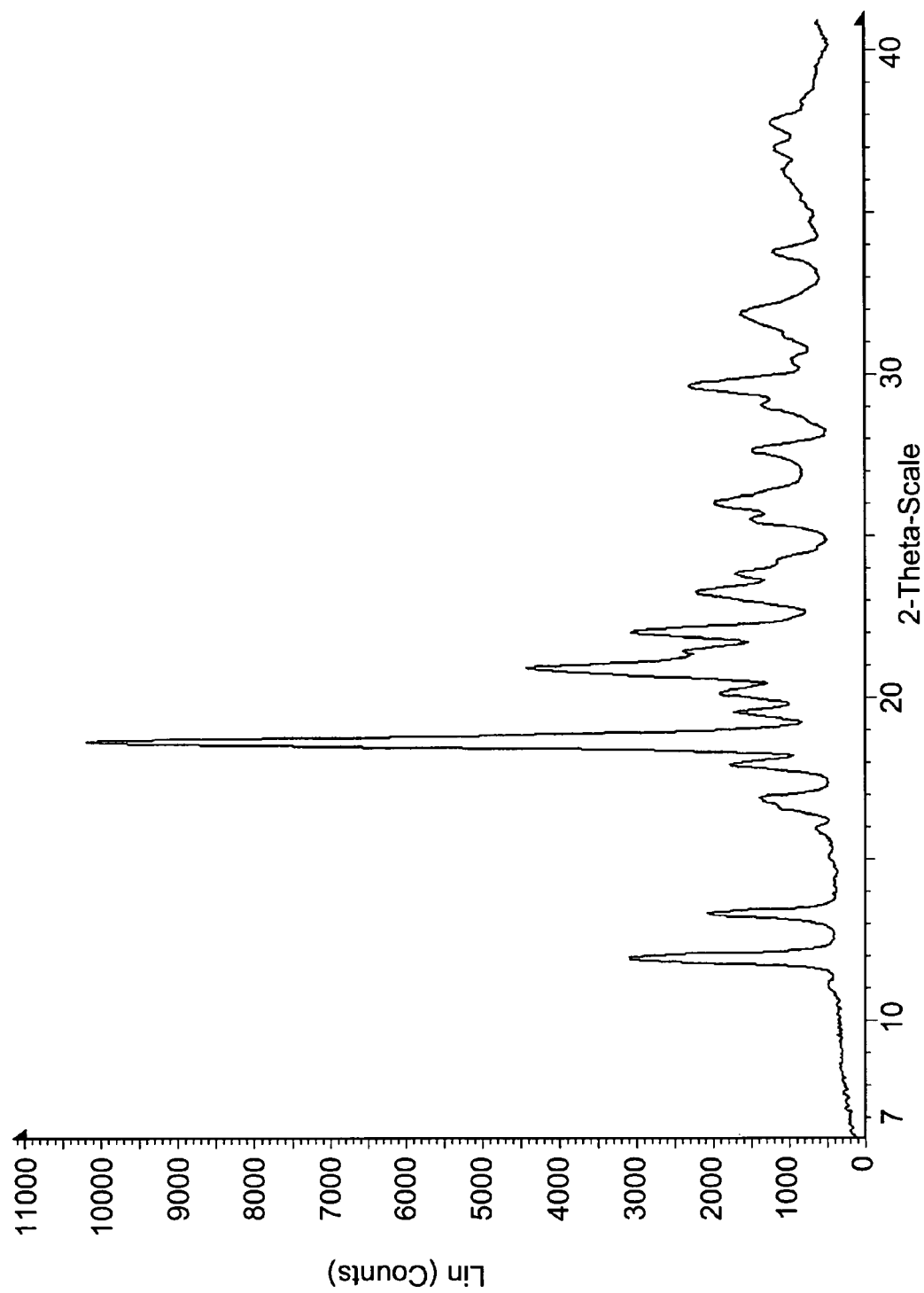
Figure 2:
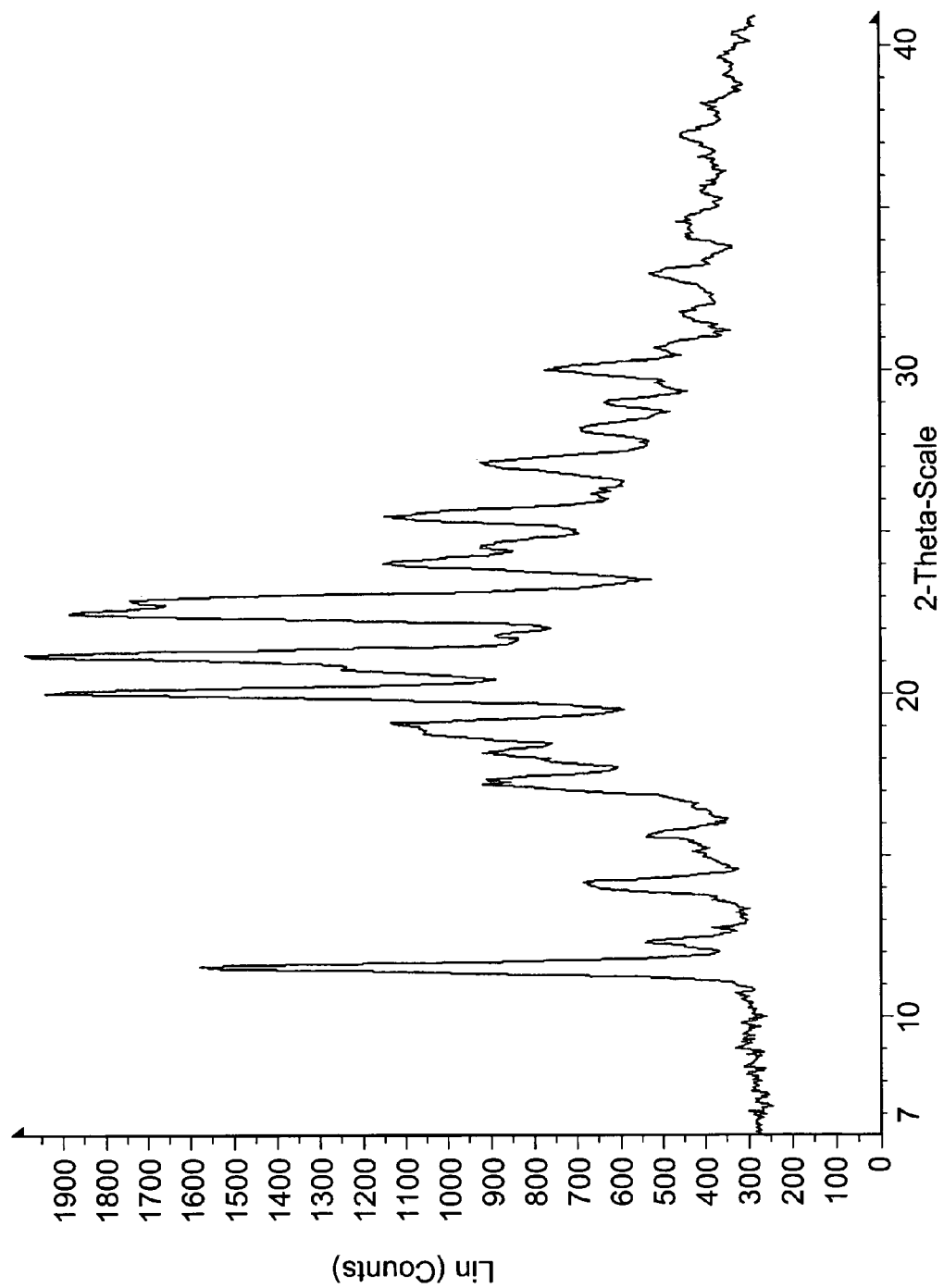
Figure 3:
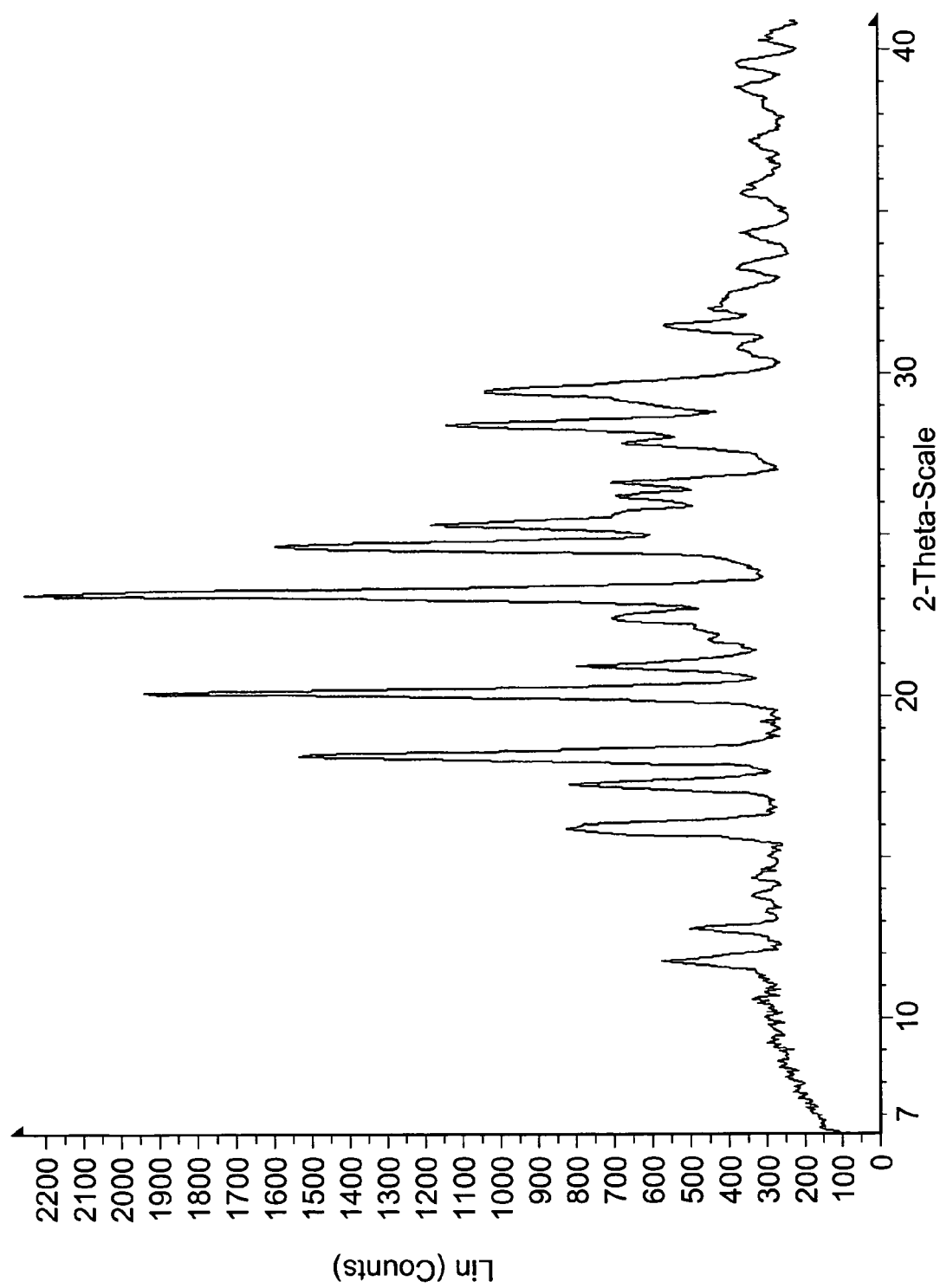
Figure 4:
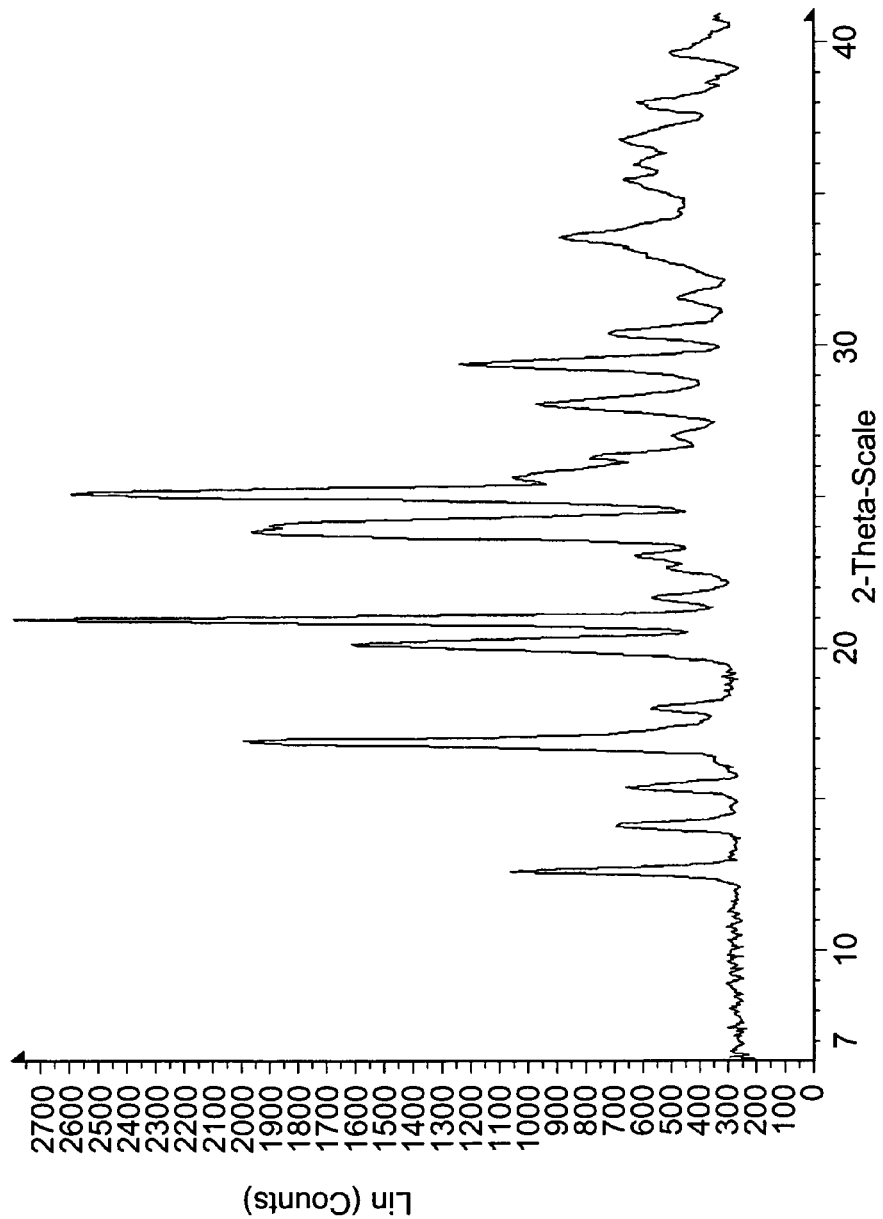
Figure 5:
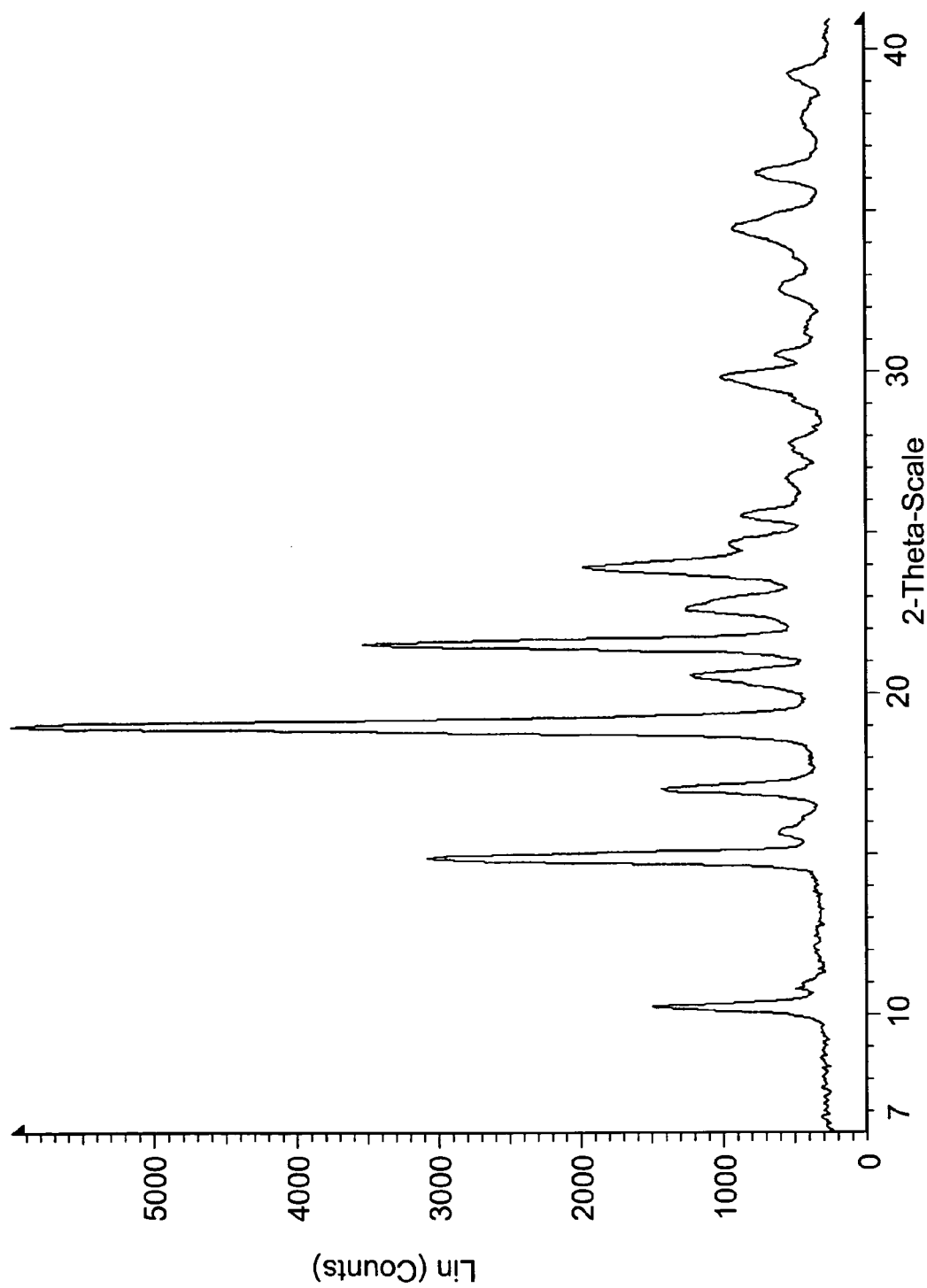
Figure 6:
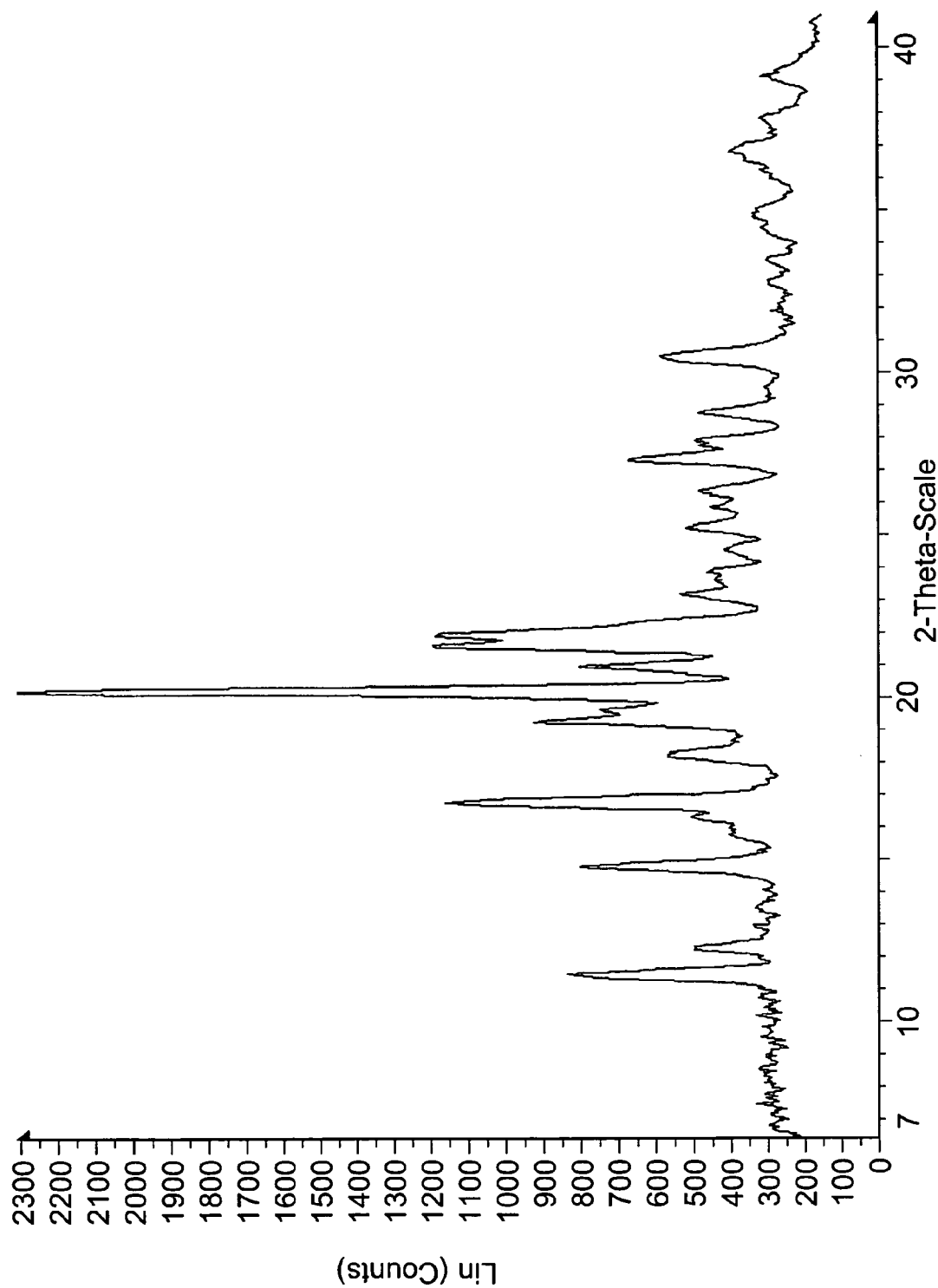
Figure 7:
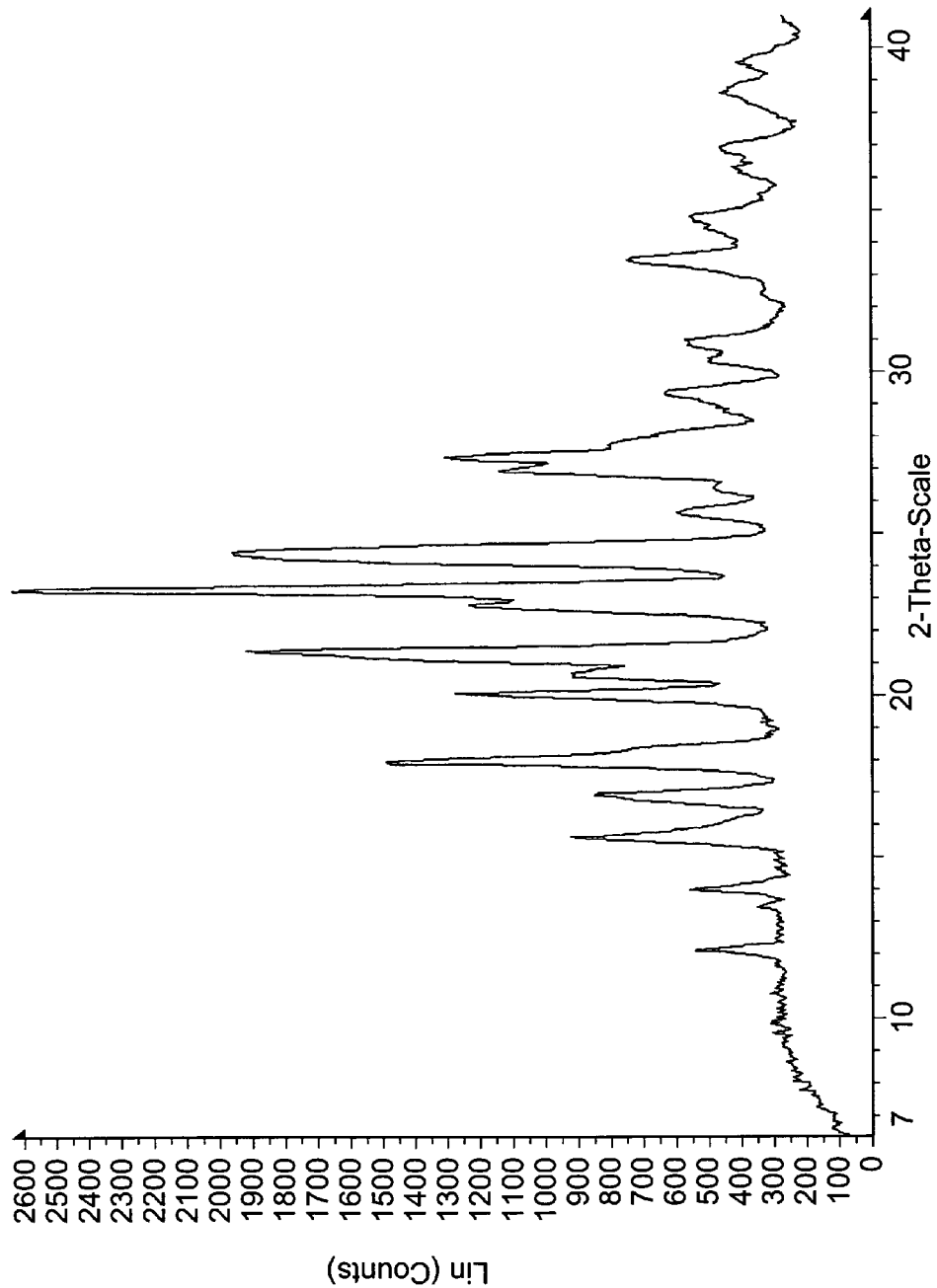

wherein $R^2$, $R^3$, $R^4$, $R^5$, $R^6$, $R^7$, X, and L have any of the values defined in the specification, and pharmaceutically acceptable salts thereof, that are useful as agents in the treatment of central nervous disorders and conditions including attention deficit hyperactivity disorder, neuropathic pain, urinary incontinence, anxiety, depression, and schizophrenia and fibromyalgia. Also provided are pharmaceutical compositions comprising one or more compounds of Formula I.

12 Claims, 17 Drawing Sheets

U.S. PATENT DOCUMENTS

| | | |
|---|---|---|
| 6,552,192 B1 | 4/2003 | Hanus et al. |
| 6,743,798 B1 | 6/2004 | Straub et al. |
| 2002/0028834 A1 | 3/2002 | Villalobos et al. |
| 2002/0052373 A1 | 5/2002 | Zom et al. |
| 2002/0198213 A1 | 12/2002 | Zhou et al. |
| 2003/0073849 A1 | 4/2003 | Mattson et al. |
| 2003/0092694 A1 | 5/2003 | Nilsson et al. |
| 2003/0176421 A1 | 9/2003 | Watson et al. |
| 2003/0191086 A1 | 10/2003 | Hanus et al. |
| 2004/0063713 A1 | 4/2004 | Cowart et al. |
| 2004/0186148 A1 | 9/2004 | Shankar et al. |
| 2004/0224945 A1 | 11/2004 | Straub et al. |
| 2004/0236101 A1 | 11/2004 | Makriyannis et al. |
| 2004/0242554 A1 | 12/2004 | Nilsson et al. |
| 2006/0019967 A1 | 1/2006 | Wu et al. |

FOREIGN PATENT DOCUMENTS

| | | |
|---|---|---|
| EP | 0 135 781 | 10/1989 |
| EP | 0 562 832 A1 | 3/1993 |
| EP | 1 040 829 A2 | 12/1999 |
| FR | 2 034 495 | 1/1970 |
| JP | 58-159469 | 9/1983 |
| JP | 3-223265 | 10/1991 |
| JP | 11-279156 | 10/1999 |
| JP | 2003-146879 | 5/2003 |
| JP | 2003-146973 | 5/2003 |
| WO | WO 98/01428 | 1/1998 |
| WO | WO 99/58503 | 11/1999 |
| WO | WO 00/06559 | 2/2000 |
| WO | WO 00/27394 | 5/2000 |
| WO | WO 00/43394 | 7/2000 |
| WO | WO 00/76984 | 12/2000 |
| WO | WO 01/44244 | 6/2001 |
| WO | WO 01/57024 | 8/2001 |
| WO | WO 01/70701 A1 | 9/2001 |
| WO | WO 01/70702 A1 | 9/2001 |
| WO | WO 03/076408 | 9/2003 |
| WO | WO 03/101994 | 12/2003 |
| WO | WO 2004/085385 | 10/2004 |

OTHER PUBLICATIONS

Cecil Textbook of Medicine, 20th edition (1996), vol. 2, pp. 1992-1996.*

Baiocchi et al., "Synthesis, Properties, and Reactions of 1H-Indazol-3-ols and 1,2-Dihydro-3H-indazol-3-ones", Synthesis, Sep. 1976, pp. 633-648.

Palazzo et al., "Synthesis and Pharmacological Properties of 1-Substituted 3-Dimethylaminoalkoxy-1H-Indazoles", J. Med. Chem., Jan. 1986, vol. 9, pp. 38-41.

Selwood et al., "Synthesis and Biological Evaluation of Novel Pyrazoles and Indazoles as Activators of the Nitric Oxide Receptor, Soluble Guanylate Cyclase", J. Med. Chem., 2001, vol. 44, pp. 78-93.

Sluka, "Stimulation of Deep Somatic Tissue with Capsaicin Produces Long-Lasting Mechanical Allodynia and Heat Hypoalgesia that Depends on Early Activation of the cAMP Pathway", J. Neurosci., Jul. 2002, vol. 22, No. 13, pp. 5687-5693.

PCT International Search Report for PCT/IB2005/003549 mailed Oct. 19, 2006.

* cited by examiner

THERAPEUTIC PYRAZOLO[3,4-B]PYRIDINES AND INDAZOLES

CROSS-REFERENCE TO RELATED APPLICATIONS

This application is a continuation of U.S. Ser. No. 11/287,759, filed Nov. 28, 2005, now U.S. Pat. No. 7,423,054, and claims the benefit of U.S. Provisional Patent application Ser. No. 60/631,386, filed on Nov. 29, 2004, the teachings of each of which are herein incorporated by reference.

BACKGROUND OF THE INVENTION

The monoamines norepinephrine and serotonin have a variety of effects as neurotransmitters. These monoamines are taken up by neurons after being released into the synaptic cleft. Norepinephrine and serotonin are taken up from the synaptic cleft by their respective norepinephrine and serotonin transporters.

Drugs that inhibit the norepinephrine and serotonin transporters can prolong the effects of norepinephrine and serotonin, respectively, in the synapse, providing treatment for a number of diseases. For example, the serotonin reuptake inhibitor fluoxetine has been found to be useful in the treatment of depression and other nervous system disorders. The norepinephrine reuptake inhibitor atomoxetine has been approved for the treatment of attention deficit hyperactivity disorder (ADHD) as STRATTERA®. In addition, the norepinephrine and serotonin transporter inhibitor milnacipran is being developed for the treatment of fibromyalgia, a disease that affects about 2% of the adult population in the United States. However, the FDA has not currently approved any drug for the treatment of fibromyalgia. Accordingly, there is an ongoing need in the art for compounds that are norepinephrine transporter inhibitors, serotonin transporter inhibitors, and that inhibit both norepinephrine and serotonin transporters, for the treatment of diseases including fibromyalgia, ADHD, neuropathic pain, urinary incontinence, generalized anxiety disorder, depression, and schizophrenia.

SUMMARY OF THE INVENTION

In one aspect, the present invention provides for compounds of formula I:

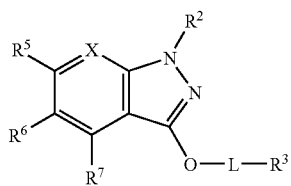

I or a pharmaceutically acceptable salt thereof; wherein: X is N or $C(R^4)$; $R^2$ is 2-pyridinyl or phenyl, wherein said 2-pyridinyl or said phenyl may be optionally substituted with one to three substituents independently selected from the group consisting of: hydrogen, halo, methyl, ethyl, $CF_3$, methoxy, $CH_2F$, $CHF_2$, and $CH_2OH$; L is absent or methylene; $R^3$ is selected from the group consisting of: 3-pyrrolidinyl, 4-piperidinyl, 3-piperidinyl, and 2-morpholinyl; and $R^4$, $R^5$, $R^6$, and $R^7$ are H; or three of $R^4$, $R^5$, $R^6$, and $R^7$ are H and one $R^4$, $R^5$, $R^6$, and $R^7$ is selected from the group consisting of: halo, methoxy, and a $C_1$-$C_3$ alkyl. Examples of a $R^2$ phenyl group substituted with one to three substituents independently selected from the group consisting of: hydrogen, halo, methyl, ethyl, $CF_3$, methoxy, $CH_2F$, $CHF_2$, and $CH_2OH$ include, but are not limited to, 3-chlorophenyl, 2,6-dibromophenyl, 2,4,6-tribromophenyl, 2,6-dichlorophenyl, 4-trifluoromethylphenyl, 3-methyl-phenyl, 4-methyl-phenyl, 3,5-dimethyl-phenyl, 3,4,5-trimethoxy-phenyl, 3,5-dimethoxy-phenyl, 3,4-dimethoxy-phenyl, 3-methoxy-phenyl, 4-methoxy-phenyl, 3,5-difluoro-phenyl, 4-chloro-phenyl, 3-trifluoromethyl-phenyl, 3,5-dichloro-phenyl, 2-methoxy-5-methyl-phenyl, 2-fluoro-5-methyl-phenyl, 4-chloro-2-trifluoromethyl-phenyl, and the like.

In certain embodiments of Formula I, X is $C(R^4)$, $R^2$ is phenyl, and $R^4$, $R^5$, $R^6$, and $R^7$ are H; or three of $R^4$, $R^5$, $R^6$, and $R^7$ are H and one of $R^4$, $R^5$, $R^6$, and $R^7$ is selected from the group consisting of: halo, methoxy, and a $C_1$-$C_3$ alkyl.—a compound of Formula II. In certain embodiments of Formula II, $R^4$, $R^5$, $R^6$, and $R^7$ are H, and $R^2$ is optionally substituted with one or two substituents independently selected from the group consisting of: hydrogen and fluoro. In certain embodiments of Formula II, $R^3$ is a 3-pyrrolidinyl. Examples of compounds of Formula II where $R^3$ is a 3-pyrrolidinyl include: (R)-1-(2,5-difluoro-phenyl)-3-(pyrrolidin-3-ylmethoxy)-1H-indazole; (R)-1-(2,4-difluoro-phenyl)-3-(pyrrolidin-3-ylmethoxy)-1H-indazole; (S)-1-(2,4-difluoro-phenyl)-3-(pyrrolidin-3-ylmethoxy)-1H-indazole; (S)-(−)-1-(2-fluorophenyl)-3-(pyrrolidin-3-ylmethoxy)-1H-indazole; (S)-1-(2,6-difluoro-phenyl)-3-(pyrrolidin-3-ylmethoxy)-1H-indazole; (R)-1-phenyl-3-(pyrrolidin-3-ylmethoxy)-1H-indazole; and (S)-(−)-1-(2-fluorophenyl)-3-(pyrrolidin-2-yloxy)-1H-indazole. In certain embodiments of Formula II, $R^3$ is a 3- or 4-piperidinyl. Examples of compounds of Formula II where $R^3$ is a 3- or 4-piperidinyl include include: (±)-1-(2,5-difluoro-phenyl)-3-(piperidin-3-ylmethoxy)-1H-indazole; 1-(3-fluoro-phenyl)-3-(piperidin-4-yloxy)-1H-indazole; 1-phenyl-3-(piperidin-4-yloxy)-1H-indazole; 1-(2,6-difluoro-phenyl)-3-(piperidin-4-yloxy)-1H-indazole; 1-(2,5-difluoro-phenyl)-3-(piperidin-4-yloxy)-1H-indazole; and (±)-1-(3-fluoro-phenyl)-3-(piperidin-3-ylmethoxy)-1H-indazole. Additional compounds of Formula II where $R^3$ is a 3- or 4-piperidinyl include: (S)-(−)-1-(2-fluorophenyl)-3-(piperidin-3-ylmethoxy)-1H-indazole; (S)-1-(2,6-difluoro-phenyl)-3-(piperidin-3-ylmethoxy)-1H-indazole; and (S)-(−)-1-phenyl-3-(piperidin-3-ylmethoxy)-1H-indazole. In certain embodiments of Formula II, $R^3$ is a 2-morpholinyl. Examples of compounds of Formula II where $R^3$ is a 2-morpholinyl include: (S)-(+)-1-(2,5-difluorophenyl)-3-(morpholin-2-ylmethoxy)-1H-indazole; (S)-1-(2,6-difluoro-phenyl)-3-(morpholin-2-ylmethoxy)-1H-indazole; (S)-(+)-1-(2,4-difluorophenyl)-3-(morpholin-2-ylmethoxy)-1H-indazole; (S)-1-(3,4-difluoro-phenyl)-3-(morpholin-2-ylmethoxy)-1H-indazole; (S)-(+)-1-(2-fluorophenyl)-3-(morpholin-2-ylmethoxy)-1H-indazole; and (S)-(+)-3-(morpholin-2-ylmethoxy)-1-phenyl-1H-indazole. In certain embodiments, a compound of formula I is (S)-1-(2,6-difluorophenyl)-3-(morpholin-2-ylmethoxy)-1H-indazole, or a pharmaceutically acceptable salt thereof.

In certain embodiments, the present invention provides for 1-(2-fluorophenyl)-3-(piperidin-4-yloxy)-1H-indazole, or a pharmaceutically acceptable salt thereof. In another embodiment, the present invention provides for 1-(2-fluorophenyl)-3-(piperidin-4-yloxy)-1H-indazole L-tartrate.

In certain embodiments of Formula I, X is $C(R^4)$, $R^2$ is phenyl, and $R^6$ is selected from the group consisting of: halo, methoxy, and a $C_1$-$C_3$ alkyl—a compound of Formula III. In certain embodiments of Formula III, R² is optionally substituted with one or two substituents independently selected from the group consisting of: hydrogen and fluoro. In certain embodiments of Formula III, R³ is a 3-pyrrolidinyl. An example of a compound of Formula III where R³ is a 3-pyrrolidinyl is (R)-1-(2,5-difluoro-phenyl)-5-fluoro-3-(pyrrolidin-3-ylmethoxy)-1H-indazole. In certain embodiments of Formula III, R³ is a 4-piperidinyl or 3-piperidinyl. An example of a compounds of Formula III where R³ is a 4-piperidinyl or 3-piperidinyl is 1-(2,6-difluoro-phenyl)-5-fluoro-3-(piperidin-4-yloxy)-1H-indazole. In certain embodiments of Formula III, R³ is a 2-morpholinyl. Examples of compounds of Formula II where R³ is a 2-morpholinyl include: (S)-1-(2,6-difluoro-phenyl)-5-fluoro-3-(morpholin-2-yl-methoxy)-1H-indazole; (S)-1-(2,5-difluoro-phenyl)-5-fluoro-3-(morpholin-2-ylmethoxy)-1H-indazole; and (S)-(+)-5-fluoro-1-(2-fluorophenyl)-3-(morpholin-2-ylmethoxy)-1H-indazole. In certain embodiments, a compound of formula I is (S)-1-(2,5-difluoro-phenyl)-5-fluoro-3-(morpholin-2-ylmethoxy)-1H-indazole, or a pharmaceutically acceptable salt thereof. In certain embodiments, a compound of formula I is (S)-(+)-1-(2,4-difluorophenyl)-5-fluoro-3-(morpholin-2-ylmethoxy)-1H-indazole, or a pharmaceutically acceptable salt thereof.

In certain embodiments of Formula I, X is C(R⁴), R² is phenyl, and R⁷ is selected from the group consisting of: halo, methoxy, and a $C_1$-$C_3$ alkyl—a compound of Formula IV. In certain embodiments of Formula IV, R² is optionally substituted with one or two substituents independently selected from the group consisting of: hydrogen and fluoro. In certain embodiments of Formula IV, R³ is a 3-pyrrolidinyl. In certain embodiments of Formula IV, R³ is a 3- or 4-piperidinyl. Examples of compounds of Formula IV where R³ is a 3- or 4-piperidinyl include include: 4-fluoro-1-(2-fluoro-phenyl)-3-(piperidin-4-yloxy)-1H-indazole; 1-(2,5-difluoro-phenyl)-4-fluoro-3-(piperidin-4-yloxy)-1H-indazole; 1-(2,4-difluoro-phenyl)-4-fluoro-3-(piperidin-4-yloxy)-1H-indazole; (S)-1-(2,5-difluoro-phenyl)-4-fluoro-3-(piperidin-3-yl-methoxy)-1H-indazole; and (S)-4-fluoro-1-(2-fluoro-phenyl)-3-(piperidin-3-ylmethoxy)-1H-indazole. In certain embodiments of Formula IV, R³ is a 2-morpholinyl. An example of a compound of Formula IV where R³ is a 2-morpholinyl is (S)-1-(2,5-difluoro-phenyl)-4-fluoro-3-(morpholin-2-ylmethoxy)-1H-indazole.

In certain embodiments of Formula I, X is C(R⁴), R² is phenyl, and R⁵ is selected from the group consisting of: halo, methoxy, and a $C_1$-$C_3$ alkyl—a compound of Formula V. In certain embodiments of Formula I, X is C(R⁴), R² is phenyl, and R⁴ is selected from the group consisting of: halo, methoxy, and a $C_1$-$C_3$ alkyl—a compound of Formula VI. In certain embodiments of Formula I, X is C(R⁴), and R² is 2-pyridinyl—a compound of Formula VII. In certain embodiments of Formula I, X is N, and R² is phenyl—a compound of Formula VIII. In certain embodiments of Formula I, X is N, and R² is 2-pyridinyl—a compound of Formula IX. In certain embodiments of Formula I, X is C(R⁴), R² is phenyl optionally substituted with one or two substituents independently selected from the group consisting of: hydrogen and fluoro (e.g., 2,6-difluoro-phenyl, 2-fluoro-phenyl, 4-fluoro-phenyl, 2,4-difluoro-phenyl, 2,5-difluoro-phenyl, or 3,4-difluoro-phenyl).

In certain embodiments of Formula I, X is C(R⁴), R² is phenyl optionally substituted with one or two substituents independently selected from the group consisting of: hydrogen and fluoro, and -L-R³ is:

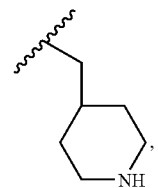

where the wavy line indicates the attachment point to the rest of the compound.

In certain embodiments of Formula I, X is C(R⁴), R² is phenyl optionally substituted with one or two substituents independently selected from the group consisting of: hydrogen and fluoro, and -L-R³ is:

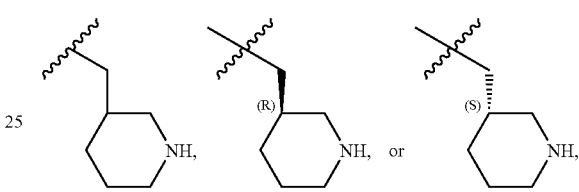

where the wavy line indicates the attachment point to the rest of the compound.

In certain embodiments of Formula I, X is C(R⁴), R² is phenyl optionally substituted with one or two substituents independently selected from the group consisting of: hydrogen and fluoro, and -L-R³ is:

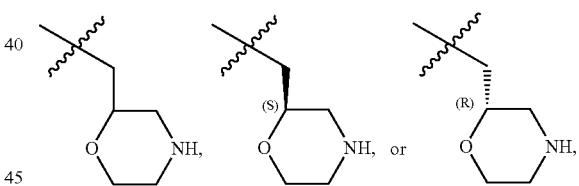

where the wavy line indicates the attachment point to the rest of the compound. In certain embodiments, -L-R³ is

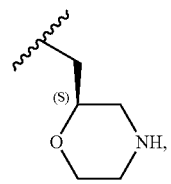

where the wavy line indicates the attachment point to the rest of the compound.

In certain embodiments of Formula I, X is C(R⁴), R² is phenyl optionally substituted with one or two substituents independently selected from the group consisting of: hydrogen and fluoro, and -L-R³ is:

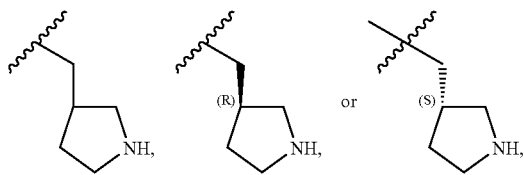

where the wavy line indicates the attachment point to the rest of the compound.

In another aspect, the present invention provides for compounds of formula XI:

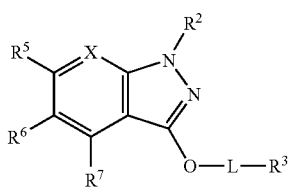

XI or a pharmaceutically acceptable salt thereof; wherein: X is N or C(R$^4$); R$^2$ is 2-pyridinyl or phenyl, wherein said 2-pyridinyl or said phenyl may be optionally substituted with one to three substituents independently selected from the group consisting of: hydrogen, halo, methyl, ethyl, CF$_3$, methoxy, CH$_2$F, CHF$_2$, and CH$_2$OH; L is absent or methylene; R$^4$, R$^5$, R$^6$, and R$^7$ are H; or three of R$^4$, R$^5$, R$^6$, and R$^7$ are H and one of R$^4$, R$^5$, R$^6$, and R$^7$ is selected from the group consisting of: halo, methoxy, and a C$_1$-C$_3$ alkyl; R$^3$ is selected from the group consisting of: 3-pyrrolidinyl, 4-piperidinyl, 3-piperidinyl, and 2-morpholinyl, wherein the nitrogen in the ring of said 3-pyrrolidinyl, 4-piperidinyl, 3-piperidinyl, or 2-morpholinyl is substituted with a C$_1$-C$_3$ alkyl or a —C(O)—O—C$_1$-C$_4$alkyl. In certain embodiments, a compound of formula XI may be deprotected by removing said C$_1$-C$_3$ alkyl or —C(O)—O—C$_1$-C$_4$alkyl from the nitrogen in the ring of said 3-pyrrolidinyl, 4-piperidinyl, 3-piperidinyl, or 2-morpholinyl using suitable reagents and conditions to form a compound of formula I.

In another aspect, the present invention provides for methods of treating a mammal suffering from a norepinephrine-mediated and/or serotonin-mediated disorder comprising administering to a mammal in need of such treatment a therapeutically effective amount of a compound of formula I.

In another aspect, the present invention provides for methods of treating attention deficit hyperactivity disorder (ADHD) comprising administering to a mammal in need of such treatment a therapeutically effective amount of a compound of formula I.

In another aspect, the present invention provides for methods of treating a disorder or condition selected from neuropathic pain, stress urinary incontinence, depression, and schizophrenia, comprising administering to a mammal in need of such treatment a therapeutically effective amount of a compound of formula I.

In another aspect, the present invention provides for methods of treating fibromyalgia comprising administering to a mammal in need of such treatment a therapeutically effective amount of a compound of formula I. In certain embodiments, the present invention provides for methods of treating fibromyalgia comprising administering to a mammal in need of such treatment a therapeutically effective amount of 1-(2-fluorophenyl)-3-(piperidin-4-yloxy)-1H-indazole, or a pharmaceutically acceptable salt therof. In certain embodiments, the present invention provides for methods of treating fibromyalgia comprising administering to a mammal in need of such treatment a therapeutically effective amount of 1-(2-fluorophenyl)-3-(piperidin-4-yloxy)-1H-indazole L-tartrate.

In another aspect, the present invention provides for methods of treating a mammal suffering from a norepinephrine-mediated and/or serotonin-mediated disorder comprising administering to a mammal in need of such treatment: (a) a compound of the formula I or a pharmaceutically acceptable salt thereof; (b) another pharmaceutically active compound that is an antidepressant or anti-anxiety agent, or a pharmaceutically acceptable salt thereof; and (c) a pharmaceutically acceptable carrier; wherein the active compounds "a" and "b" are present in amounts that render the composition effective in treating such disorder or condition.

In another aspect, the present invention provides for pharmaceutical compositions comprising: a therapeutically effective amount of a compound of formula I and a pharmaceutically acceptable carrier. In certain embodiments, these compositions are useful in the treatment of a norepinephrine-mediated and/or serotonin-mediated disorder.

In another aspect, the present invention provides for crystalline 1-(2-fluorophenyl)-3-(piperidin-4-yloxy)-1H-indazole or a pharmaceutically acceptable salt thereof. In one embodiment, the present invention provides for crystalline 1-(2-fluorophenyl)-3-(piperidin-4-yloxy)-1H-indazole L-tartrate. In certain embodiments, crystalline 1-(2-fluorophenyl)-3-(piperidin-4-yloxy)-1H-indazole L-tartrate has a X-ray powder diffraction spectrum comprising the following 2-theta values ±0.1 measured using CuKα radiation: 22.0, 20.9, and 18.6. In certain embodiments, crystalline 1-(2-fluorophenyl)-3-(piperidin-4-yloxy)-1H-indazole L-tartrate has a X-ray powder diffraction spectrum comprising the following 2-theta values ±0.1 measured using CuKα radiation: 13.2, 11.8, and 18.7.

In certain embodiments, crystalline 1-(2-fluorophenyl)-3-(piperidin-4-yloxy)-1H-indazole L-tartrate has a X-ray powder diffraction spectrum comprising the following 2-theta values ±0.1 measured using CuKα radiation: 37.8, 33.8, 16.8, 11.9, 13.2, 29.0, 19.5, 27.6, 31.9, 25.5, 17.9, 23.8, 20.1, 26.0, 23.2, 29.6, 21.4, 22.0, 20.9, and 18.6.

In certain embodiments, crystalline 1-(2-fluorophenyl)-3-(piperidin-4-yloxy)-1H-indazole edisylate has a X-ray powder diffraction spectrum comprising the following 2-theta values ±0.1 measured using CuKα radiation: 22.5, 20.0, and 21.2. In certain embodiments, crystalline 1-(2-fluorophenyl)-3-(piperidin-4-yloxy)-1H-indazole edisylate has a X-ray powder diffraction spectrum comprising the following 2-theta values ±0.1 measured using CuKα radiation: 33.0, 15.7, 12.4, 14.1, 28.2, 30.1, 17.3, 27.1, 19.0, 25.5, 24.1, 11.6, 22.5, 20.0, and 21.2.

In certain embodiments, crystalline 1-(2-fluorophenyl)-3-(piperidin-4-yloxy)-1H-indazole fumarate has a X-ray powder diffraction spectrum comprising the following 2-theta values ±0.1 measured using CuKα radiation: 24.6, 20.1, and 23.2. In certain embodiments, crystalline 1-(2-fluorophenyl)-3-(piperidin-4-yloxy)-1H-indazole fumarate has a X-ray powder diffraction spectrum comprising the following 2-theta values ±0.1 measured using CuKα radiation: 12.7, 31.5, 11.7, 27.8, 22.4, 26.6, 20.9, 17.2, 15.9, 29.5, 28.4, 25.3, 18.1, 24.6, 20.1, and 23.2.

In certain embodiments, crystalline 1-(2-fluorophenyl)-3-(piperidin-4-yloxy)-1H-indazole hydrobromide has a X-ray powder diffraction spectrum comprising the following 2-theta values ±0.1 measured using CuKα radiation: 23.8, 16.8, and 25.1. In certain embodiments, crystalline 1-(2-fluorophenyl)-3-(piperidin-4-yloxy)-1H-indazole hydrobromide has a X-ray powder diffraction spectrum comprising the following 2-theta values ±0.1 measured using CuKα radiation: 18.0, 21.6, 38.0, 15.4, 14.1, 30.4, 26.3, 33.5, 28.0, 25.6, 12.6, 29.3, 20.1, 24.0, 23.8, 16.8, 25.1, and 20.9.

In certain embodiments, crystalline 1-(2-fluorophenyl)-3-(piperidin-4-yloxy)-1H-indazole hemi L-tartrate has a X-ray powder diffraction spectrum comprising the following 2-theta values ±0.1 measured using CuKα radiation: 34.5, 36.2, and 39.2. In certain embodiments, crystalline 1-(2-fluorophenyl)-3-(piperidin-4-yloxy)-1H-indazole hemi L-tartrate has a X-ray powder diffraction spectrum comprising the following 2-theta values ±0.1 measured using CuKα radiation: 10.3, 14.9, 15.7, 17.0, 19.0, 20.5, 21.6, 22.7, 23.9, 24.7, 25.6, 27.7, 29.8, 32.6, 34.5, 36.2, and 39.2.

In certain embodiments, crystalline 1-(2-fluorophenyl)-3-(piperidin-4-yloxy)-1H-indazole L-malate has a X-ray powder diffraction spectrum comprising the following 2-theta values ±0.1 measured using CuKα radiation: 21.9, 21.5, and 20.1. In certain embodiments, crystalline 1-(2-fluorophenyl)-3-(piperidin-4-yloxy)-1H-indazole L-malate has a X-ray powder diffraction spectrum comprising the following 2-theta values ±0.1 measured using CuKα radiation: 36.8, 24.5, 26.3, 28.7, 12.2, 25.2, 23.1, 18.2, 30.4, 27.3, 14.7, 20.9, 11.4, 19.2, 16.7, 21.9, 21.5, and 20.1.

In certain embodiments, crystalline 1-(2-fluorophenyl)-3-(piperidin-4-yloxy)-1H-indazole phosphate has a X-ray powder diffraction spectrum comprising the following 2-theta values ±0.1 measured using CuKα radiation: 21.2, 24.3, and 23.2. In certain embodiments, crystalline 1-(2-fluorophenyl)-3-(piperidin-4-yloxy)-1H-indazole phosphate has a X-ray powder diffraction spectrum comprising the following 2-theta values ±0.1 measured using CuKα radiation: 12.1, 34.7, 14.0, 30.9, 25.6, 29.3, 33.4, 16.9, 20.6, 15.6, 26.9, 22.8, 20.0, 27.3, 17.9, 21.2, 24.3, and 23.2.

In certain embodiments, crystalline 1-(2-fluorophenyl)-3-(piperidin-4-yloxy)-1H-indazole sulfate has a X-ray powder diffraction spectrum comprising the following 2-theta values ±0.1 measured using CuKα radiation: 24.3, 20.2, and 12.1. In certain embodiments, crystalline 1-(2-fluorophenyl)-3-(piperidin-4-yloxy)-1H-indazole sulfate has a X-ray powder diffraction spectrum comprising the following 2-theta values ±0.1 measured using CuKα radiation: 26.7, 27.6, 17.2, 21.4, 25.4, 29.7, 16.4, 15.0, 20.0, 18.3, 23.0, 24.3, 20.2, and 12.1.

DEFINITIONS

The term "alkyl group" or "alkyl" includes straight and branched carbon chain radicals. The term "alkylene" refers to a diradical of an unsubstituted or substituted alkane. For example, a "$C_{1-6}$ alkyl" is an alkyl group having from 1 to 6 carbon atoms. Examples of $C_1$-$C_6$ straight-chain alkyl groups include, but are not limited to, methyl, ethyl, n-propyl, n-butyl, n-pentyl, and n-hexyl. Examples of branched-chain alkyl groups include, but are not limited to, isopropyl, tert-butyl, isobutyl, etc. Examples of alkylene groups include, but are not limited to, —CH$_2$—, —CH$_2$—CH$_2$—, —CH$_2$—CH (CH$_3$)—CH$_2$—, and —(CH$_2$)$_{1-3}$. Alkylene groups can be substituted with groups as set forth below for alkyl.

The term alkyl includes both "unsubstituted alkyls" and "substituted alkyls," the latter of which refers to alkyl moieties having substituents replacing a hydrogen on one or more carbons of the hydrocarbon backbone. Such substituents are independently selected from the group consisting of: halo, I, Br, Cl, F, —OH, —COOH, trifluoromethyl, —NH$_2$, —OCF$_3$, and O—C$_1$-C$_3$ alkyl.

Typical substituted alkyl groups thus are 2,3-dichloropentyl, 3-hydroxy-5-carboxyhexyl, 2-aminopropyl, pentachlorobutyl, trifluoromethyl, methoxyethyl, 3-hydroxypentyl, 4-chlorobutyl, 1,2-dimethyl-propyl, and pentafluoroethyl.

"Halo" includes fluoro, chloro, bromo, and iodo.

Some of the compounds in the present invention may exist as stereoisomers, including enantiomers, diastereomers, and geometric isomers. All of these forms, including (R), (S), epimers, diastereomers, cis, trans, syn, anti, solvates (including hydrates), tautomers, and mixtures thereof, are contemplated in the compounds of the present invention.

BRIEF DESCRIPTIONS OF THE DRAWINGS

Figure 8:
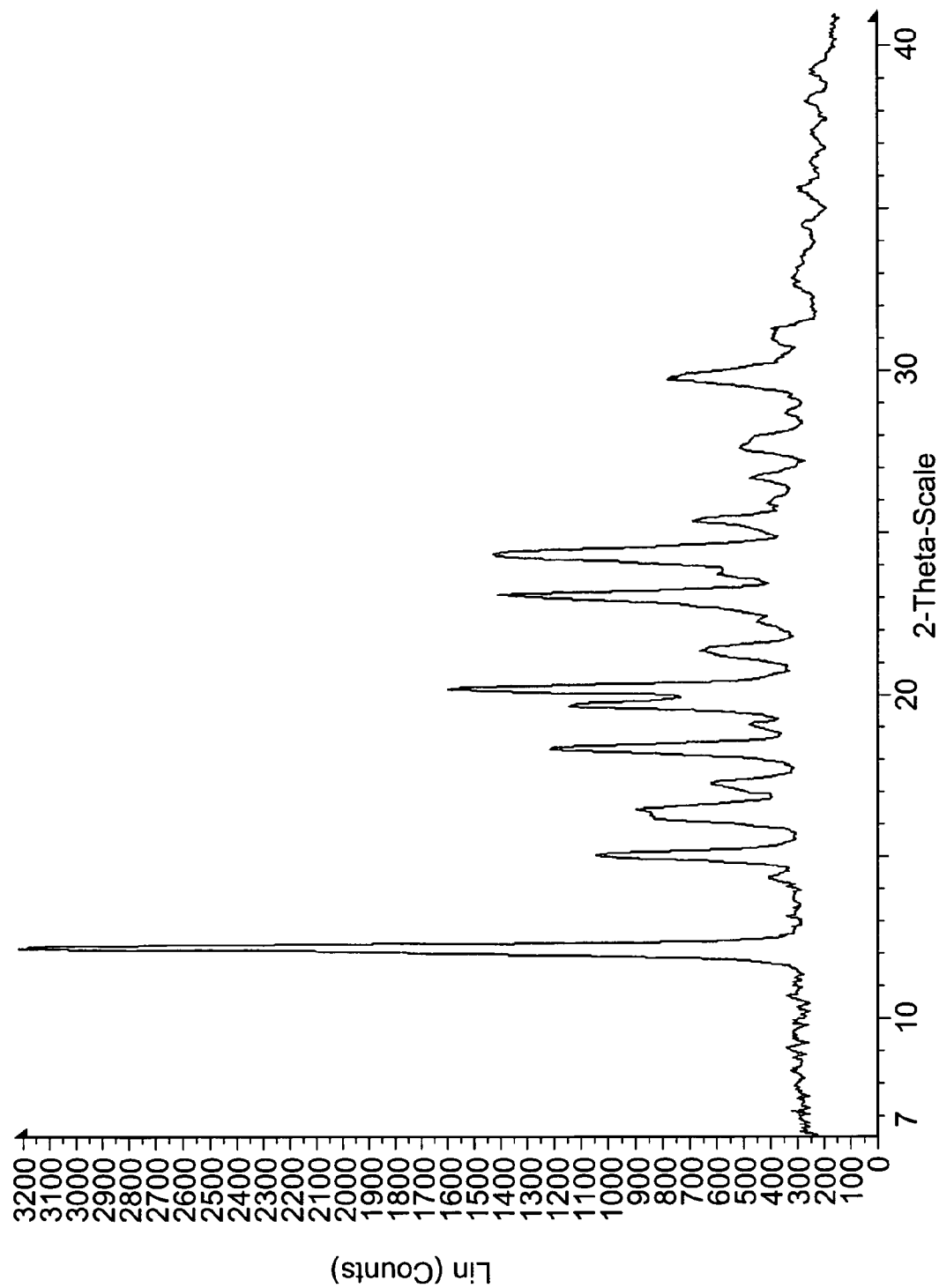
Figure 9:
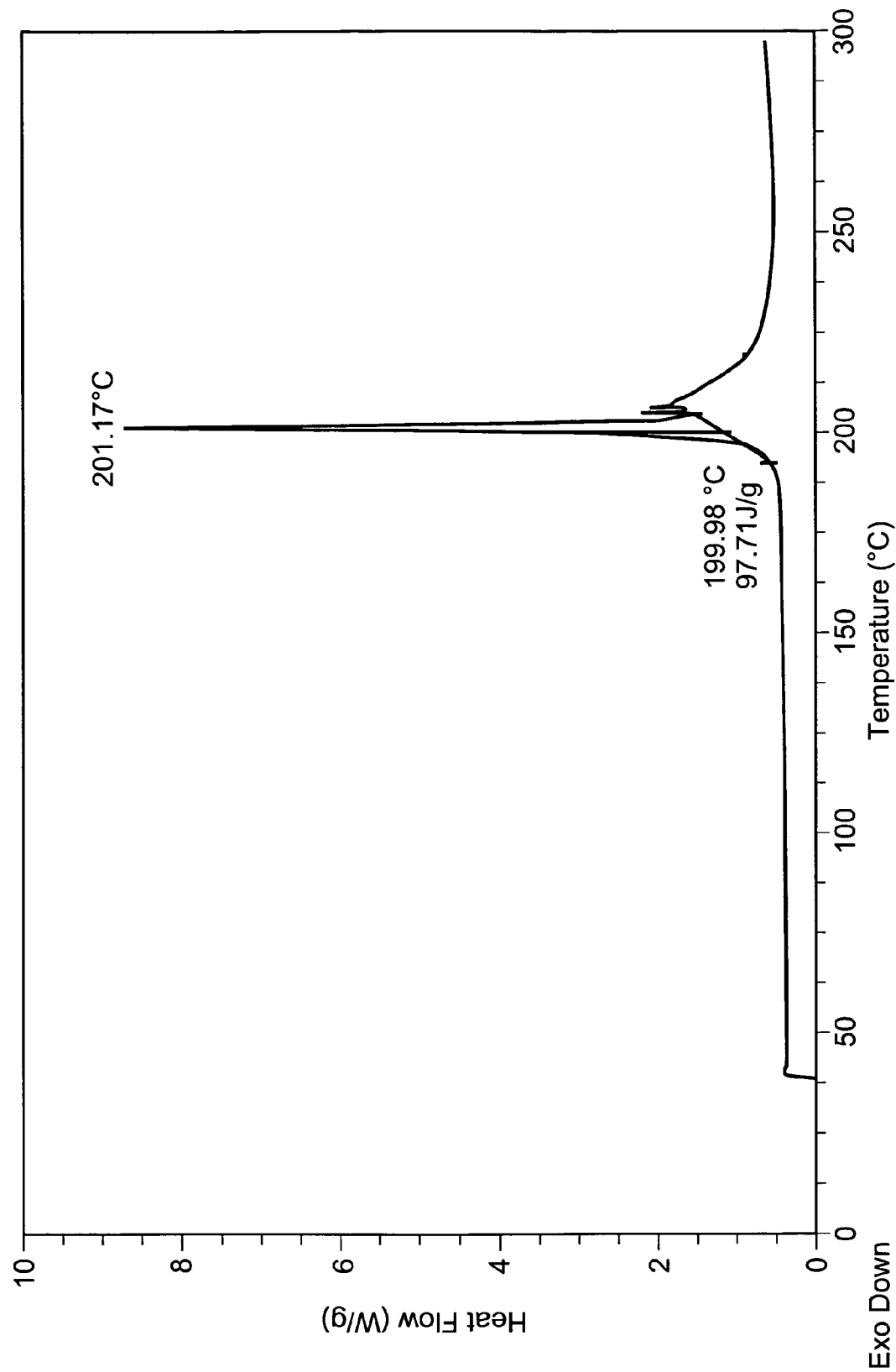
Figure 10:
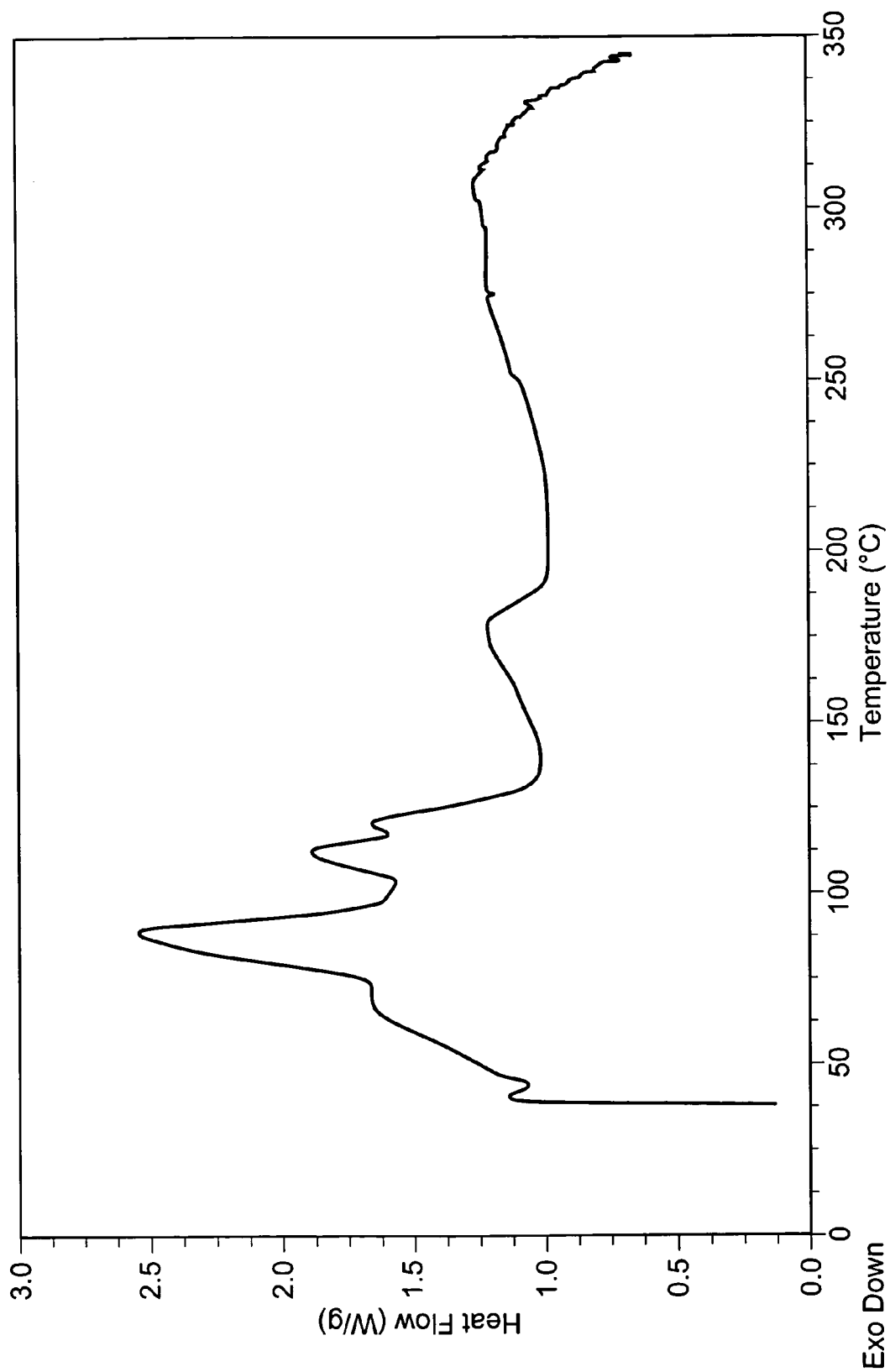
Figure 11:
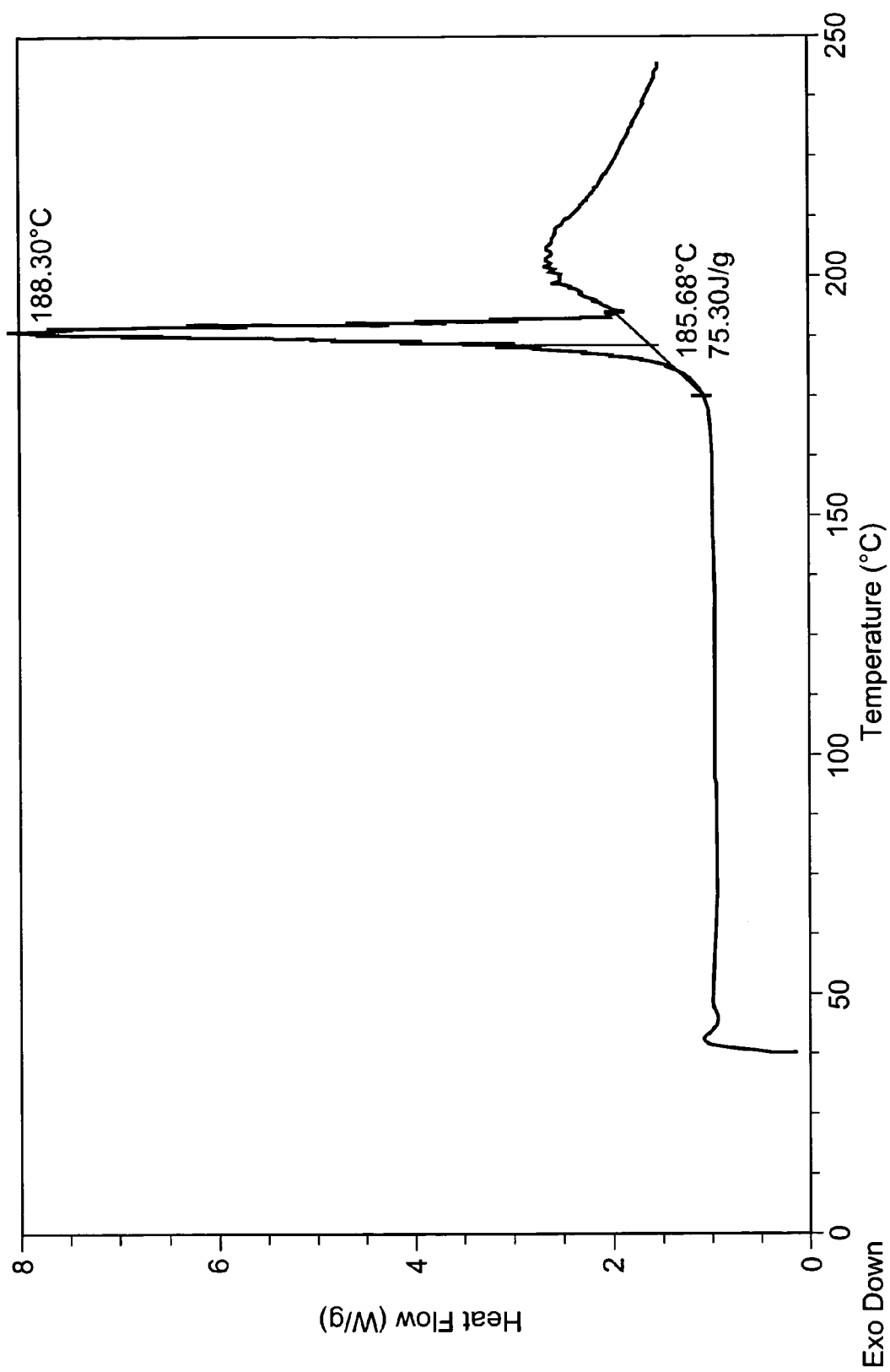
Figure 12:
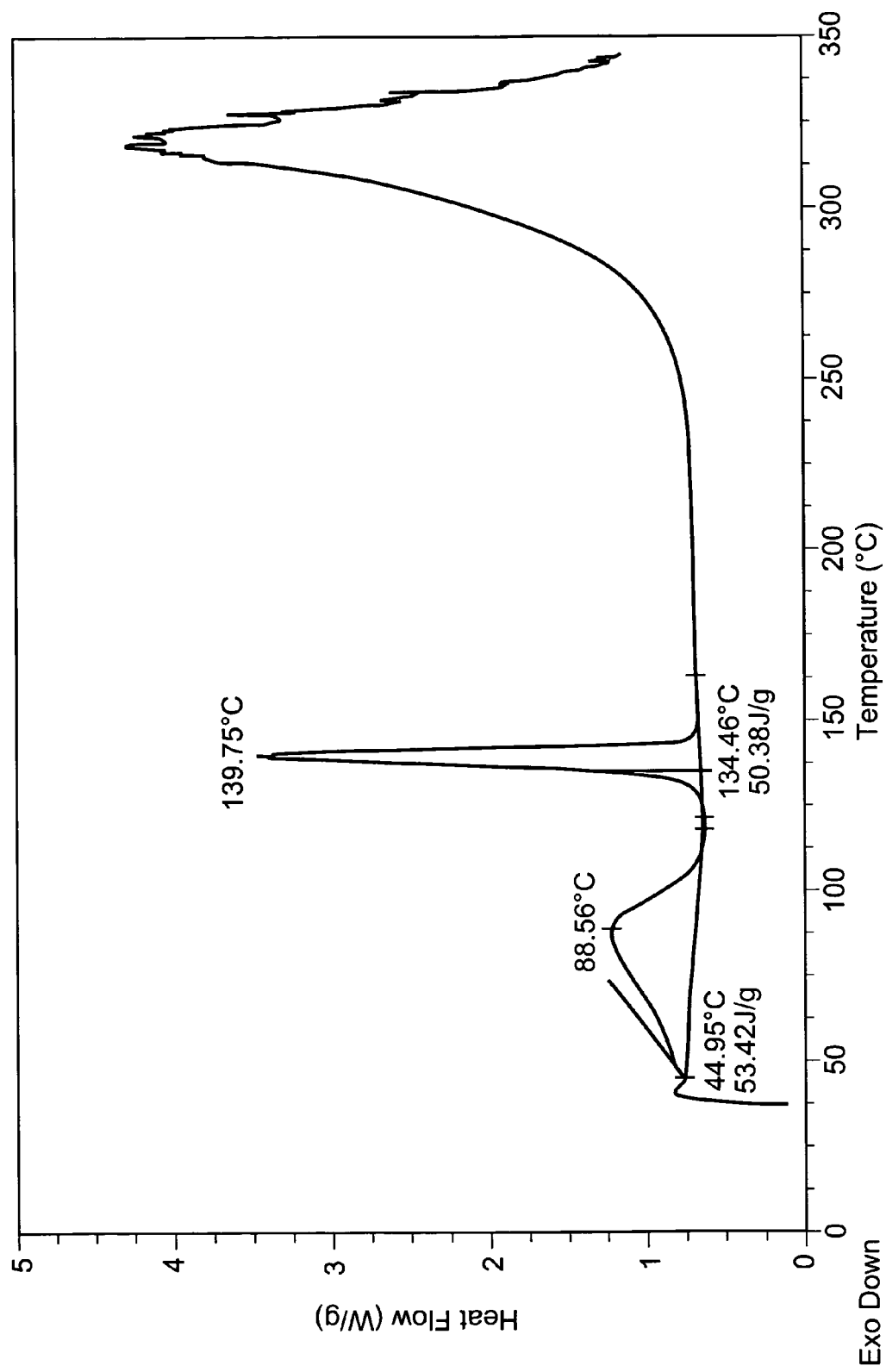
Figure 13:
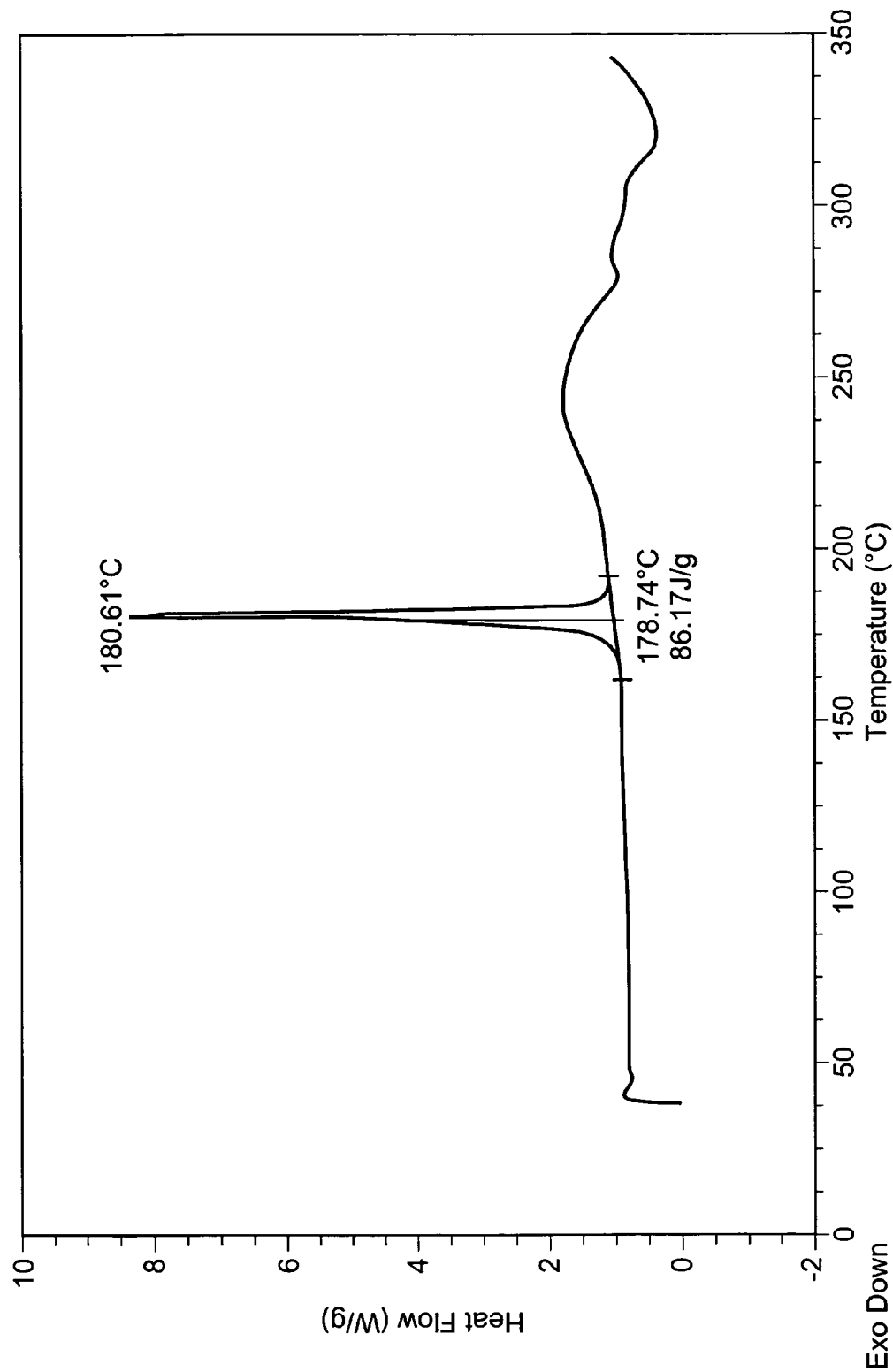
Figure 14:
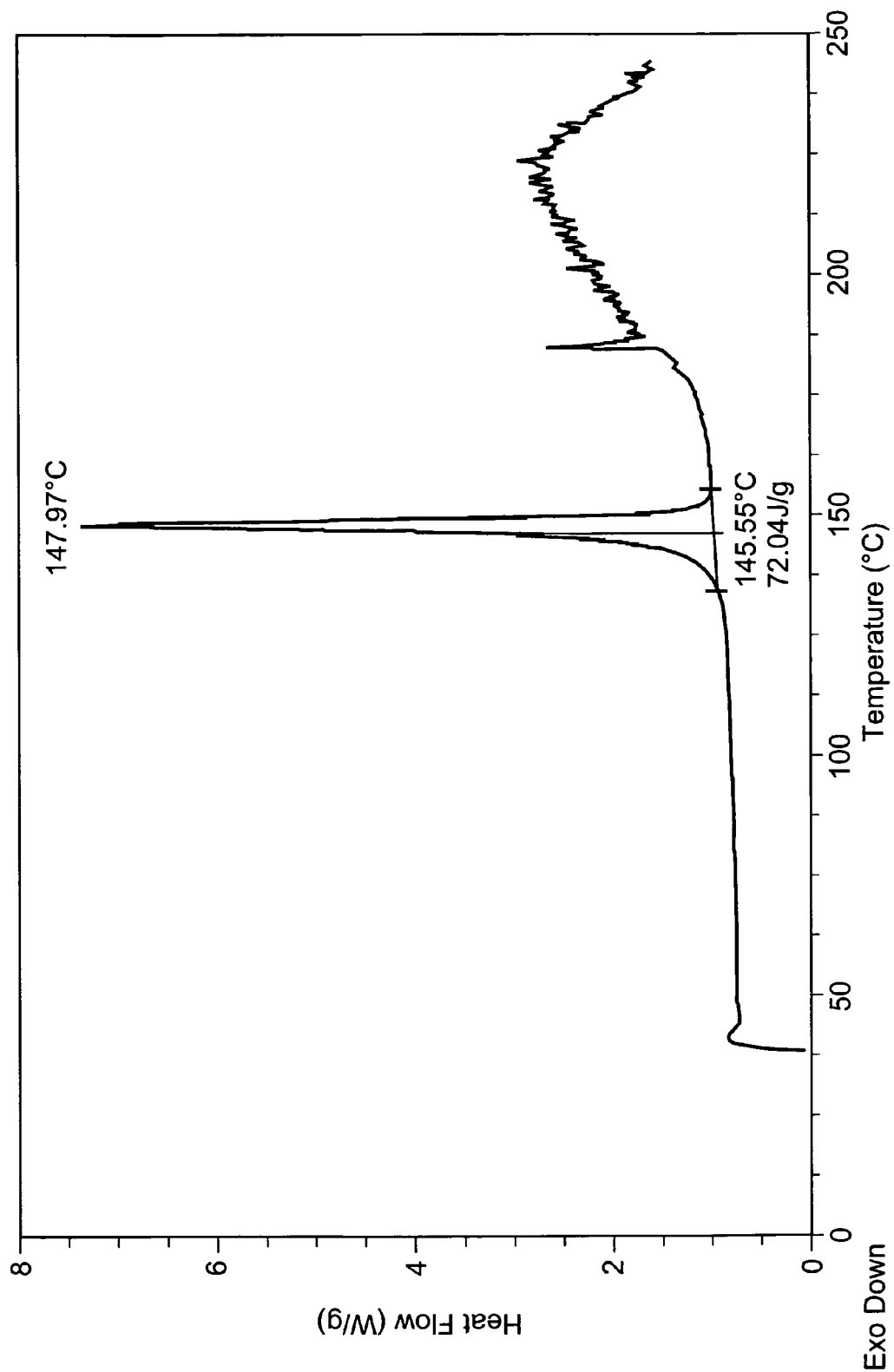
Figure 15:
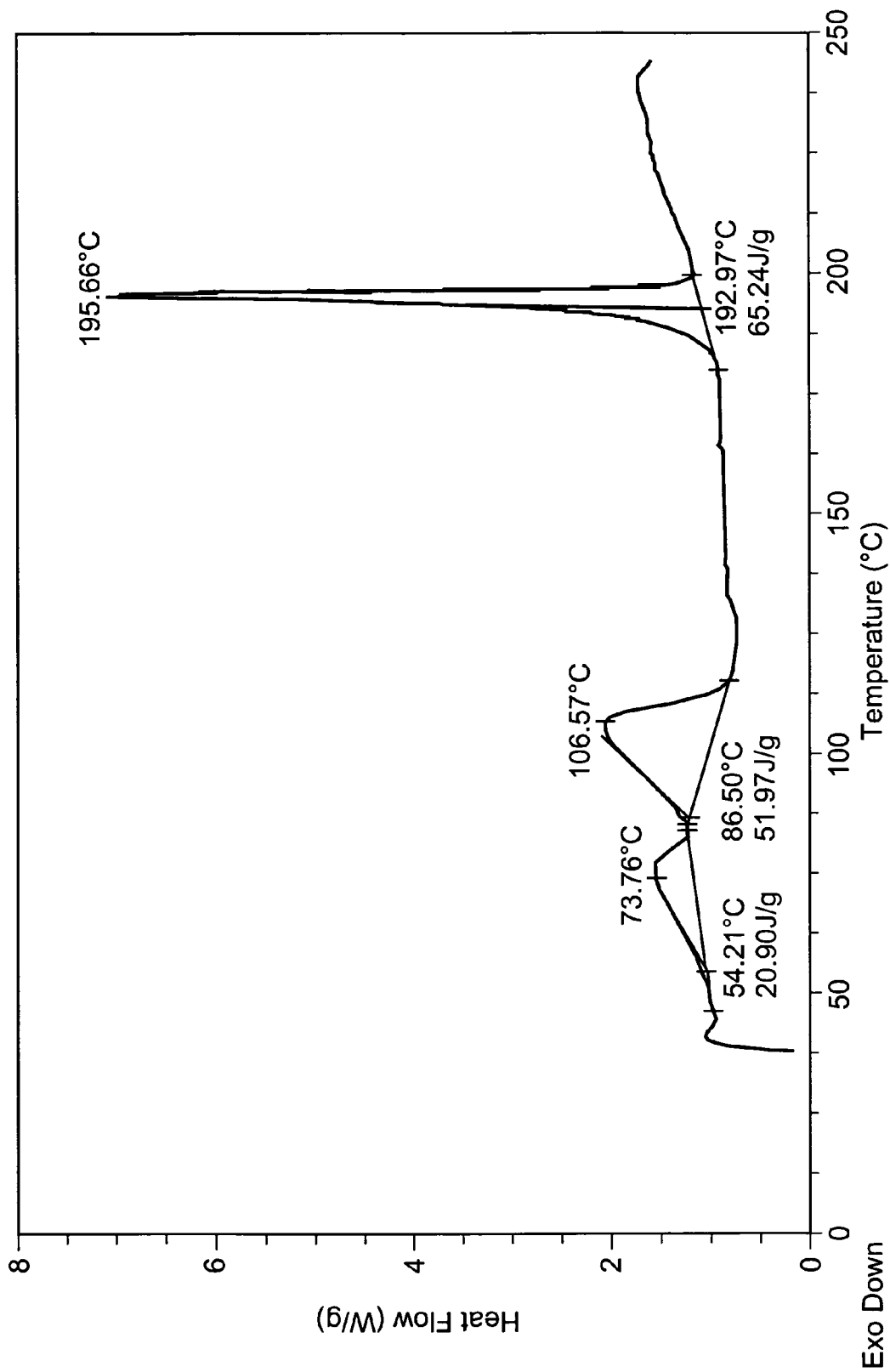

FIGS. 1-8 are powder x-ray diffraction (PXRD) spectra of: 1-(2-fluorophenyl)-3-(piperidin-4-yloxy)-1H-indazole L-tartrate (FIG. 1); 1-(2-fluorophenyl)-3-(piperidin-4-yloxy)-1H-indazole edisylate (FIG. 2); 1-(2-fluorophenyl)-3-(piperidin-4-yloxy)-1H-indazole fumarate (FIG. 3); 1-(2-fluorophenyl)-3-(piperidin-4-yloxy)-1H-indazole hydrobromide (FIG. 4); 1-(2-fluorophenyl)-3-(piperidin-4-yloxy)-1H-indazole hemi-L-tartrate (FIG. 5); 1-(2-fluorophenyl)-3-(piperidin-4-yloxy)-1H-indazole L-malate (FIG. 6); 1-(2-fluorophenyl)-3-(piperidin-4-yloxy)-1H-indazole phosphate (FIG. 7); and 1-(2-fluorophenyl)-3-(piperidin-4-yloxy)-1H-indazole sulfate (FIG. 8).

Figure 16:
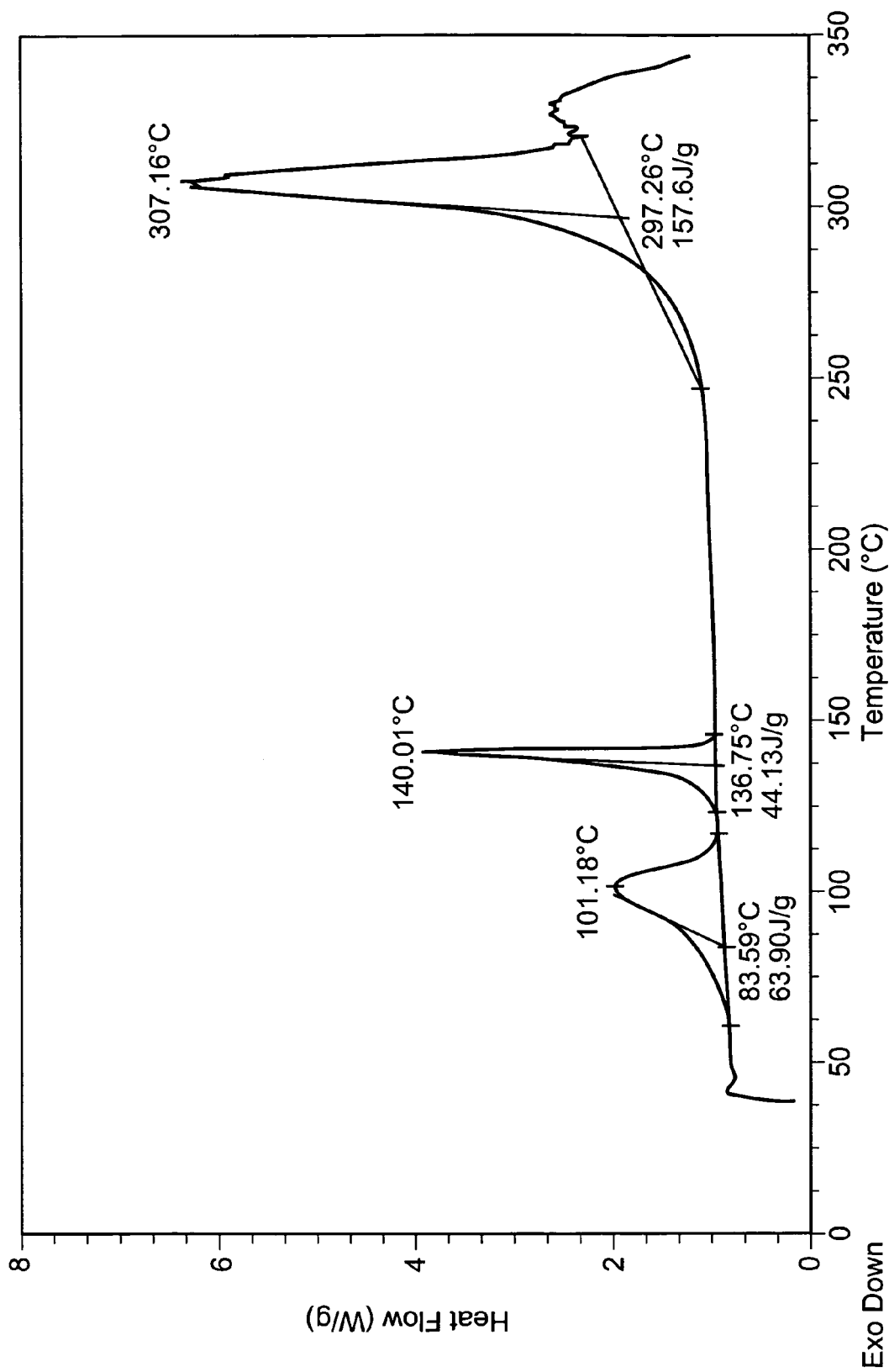

FIGS. 9-16 are differential scanning calorimetry thermal profiles of: 1-(2-fluorophenyl)-3-(piperidin-4-yloxy)-1H-indazole L-tartrate (FIG. 9); 1-(2-fluorophenyl)-3-(piperidin-4-yloxy)-1H-indazole edisylate (FIG. 10); 1-(2-fluorophenyl)-3-(piperidin-4-yloxy)-1H-indazole fumarate (FIG. 11); 1-(2-fluorophenyl)-3-(piperidin-4-yloxy)-1H-indazole hydrobromide (FIG. 12); 1-(2-fluorophenyl)-3-(piperidin-4-yloxy)-1H-indazole hemi-L-tartrate (FIG. 13); 1-(2-fluorophenyl)-3-(piperidin-4-yloxy)-1H-indazole L-malate (FIG. 14); 1-(2-fluorophenyl)-3-(piperidin-4-yloxy)-1H-indazole phosphate (FIG. 15); and 1-(2-fluorophenyl)-3-(piperidin-4-yloxy)-1H-indazole sulfate (FIG. 16).

Figure 17:
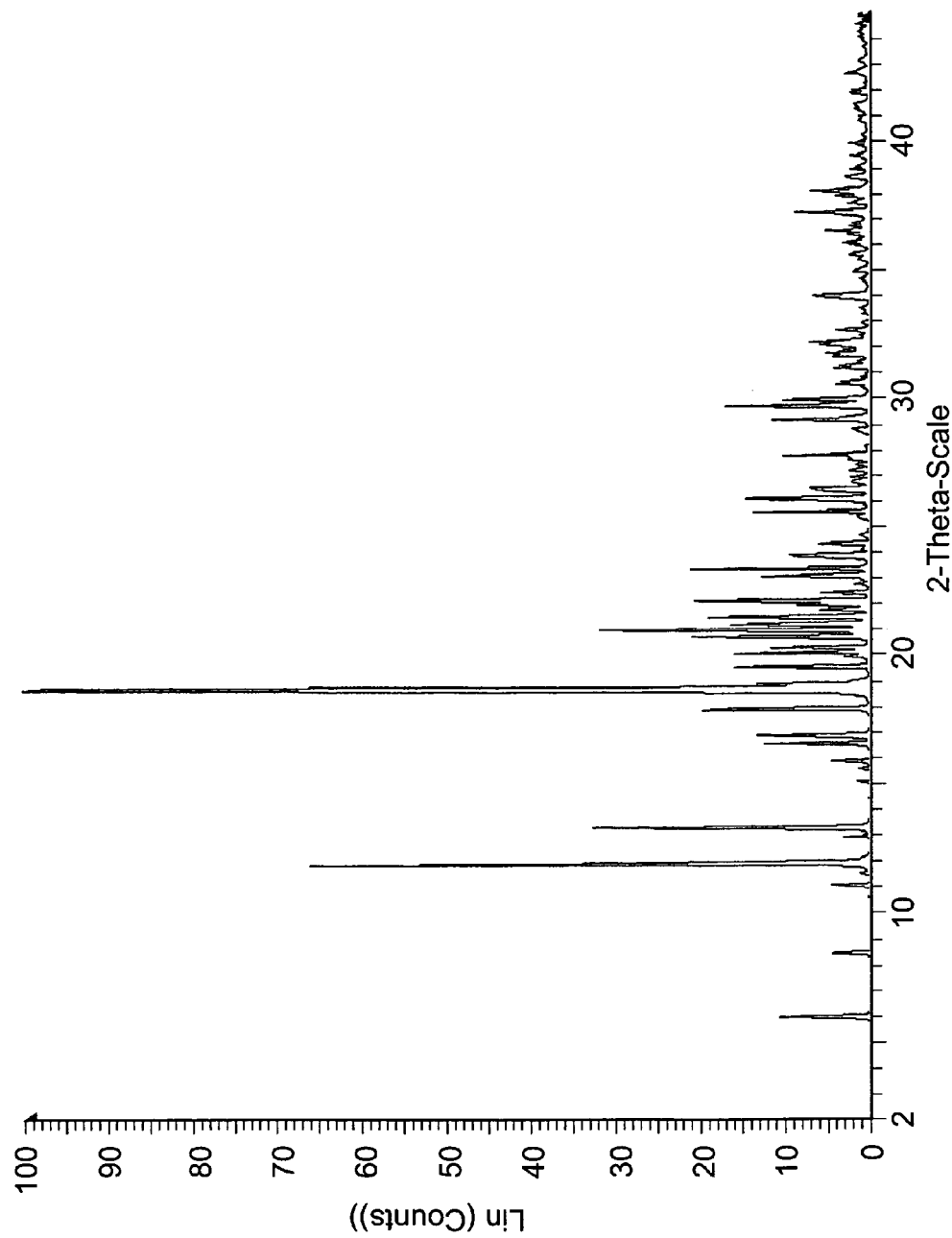

FIG. 17 is a calculated powder x-ray diffraction (PXRD) spectrum of: 1-(2-fluorophenyl)-3-(piperidin-4-yloxy)-1H-indazole L-tartrate.

DETAILED DESCRIPTION OF THE INVENTION

Preparation of Compounds

Compounds of the present invention (e.g., compounds of Formula I) can be prepared by applying synthetic methodology known in the art and synthetic methodology outlined in the schemes set forth below.

Scheme 1

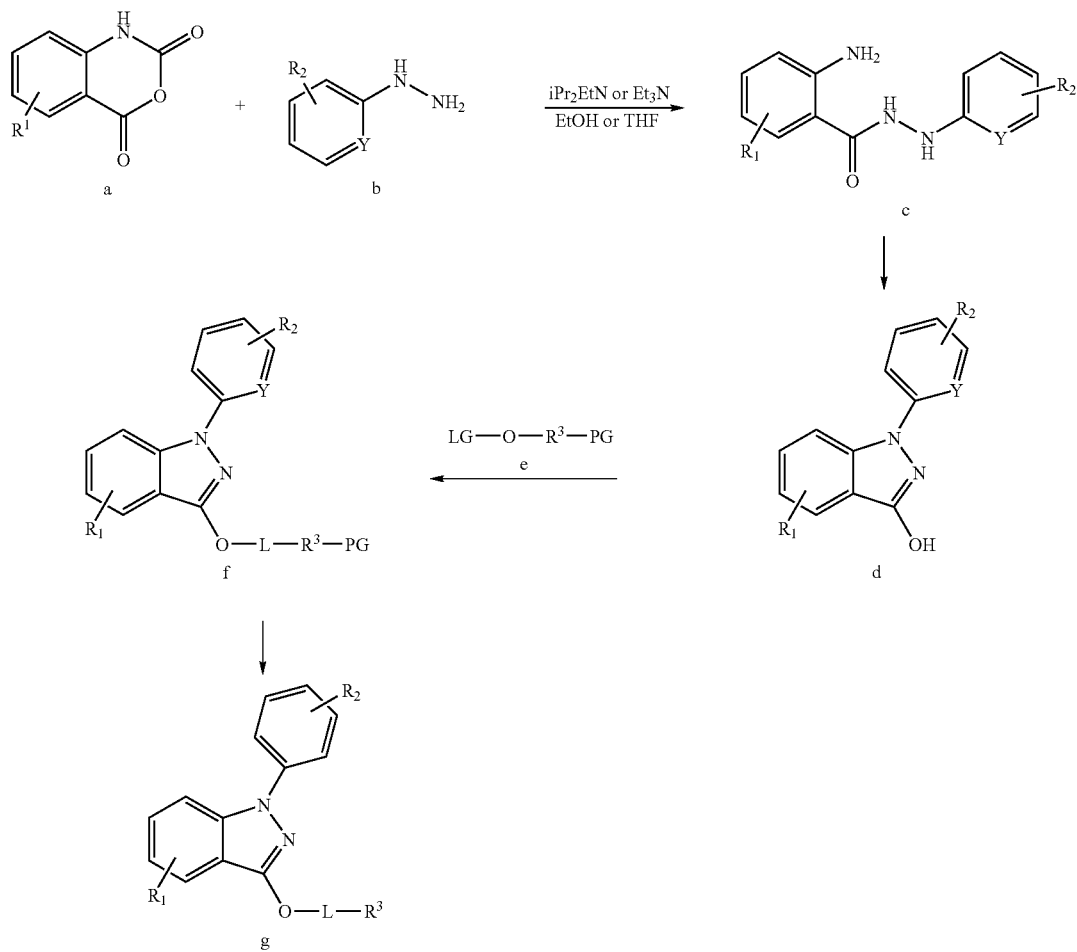

A phenylhydrazine b (e.g., 2-fluorophenylhydrazine) or pyridinylhydrazine (e.g., 2-hydrazinopyridine) that has been treated with or without a base such as N,N-diisopropylethylamine or triethylamine in a suitable solvent (e.g., ethanol or tetrahydrofuran (THF)) is reacted with the anhydride a (e.g., isatoic anhydride) to give the hydrazide c (e.g., 2-aminobenzoic acid N'-(2-fluoro-phenyl)-hydrazide). c is then acidified and reacted with sodium nitrite, followed by ethanol to generate the indazole d (e.g., 1-(2-fluoro-phenyl)-1H-indazol-3-ol).

A mixture of the 1-(2-fluoro-phenyl)-1H-indazol-3-ol d, a compound e (LG-O-L-$R^3$-PG) and a base such as a hydride base (e.g., sodium hydride, potassium hydride), 2-tert-butylimino-2-diethylamino-1,3-dimethyl-perhydro1,3,2-diazaphosphorine (BEMP), 2-tert-butylimino-2-diethylamino-1,3-dimethyl-perhydro1,3,2-diazaphosphorine on polystyrene (PS-BEMP resin), $Na_2CO_3$, $K_2CO_3$, or $Cs_2CO_3$ in anhydrous DMF (dimethylformamide) are reacted to provide f (e.g., 4-[1-(2-fluoro-phenyl)-1H-indazol-3-yloxy]-piperidine-1-carboxylic acid tert-butyl ester). LG of e is a suitable leaving group such as methanesulfonyloxy, benzenesulfonyloxy, toluene-4-sulfonyloxy, and trifluoromethanesulfonyloxy. PG of e is a suitable amine protecting group such as t-butyl-ester (BOC). Those of skill in the art will recognize that a wide variety of protecting groups in addition to BOC can be used as a suitable amine protecting group for $R^3$ (see e.g., Greene and Wuts, *Protective Groups in Organic Synthesis*, Wiley-Interscience; 3rd edition (1999). Thus, an example of e is 4-methanesulfonyloxy-piperidine-1-carboxylic acid tert-butyl ester. The PG substituent of f is then removed to provide g (e.g., 1-(2-Fluoro-phenyl)-3-(piperidin-4-yloxy)-1H-indazole). Groups such as BOC may be hydrolyzed under acidic conditions.

Scheme 2

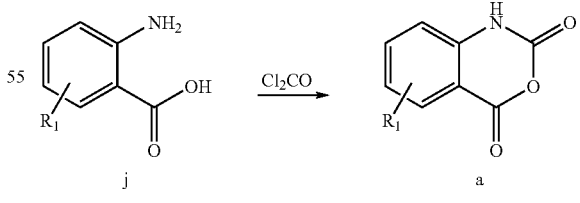

Scheme 2 depicts the synthesis of the anhydride a. a (e.g., 6-fluoro-1H-benzo[d][1,3]oxazine-2,4-dione) can be synthesized by reacting a 2-aminobenzoic acid j (e.g., 2-amino-5-fluorobenzoic acid) with a base such as sodium carbonate in water, followed by the addition of a phosgene solution in toluene.

Scheme 3

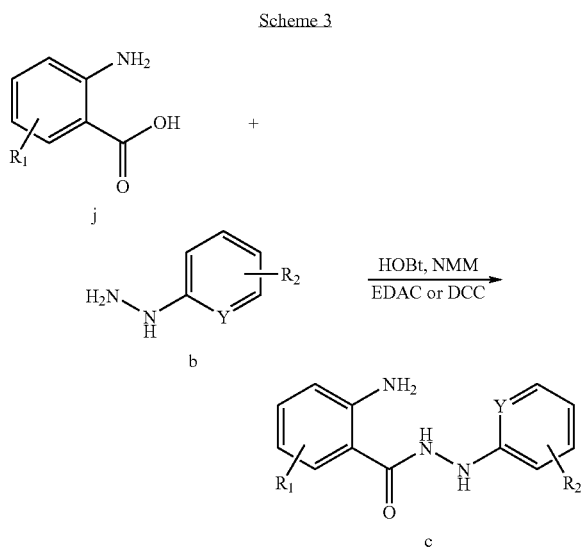

In Scheme 3, an alternative synthetic route to c is depicted. A 2-amino-benzoic acid j (e.g., 2-amino-5-chloro-benzoic acid) is reacted with a hydrazine b (e.g., 2,5-difluoro-phenyl)-hydrazine) in the presence of a coupling reagent such as 1-[3-(dimethylamino)propyl]-3-ethylcarbodiimide (EDCI), dicyclohexylcarbodiimide (DCC), 1,1'-carbonyldiimidazole (CDI) and a base such as dimethylaminopyridine (DMAP), N,N-diisopropylethylamine (DIPEA), or triethylamine to afford c (e.g., 2-amino-5-chloro-benzoic acid N'-(2,5-difluoro-phenyl)-hydrazide). Alternatively, j can be reacted with b and HOBT (1-hydroxybenzotriazole hydrate) in a solvent such as dry THF (tetrahydrofuran). N-Me-morpholine (NMM) is then added and before adding EDAC-HCl (1-[3-(dimethylamino)propyl]-3-ethylcarbodiimide hydrochloride) to provide compound c.

Scheme 4 depicts the synthesis of the 1H-pyrazolo[3,4-b]pyridine q. A nicotinoylchloride k (e.g., 2-chloronicotinoyl chloride) is reacted with a hydrazine m (e.g., phenylhydrazine) and a base such as triethylamine in a solvent such as anhydrous methylene chloride to give o (e.g., 1-phenyl-1H-pyrazolo[3,4-b]pyridin-3-ol). The compound o is then cyclized by heating at 175° C. to provide p. p is reacted as in the transformation of d to g in Scheme 1 to provide q.

Evaluation of Compounds

Compounds of the present invention (e.g., compounds of Formula I and pharmaceutically acceptable salts thereof) can be assayed for their ability to inhibit a norepinephrine transporter and/or a serotonin transporter.

The ability of the compounds of the present invention to inhibit a norepinephrine transporter and/or a serotonin transporter can be determined using conventional radioligand receptor transport assays. The receptors can be heterologously expressed in cell lines and experiments conducted in membrane preparations from the cell lines that express a norepinephrine transporter and/or a serotonin transporter.

In certain embodiments, the compounds of formula I may be assayed for their ability to alleviate capsaicin-induced mechanical allodynia in a rat (e.g., Sluka, K A, (2002) *J of Neuroscience*, 22(13): 5687-5693). For example, a rat model of capsaicin-induced mechanical allodynia can be carried out as follows:

On day 0, male Sprague-Dawley rats (~150 g) in the dark cycle are placed in suspended wire-bottom cages and allowed to acclimate for 0.5 h in a darkened, quiet room. The day 0 paw withdrawal threshold (PWT) is determined on the left hind paw by Von Frey hair assessment using the Dixon up and down method. After assessment, the plantar muscle of the right hind paw is injected with 100 µl capsaicin (0.25% in 10% ethanol, 10% Tween 80, in sterile saline). On day 6 the PWT of the left hindpaw (contralateral from injection site) is determined for each animal. Animals from the day 6 prereads with PWT≦11.7 g are considered allodynic responders and are regrouped so that each cage had similar mean PWT val- Scheme 4

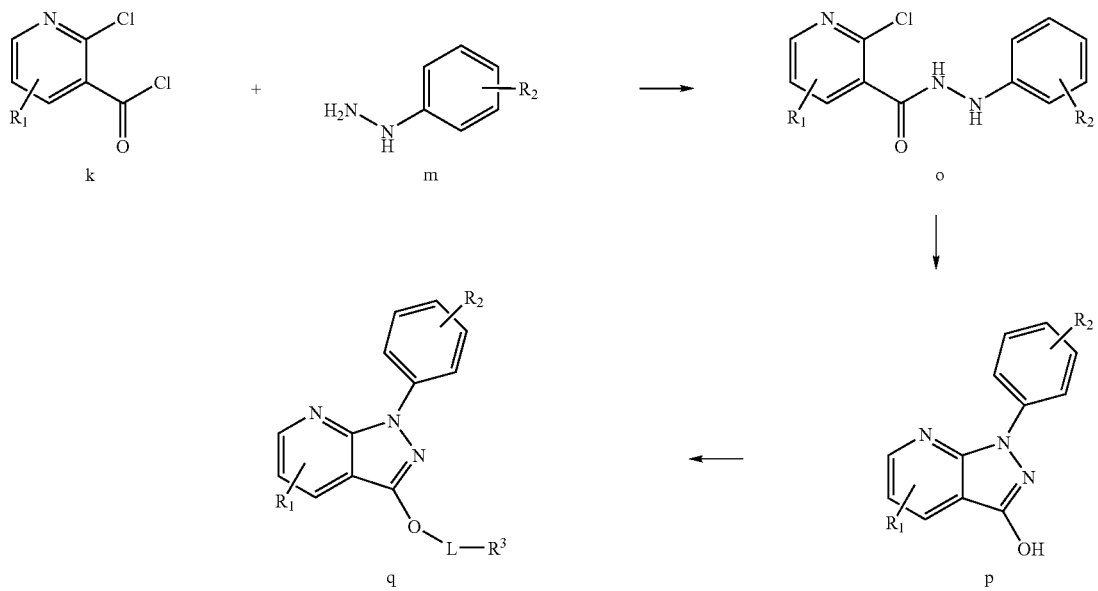

ues. On day 7, responders are dosed (e.g., orally, intraperitoneally, and subcutaneously, etc.) with 10 ml/kg vehicle (0.5% HPMC(hydroxy-propylmethylcellulose)/0.2% Tween™ 80), or vehicle plus compound. The contralateral PWT values are determined at 2 hours (or at about the time corresponding to the estimated $C_{max}$) after the single dose, with the investigator blinded to the dosing scheme. Those of skill in the art can determine the appropriate time to determine the contralateral PWT value (e.g., 1 hour, 2 hours, etc.).

For each animal, the day 6 PWT value is subtracted from the 2 hour PWT value to give a delta PWT value that represents the change in PWT due to the 2 hour drug treatment. In addition, the day 6 PWT is subtracted from the day 0 PWT to give the baseline window of allodynia present in each animal. To determine % inhibition of allodynia of each animal normalized for vehicle controls, the following formula is used:

$$\% \text{ Inhibiton of Allodynia} = 100 \times \frac{(\text{Delta } PWT(\text{drug}) - \text{mean Delta } PWT(\text{vehicle}))}{(\text{Baseline} - \text{mean Delta } PWT(\text{vehicle}))}.$$

Pharmaceutically Acceptable Salts and Solvates

The compounds to be used in the present invention can exist in unsolvated forms as well as solvated forms, including hydrated forms. In general, the solvated forms, including hydrated forms are intended to be encompassed within the scope of the present invention.

The compounds of the present invention (e.g., compounds of Formula I) are capable of further forming both pharmaceutically acceptable salts, including but not limited to acid addition and/or base salts. Pharmaceutically acceptable salts of the compounds of formula (I) include the acid addition and base salts (including disalts) thereof. Examples of suitable salts can be found for example in Stahl and Wermuth, *Handbook of Pharmaceutical Salts: Properties, Selection, and Use*, Wiley-V C H, Weinheim, Germany (2002); and Berge et al., "Pharmaceutical Salts," *J. of Pharmaceutical Science*, 1977; 66:1-19.

Pharmaceutically acceptable acid addition salts of the compounds of Formula I include non-toxic salts derived from inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include the acetate, aspartate, benzoate, besylate (benzenesulfonate), bicarbonate/carbonate, bisulfate, caprylate, camsylate (camphor sulfonate), chlorobenzoate, citrate, edisylate(1,2-ethane disulfonate), dihydrogenphosphate, dinitrobenzoate, esylate (ethane sulfonate), fumarate, gluceptate, gluconate, glucuronate, hibenzate, hydrochloride/chloride, hydrobromide/bromide, hydroiodide/iodide, isobutyrate, monohydrogen phosphate, isethionate, D-lactate, L-lactate, malate, maleate, malonate, mandelate, mesylate (methanesulfonate), metaphosphate, methylbenzoate, methylsulfate, 2-napsylate (2-naphthalene sulfonate), nicotinate, nitrate, orotate, oxalate, palmoate, phenylacetate, phosphate, phthalate, propionate, pyrophosphate, pyrosulfate, saccharate, sebacate, stearate, suberate, succinate sulfate, sulfite, D-tartrate, L-tartrate, tosylate (toluene sulfonate), and xinafoate salts, and the like of compounds of Formula I. Also contemplated are the salts of amino acids such as arginate, gluconate, galacturonate, and the like.

Acid addition salts of the basic compounds may be prepared by contacting the free base form with a sufficient amount of the desired acid to produce the salt. The free base form may be regenerated by contacting the salt form with a base and isolating the free base. The free base forms differ from their respective salt forms somewhat in certain physical properties such as solubility in polar solvents.

Pharmaceutically acceptable base addition salts may be formed with metals or amines, such as alkali and alkaline earth metal hydroxides, or of organic amines. Examples of metals used as cations are aluminum, calcium, magnesium, potassium, sodium, and the like. Examples of suitable amines include arginine, choline, chloroprocaine, N,N'-dibenzylethylenediamine, diethylamine, diethanolamine, diolamine, ethylenediamine (ethane-1,2-diamine), glycine, lysine, meglumine, N-methylglucamine, olamine, procaine (benzathine), and tromethamine.

The base addition salts of acidic compounds may be prepared by contacting the free acid form with a sufficient amount of the desired base to produce the salt. The free acid form may be regenerated by contacting the salt form with an acid and isolating the free acid. The free acid forms may differ from their respective salt forms somewhat in certain physical properties such as solubility in polar solvents.

Pharmaceutical Compositions and Methods of Administration

The present invention also provides for pharmaceutical compositions comprising a therapeutically effective amount of a compound of Formula I, or a pharmaceutically acceptable salt thereof together with a pharmaceutically acceptable carrier, diluent, or excipient therefor. The phrase "pharmaceutical composition" refers to a composition suitable for administration in medical or veterinary use. The phrase "therapeutically effective amount" means an amount of a compound, or a pharmaceutically acceptable salt thereof, sufficient to inhibit, halt, or allow an improvement in the disease being treated when administered alone or in conjunction with another pharmaceutical agent or treatment in a particular subject or subject population. For example in a human or other mammal, a therapeutically effective amount can be determined experimentally in a laboratory or clinical setting, for the particular disease and subject being treated.

It should be appreciated that determination of proper dosage forms, dosage amounts, and routes of administration is within the level of ordinary skill in the pharmaceutical and medical arts, and is described below.

A compound of the present invention can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Preferably, a compound of the present invention will cause a decrease in symptoms or a disease indicia associated with a norepinephrine-mediated and/or serotonin-mediated disorder as measured quantitatively or qualitatively.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets contain from 1% to 95% (w/w) of the active compound. In certain embodiments, the active compound ranges from 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg, or from 1% to 95% (w/w) of a unit dose, according to the particular application and the potency of the active component. For example, a unit dose may contain 10, 15, 20, 25, 30, 40, or 50 mg of a compound of the present invention. The composition can, if desired, also contain other compatible therapeutic agents.

Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington: The Science and Practice of Pharmacy*, 20th ed., Gennaro et al. Eds., Lippincott Williams and Wilkins, 2000).

A compound of the present invention, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In the practice of the present invention, compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

The dose administered to a subject, in the context of the present invention should be sufficient to affect a beneficial therapeutic response in the subject over time. The term "subject" refers to a member of the class Mammalia. Examples of mammals include, without limitation, humans, primates, chimpanzees, rodents, mice, rats, rabbits, horses, livestock, dogs, cats, sheep, and cows. In certain embodiments, the "subject" is a human.

The dose will be determined by the efficacy of the particular compound employed and the condition of the subject, as well as the body weight or surface area of the subject to be treated. The size of the dose also will be determined by the existence, nature, and extent of any adverse side effects that accompany the administration of a particular compound in a particular subject. In determining the effective amount of the compound to be administered in the treatment or prophylaxis of the disease being treated, the physician can evaluate factors such as the circulating plasma levels of the compound, compound toxicities, and/or the progression of the disease, etc. In general, the dose equivalent of a compound is from about 1 μg/kg to 100 mg/kg for a typical subject. Many different administration methods are known to those of skill in the art.

For administration, compounds of the present invention can be administered at a rate determined by factors that can include, but are not limited to, the pharmacokinetic profile of the compound, contraindicated drugs, and the side effects of the compound at various concentrations, as applied to the mass and overall health of the subject. Administration can be accomplished via single or divided doses.

An example of a typical tablet includes the following:

TABLET FORMULATION EXAMPLE 1
Tablet Formulation

| Ingredient | Amount |
| --- | --- |
| A Compound of Formula I | 50 mg |
| Lactose | 80 mg |
| Cornstarch (for mix) | 10 mg |
| Cornstarch (for paste) | 8 mg |
| Magnesium Stearate (1%) | 2 mg |
|  | 150 mg |

The compounds of the present invention (e.g., a compound of Formula I, or a pharmaceutically acceptable salt thereof) can be mixed with the lactose and cornstarch (for mix) and blended to uniformity to a powder. The cornstarch (for paste) is suspended in 6 ml of water and heated with stirring to form a paste. The paste is added to the mixed powder, and the mixture is granulated. The wet granules are passed through a No. 8 hard screen and dried at 50° C. The mixture is lubricated with 1% magnesium stearate and compressed into a tablet. The tablets are administered to a patient at the rate of 1 to 4 each day for treatment of a norepinephrine-mediated and/or serotonin-mediated disorder.

Methods for Treating Norepinephrine-Mediated and/or Serotonin-Mediated Disorders The compounds of the present invention and pharmaceutical compositions comprising a compound of the present invention can be administered to treat a subject suffering from a norepinephrine-mediated and/or serotonin-mediated disorder, including central nervous disorders, which is alleviated by the inhibition of a norepinephrine transporters and/or serotonin transporters.

Norepinephrine-mediated and/or serotonin-mediated disorders can be treated prophylactically, acutely, and chronically using compounds of the present invention, depending on the nature of the disease. Typically, the host or subject in each of these methods is human, although other mammals can also benefit from the administration of a compound of the present invention.

In therapeutic applications, the compounds of the present invention can be prepared and administered in a wide variety of oral and parenteral dosage forms. The term "administering" refers to the method of contacting a compound with a subject. Thus, the compounds of the present invention can be administered by injection, that is, intravenously, intramuscularly, intracutaneously, subcutaneously, intraduodenally, parentally, or intraperitoneally. Also, the compounds described herein can be administered by inhalation, for example, intranasally. Additionally, the compounds of the present invention can be administered transdermally, topically, and via implantation. In certain embodiments, the compounds of the present invention are delivered orally. The compounds can also be delivered rectally, bucally, intravaginally, ocularly, or by insufflation.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the disease being treated, and the compound being employed. Determination of the proper dosage for a particular situation is within the skill of the practitioner. Generally, treatment is initiated with smaller dosages, which are less than the optimum dose of the compound. Thereafter, the dosage is increased by small increments until the optimum effect under circumstances is reached. For convenience, the total daily dosage may be divided and administered in portions during the day, if desired. The term "treatment" includes the acute, chronic, or prophylactic diminishment or alleviation of at least one symptom or characteristic associated with or caused by the disease being treated. For example, treatment can include diminishment of several symptoms of a disease, inhibition of the pathological progression of a disease, or complete eradication of a disease.

The present invention also relates to a method of treating a norepinephrine-mediated and/or serotonin-mediated disorder comprising administering to a mammal in need of such treatment a therapeutically effective amount of a compound of formula I. Examples of norepinephrine-mediated and/or serotonin-mediated disorders include fibromyalgia, single episodic or recurrent major depressive disorders, dysthymic disorders, depressive neurosis and neurotic depression, melancholic depression including anorexia, weight loss, insomnia, early morning waking or psychomotor retardation; atypical depression (or reactive depression) including increased appetite, hypersomnia, psychomotor agitation or irritability, seasonal affective disorder and pediatric depression; bipolar disorders or manic depression, for example, bipolar I disorder, bipolar II disorder and cyclothymic disorder; conduct disorder; attention deficit hyperactivity disorder (ADHD); disruptive behavior disorder; behavioral disturbances associated with mental retardation, autistic disorder, and conduct disorder; anxiety disorders such as panic disorder with or without agoraphobia, agoraphobia without history of panic disorder, specific phobias, for example, specific animal phobias, social anxiety, social phobia, obsessive-compulsive disorder, stress disorders including post-traumatic stress disorder and acute stress disorder, and generalized anxiety disorders; borderline personality disorder; schizophrenia and other psychotic disorders, for example, schizophreniform disorders, schizoaffective disorders, delusional disorders, brief psychotic disorders, shared psychotic disorders, psychotic disorders with delusions or hallucinations, psychotic episodes of anxiety, anxiety associated with psychosis, psychotic mood disorders such as severe major depressive disorder; mood disorders associated with psychotic disorders such as acute mania and depression associated with bipolar disorder; mood disorders associated with schizophrenia; delirium, dementia, and amnestic and other cognitive or neurodegenerative disorders, such as Parkinson's disease (PD), Huntington's disease (HD), Alzheimer's disease, senile dementia, dementia of the Alzheimer's type, memory disorders, loss of executive function, vascular dementia, and other dementias, for example, due to HIV disease, head trauma, Parkinson's disease, Huntington's disease, Pick's disease, Creutzfeldt-Jakob disease, or due to multiple etiologies; movement disorders such as akinesias, dyskinesias, including familial paroxysmal dyskinesias, spasticities, Tourette's syndrome, Scott syndrome, palsys (e.g., Bell's palsy, cerebral palsy, birth palsy, brachial palsy, wasting palsy, ischemic palsy, progressive bulbar palsy and other palsys), and akinetic-rigid syndrome; extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremour; chemical dependencies and addictions (e.g., dependencies on, or addictions to, alcohol, heroin, cocaine, benzodiazepines, nicotine, or phenobarbitol) and behavioral addictions such as an addiction to gambling; and ocular disorders such as glaucoma and ischemic retinopathy.

In one particular embodiment, patients suffering from fibromyalgia are administered a therapeutically effective amount of a compound of formula I, or a pharmaceutically acceptable salt thereof. Patients suffering from fibromyalgia typically exhibit a history of widespread pain, and the presence of pain at 11 out of 18 points upon palpatation (see e.g., Wolfe et al. (1990) Arthritis Rheum. 33:160-172). Fibromyalgia patients generally display pain perception abnormalities in the form of both allodynia (pain from innocuous stimulation) and hyperalgesia (an increased sensitivity to a painful stimulation).

Fibromyalgia patients typically also exhibit a range of other symptoms, including sleep disturbance and fatigue. Although less common than pain, fatigue, and sleep problems, a variety of other symptoms may occur as well. These include headaches, morning stiffness, difficulty concentrating, a circulatory problem that affects the small blood vessels of the skin (Raynaud's phenomenon), and irritable bowel syndrome. As with many conditions that cause chronic pain, anxiety and depression are common in fibromyalgia patients and may make symptoms worse. Symptoms may tend to come and go. There can be periods when the symptoms are constant (flares), that may be followed by periods when the symptoms are absent (remissions). Some fibromyalgia patients find that cold, damp weather, emotional stress, overexertion, and other factors exacerbate their symptoms.

A more specific embodiment of the present invention relates to the above method wherein the disorder or condition that is being treated is selected from major depression, single episode depression, recurrent depression, child abuse induced depression, postpartum depression, dysthymia, cyclothymia and bipolar disorder.

Another more specific embodiment of the present invention relates to the above method wherein the disorder or condition that is being treated is selected from schizophrenia, schizoaffective disorder, delusional disorder, substance-induced psychotic disorder, brief psychotic disorder, shared psychotic disorder, psychotic disorder due to a general medical condition, and schizophreniform disorder.

Another more specific embodiment of the present invention relates to the above method wherein the disorder or condition that is being treated is selected from autism, pervasive development disorder, and attention deficit hyperactivity disorder.

Another more specific embodiment of the present invention relates to the above method wherein the disorder or condition that is being treated is selected from generalized anxiety disorder, panic disorder, obsessive-compulsive disorder, post-traumatic stress disorder, and phobias, including social phobia, agoraphobia, and specific phobias.

Another more specific embodiment of the present invention relates to the above method wherein the disorder or condition that is being treated is selected from movement disorders such as akinesias, dyskinesias, including familial paroxysmal dyskinesias, spasticities, Tourette's syndrome, Scott syndrome, palsys (e.g., Bell's palsy, cerebral palsy, birth palsy, brachial palsy, wasting palsy, ischemic palsy, progressive bulbar palsy and other palsys), and akinetic-rigid syndrome; and extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremor.

Another more specific embodiment of the present invention relates to the above method wherein the disorder or condition that is being treated is pain. Pain refers to acute as well as chronic pain. Acute pain is usually short-lived and is associated with hyperactivity of the sympathetic nervous system. Examples are postoperative pain and allodynia. Chronic pain is usually defined as pain persisting from 3 to 6 months and includes somatogenic pain and psychogenic pain. Other pain is nociceptive.

Examples of the types of pain that can be treated with the compounds of formula I of the present invention and their pharmaceutically acceptable salts include pain resulting from soft tissue and peripheral damage, such as acute trauma, pain associated with osteoarthritis and rheumatoid arthritis, musculo-skeletal pain, such as pain experienced after trauma; spinal pain, dental pain, myofascial pain syndromes, episiotomy pain, and pain resulting from burns; deep and visceral pain, such as heart pain, muscle pain, eye pain, orofacial pain, for example, odontalgia, abdominal pain, gynaecological pain, for example, dysmenorrhoea, labour pain and pain associated with endometriosis; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, trigeminal neuralgia, neuropathic lower back pain, HIV related neuropathic pain, cancer related neuropathic pain, diabetic neuropathic pain, and arachnoiditis; neuropathic and non-neuropathic pain associated with carcinoma, often referred to as cancer pain; central nervous system pain, such as pain due to spinal cord or brain stem damage; lower back pain; sciatica; phantom limb pain, headache, including migraine and other vascular headaches, acute or chronic tension headache, cluster headache, temperomandibular pain and maxillary sinus pain; pain resulting from ankylosing spondylitis and gout; pain caused by increased bladder contractions; post operative pain; scar pain; and chronic non-neuropathic pain such as pain associated with fibromyalgia, HIV, rheumatoid and osteoarthritis, arthralgia and myalgia, sprains, strains and trauma such as broken bones; and post surgical pain.

Still other pain is caused by injury or infection of peripheral sensory nerves. It includes, but is not limited to pain from peripheral nerve trauma, herpes virus infection, diabetes mellitus, fibromyalgia, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Neuropathic pain includes, but is not limited to pain caused by nerve injury such as, for example, the pain diabetics suffer from.

Psychogenic pain is that which occurs without an organic origin such as low back pain, atypical facial pain, and chronic headache.

Other types of pain are: inflammatory pain, osteoarthritic pain, trigeminal neuralgia, cancer pain, diabetic neuropathy, restless leg syndrome, acute herpetic and postherpetic neuralgia, causalgia, brachial plexus avulsion, occipital neuralgia, gout, phantom limb, burn, and other forms of neuralgia, neuropathic and idiopathic pain syndrome.

Another more specific embodiment of the present invention relates to the above method wherein the disorder or condition that is being treated is selected from delirium, dementia, and amnestic and other cognitive or neurodegenerative disorders, such as Parkinson's disease (PD), Huntington's disease (HD), Alzheimer's disease, senile dementia, dementia of the Alzheimer's type, memory disorders, loss of executive function, vascular dementia, and other dementias, for example, due to HIV disease, head trauma, Parkinson's disease, Huntington's disease, Pick's disease, Creutzfeldt-Jakob disease, or due to multiple etiologies.

The compounds of the present invention can be co-administered to a subject. The term "co-administered" means the administration of two or more different pharmaceutical agents or treatments (e.g., radiation treatment) that are administered to a subject by combination in the same pharmaceutical composition or separate pharmaceutical compositions. Thus co-administration involves administration at the same time of a single pharmaceutical composition comprising two or more pharmaceutical agents or administration of two or more different compositions to the same subject at the same or different times. For example, a subject that is administered a first dosage that comprises a compound of the present invention at 8 a.m. and then is administered a second therapeutic agent at 1-12 hours later, e.g., 6 p.m., of that same day has been co-administered with a compound of the present invention and the second therapeutic agent. Alternatively, for example, a subject could be administered with a single dosage comprising a compound of the present invention and a second therapeutic agent at 8 a.m. has been co-administered with a compound of the present invention and the second therapeutic agent.

The compounds of the present invention may further be co-administered for the treatment of fibromyalgia with one or more agents useful for treating one or more indicia of fibromyalgia selected from the group consisting of: non-steroidal anti-inflammatory agents (hereinafter NSAID's) such as piroxicam, loxoprofen, diclofenac, propionic acids such as naproxen, flurbiprofen, fenoprofen, ketoprofen and ibuprofen, ketorolac, nimesulide, acetaminophen, fenamates such as mefenamic acid, indomethacin, sulindac, apazone, pyrazolones such as phenylbutazone, salicylates such as aspirin, COX-2 inhibitors such as CELEBREX® (celecoxib), BEXTRA® (valdecoxib) and etoricoxib: steroids, cortisone, prednisone, muscle relaxants including cyclobenzaprine and tizanidine; hydrocodone, dextropropoxyphene, lidocaine, opioids, morphine, Fentanyl, tramadol, codeine, Paroxetine (PAXIL®), Diazepam, Femoxetine, Carbamazepine, Milnacipran (IXEL®), Vestra®, Venlafaxine (EFFEXOR®), Duloxetine (CYMBALTA®), Topisetron (NAVOBAN®), Interferon alpha (Veldona), Cyclobenzaprine, CPE-215, Sodium oxbate (XYREM®), Celexa™ (citalopram HBr), ZOLOFT® (sertraline HCl), antidepressants, tricyclic antidepressants, Amitryptyline, Fluoxetine (PROZAC®), topiramate, escitalopram, benzodiazepenes including diazepam, bromazepam and tetrazepam, mianserin, clomipramine, imipramine, topiramate, and nortriptyline. The compound of the present invention may also be co-administered with alpha-2-delta ligands. Examples of alpha-2-delta ligands for use with the present invention are those compounds generally or specifically disclosed in U.S. Pat. No. 4,024,175, particularly gabapentin (NEURONTIN®), EP641330, particularly pregabalin (LYRICA®), U.S. Pat. No. 5,563,175, WO9733858, WO9733859, WO9931057, WO9931074, WO9729101, WO02085839, particularly [(1R,5R,6S)-6-(aminomethyl)bicyclo[3.2.0]hept-6-yl]acetic acid, WO9931075, particularly 3-(1-aminomethyl-cyclohexylmethyl)-4H-[1,2,4]oxadiazol-5-one and C-[1-(1H-tetrazol-5-ylmethyl)-cycloheptyl]-methylamine, WO9921824, particularly (3S,4S)-(1-aminomethyl-3,4-dimethyl-cyclopentyl)-acetic acid, WO0190052, WO0128978, particularly (1α,3α,5α)(3-amino-methyl-bicyclo[3.2.0]hept-3-yl)-acetic acid, EP0641330, WO9817627, WO0076958, particularly (3S,5R)-3-aminomethyl-5-methyl-octanoic acid, PCT/IB03/00976, particularly (3S,5R)-3-amino-5-methyl-heptanoic acid, (3S,5R)-3-amino-5-methyl-nonanoic acid and (3S,5R)-3-Amino-5-methyl-octanoic acid, EP1178034, EP1201240, WO9931074, WO03000642, WO0222568, WO0230871, WO0230881, WO02100392, WO02100347, WO0242414, WO0232736 and WO0228881, and pharmaceutically acceptable salts and solvates thereof, all of which are incorporated herein by reference.

For the treatment of depression, anxiety, schizophrenia or any of the other disorders and conditions referred to above in the descriptions of the methods and pharmaceutical compositions of the present invention, the compounds of the present invention can be used in conjunction with one or more other antidepressants or anti-anxiety agents. Examples of classes of antidepressants that can be used in combination with the active compounds of the present invention include norepinephrine reuptake inhibitors, selective serotonin reuptake inhibitors (SRIs), NK-1 receptor antagonists, monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, alpha-2-delta ligands (A2D) (e.g., NEURONTIN®, and LYRICA®, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one and C-[1-(1H-tetrazol-5-ylmethyl)-cycloheptyl]-methylamine, (3S,4S)-(1-aminomethyl-3,4-dimethyl-cyclopentyl)-acetic acid, (1α,3α,5α)(3-amino-methyl-bicyclo[3.2.0]hept-3-yl)-acetic acid, (3S,5R)-3-aminomethyl-5-methyl-octanoic acid, (3S,5R)-3-amino-5-methyl-heptanoic acid, (3S,5R)-3-amino-5-methyl-nonanoic acid and (3S,5R)-3-amino-5-methyl-octanoic acid, etc.)), and atypical antidepressants. Suitable norepinephrine reuptake inhibitors include tertiary amine tricyclics and secondary amine tricyclics. Suitable tertiary amine tricyclics and secondary amine tricyclics include amitriptyline, clomipramine, doxepin, imipramine, trimipramine, dothiepin, butripyline, iprindole, lofepramine, nortriptyline, protriptyline, amoxapine, desipramine and maprotiline. Suitable selective serotonin reuptake inhibitors include fluoxetine, fluvoxamine, paroxetine, citalopram, and sertraline. Examples of monoamine oxidase inhibitors include isocarboxazid, phenelzine, and tranylcyclopramine. Suitable reversible inhibitors of monoamine oxidase include moclobemide. Suitable serotonin and noradrenaline reuptake inhibitors of use in the present invention include venlafaxine and duloxetine. Suitable CRF antagonists include those compounds described in International Patent Application Nos. WO 94/13643, WO 94/13644, WO 94/13661, WO 94/13676 and WO 94/13677. Suitable atypical antidepressants include bupropion, lithium, nefazodone, trazodone and viloxazine. Suitable NK-1 receptor antagonists include those referred to in World Patent Publication WO 01/77100. Suitable A2D ligands include those referred to in World Patent Publications WO 99/21824, WO 01/90052, WO 01/28978, WO 98/17627, WO 00/76958, and WO 03/082807, and specifically NEURONTIN® and LYRICA®.

Suitable classes of anti-anxiety agents that can be used in combination with the active compounds of the present invention include benzodiazepines and serotonin IA (5-HT$_{1A}$) agonists or antagonists, especially 5-HT$_{1A}$ partial agonists, and corticotropin releasing factor (CRF) antagonists. Suitable benzodiazepines include alprazolam, chlordiazepoxide, clonazepam, chlorazepate, diazepam, halazepam, lorazepam, oxazepam, and prazepam. Suitable 5-HT$_{1A}$ receptor agonists or antagonists include buspirone, flesinoxan, gepirone and ipsapirone.

Suitable antipsychotic agents include both conventional and atypical antipsychotics.

Conventional antipsychotics are antagonists of dopamine (D$_2$) receptors. The atypical antipsychotics also have D$_2$ antagonistic properties but possess different binding kinetics to these receptors and activity at other receptors, particularly 5-HT$_{2A}$, 5-HT$_{2C}$ and 5-HT$_{2D}$ (Schmidt B et al, Soc. Neurosci. Abstr. 24:2177, 1998).

The class of atypical antipsychotics includes clozapine (CLOZARIL®), 8-chloro-11-(4-methyl-1-piperazinyl)-5H-dibenzo[b,e][1,4]diazepine (U.S. Pat. No. 3,539,573); risperidone (RISPERDAL®), 3-[2-[4-(6-fluoro-1,2-benzisoxazol-3-yl)piperidino]ethyl]-2-methyl-6,7,8,9-tetrahydro-4H-pyrido-[1,2-a]pyrimidin-4-one (U.S. Pat. No. 4,804,663); olanzapine (ZYPREXA®), 2-methyl-4-(4-methyl-1-piperazinyl)-10H-thieno[2,3-b][1,5]benzodiazepine (U.S. Pat. No. 5,229,382); quetiapine (SEROQUEL®), 5-[2-(4-dibenzo[b,f][1,4]thiazepin-11-yl-1-piperazinyl)ethoxy]

ethanol (U.S. Pat. No. 4,879,288); aripiprazole (ABILIFY®), 7-{4-[4-(2,3-dichlorophenyl)-1-piperazinyl]-butoxy}-3,4-dihydro carbostyril and 7-{4-[4-(2,3-dichlorophenyl)-1-piperazinyl]-butoxy}-3,4-dihydro-2(1H)-quinolinone (U.S. Pat. Nos. 4,734,416 and 5,006,528); sertindole, 1-[2-[4-[5-chloro-1-(4-fluorophenyl)-1H-indol-3-yl]-1-piperidinyl]ethyl]imidazolidin-2-one (U.S. Pat. No. 4,710,500); amisulpride (U.S. Pat. No. 4,410,822); and ziprasidone (GEODON®), 5-[2-[4-(1,2-benzisothiazol-3-yl)piperazin-3-yl]ethyl]-6-chloroindolin-2-one hydrochloride hydrate (U.S. Pat. No. 4,831,031).

EXAMPLES

Example 1

1-(2-fluorophenyl)-3-(piperidin-4-yloxy)-1H-indazole hydrochloride

To a slurry of 2-fluorophenylhydrazine hydrochloride (40.1 g, 246.7 mmol) in 411 ml EtOH was added di-isopropylethylamine (47.27 ml, 271.4 mmol) followed by solid isatoic anhydride (40.0 g, 246.7 mmol). The slurry was heated to reflux. Upon reflux, all the solids went into solution and refluxing was continued for 1.5 hours. The reaction mixture was allowed to cool to room temperature and stood overnight. The solid that precipitated was filtered and washed with EtOH (ethanol). The filtrate was concentrated to dryness and the remaining material was taken up in EtOAc (ethyl acetate), washed with water and dried over $Na_2SO_4$. The EtOAc solution was concentrated and the remaining oil was taken up in a minimal amount of ether. The ether solution was then triturated with heptane. The solid recovered was combined with the above to give 34.89 g of the hydrazide. The hydrazide was slurried into 307 ml of 1M HCl solution. The slurry was cooled to 0° C. and sodium nitrite (19.62 g, 284.4 mmol) in 100 ml water was added. Next 582 ml of EtOH was added and the slurry was refluxed for 2 hours then allowed to stand overnight at room temperature. The resulting slurry was filtered and washed with EtOH. The filtrate was concentrated down to give more solid. After combining with the 1st batch of solid, the material was recrystallized in 95:5 EtOH:i-PrOH (isopropanol) to give 23.45 g of 1-(2-fluoro-phenyl)-1H-indazol-3-ol (Intermediate 1). MS (APCI): 229 (M+1, 100%).

To a solution of t-butyl 4-hydroxy-1-piperidinecarboxylate (0.94 g, 4.66 mmol) and methanesulfonyl chloride (0.43 ml, 5.56 mmol) in 10 ml of anhydrous $CH_2Cl_2$ at 0° C. was added triethylamine (0.71 ml, 5.09 mmol). The colorless solution turned into a white suspension. The reaction mixture was stirred at 0° C. for 2 hours. Ether (50 ml) was added to the white suspension and the precipitates were removed by filtration. The residue was washed twice with 10 ml of ether. The combined filtrate and washings were concentrated on a rotary evaporator. The residue oil was chromatographed on silica gel with 50% EtOAc in hexanes to give 1.06 g of Intermediate 2 (4-methanesulfonyloxy-piperidine-1-carboxylic acid tert-butyl ester) as a white solid. MS (APCI): 224 (100%), 180 (32%).

A mixture of Intermediate 1 (0.41 g, 1.80 mmol), Intermediate 2 (0.53 g, 1.90 mmol) and sodium hydride (60% dispersion in mineral oil, 0.099 g, 2.48 mmol) in 13 ml of anhydrous DMF (dimethylformamide) was stirred at 100° C. for 7 hours. After cooling to room temperature, saturated $NH_4Cl$ solution (40 ml) and water (15 ml) were added to quench the reaction. The mixture was extracted three times with 50 ml of ether. The combined extracts were dried over $MgSO_4$ and then concentrated on a rotary evaporator. The residue oil was chromatographed on silica gel with 20% EtOAc in hexanes to give 0.52 g of Intermediate 3 (4-[1-(2-fluoro-phenyl)-1H-indazol-3-yloxy]-piperidine-1-carboxylic acid tert-butyl ester) as a pale yellow oil. MS (APCI): 412 (M+1, 62%), 356 (46%), 312 (100%).

To a solution of Intermediate 3 (0.52 g, 1.26 mmol) in 4 ml of EtOAc at room temperature was added 4 ml of a 4 M solution of HCl in dioxane. The reaction mixture was stirred at room temperature for 3 hours. The reaction mixture was concentrated on a rotary evaporator. EtOAc (30 ml) was added to dissolve the oily residue. The solution was concentrated again on a rotary evaporator to remove the last trace of dioxane. Methanol (3 ml) was added to re-dissolve the oily residue. Ether (30 ml) was added slowly to the solution. The cloudy solution was concentrated on a rotary evaporator to give solid material. The solid was triturated with 5 ml of 1:1 EtOAc in ether for 15 minutes. An additional 20 ml of ether was added and the precipitates were collected by filtration. After washing twice with 5 ml of ether, the solid was dried at 95° C. under vacuum overnight to give 0.36 g of the title product as a white powder.

Example 2

(S)-(+)-1-(2-fluorophenyl)-3-(morpholin-2-yl-methoxy)-1H-indazole maleate (S)-3-Hydroxymethylmorpholine was prepared according to the procedure described in *J. Med. Chem.* 1998, 41, 1934-1942. Intermediate 5 ((S)-2-Hydroxymethyl-morpholine-4-carboxylic acid tert-butyl ester) was prepared under standard conditions (NaOH, di-tert-butyl dicarbonate, $H_2O$/THF, 0° C.). MP=67-68° C.

Intermediate 6 (2-methanesulfonyloxymethyl-morpholine-4-carboxylic acid tert-butyl ester) was prepared according to the procedure described above for the preparation of Intermediate 2 using Intermediate 5 as the starting material. $[\alpha]_D^{24}$=+18.4° ($CHCl_3$, c=8.9), MS (APCI): 240 (95%), 196 (100%).

Intermediate 7 ((S)-2-[1-(2-fluoro-phenyl)-1H-indazol-3-yloxymethyl]-morpholine-4-carboxylic acid tert-butyl ester) was prepared according to the procedure described above for the preparation of Intermediate 3 using Intermediate 6 as the starting material and stirred at 100° C. for 3.5 hours. $[\alpha]_D^{24}$=+16.0° ($CHCl_3$, c=5.0), MS (APCI): 410 (M+H, 80%), 310 (100%).

To a solution of the Intermediate 7 (0.86 g, 2.00 mmol) in 6 ml of EtOAc was added 6 ml of a 4 M solution of HCl in dioxane at room temperature. The reaction mixture was stirred at room temperature for 2.5 hours. The reaction mixture was concentrated on a rotary evaporator. The residue was loaded onto a 5% HOAc in MeOH solution pre-washed Varian Mega Bond Elut SCX column. The column was washed four times with 50 ml of MeOH to remove HCl. The amine was eluted out with 1N $NH_3$ in MeOH solution (3×40 ml) to give 0.52 g of the free base as a colorless oil. The oil was then dissolved in 75 ml of ether. A solution of maleic acid (0.187 g, 1.61 mmol) in 2 ml of MeOH was added slowly into the amine solution at room temperature. A white precipitate was formed and the suspension was stirred at room temperature for 10 minutes. The white solid was collected by filtration. It was washed twice with 10 ml of ether and then dried in vacuum overnight at 100° C. to give 0.661 g of the title product as a white powder.

Example 3

(S)-(+)1-(2,4difluorophenyl)-3-(morpholin-2-yl-methoxy)-1H-indazole maleate

To a slurry of 2,4-difluorophenyl hydrazine hydrochloride (15.2 g) in 140 ml of EtOH at room temperature was added 15.64 ml of di-isopropylethylamine. The mixture was stirred for 20 minutes until almost all was in solution, then isatoic anhydride (14.0 g) was added. The mixture was heated to reflux at which point a solution formed. After 1.5 hours, the reaction was cooled to room temperature and let stand overnight. The solid that precipitated was filtered off, washed with EtOH, and dried to give 9.36 g (44% yield) of 2-aminobenzoic acid N'-(2,4-difluoro-phenyl)-hydrazide (Intermediate 17): MS (APCI): (M+1)=264, (M−1)=262.

Intermediate 17 (9.80 g, 37.3 mmol) was stirred in 82 ml of 1M HCl (aq), cooled to 0° C. and a solution of sodium nitrite (5.1 g, 74 mmol) in 18 ml of water was added cautiously via pipet. A thick suspension formed. 106 ml of EtOH was added and the reaction was heated to reflux. A thick foam formed which was not stirring. The reaction was cooled to room temperature, diluted with 100 ml of 1:1 EtOH:$H_2O$, good stirring was resumed, and the mixture was heated to reflux for 2 hours. The reaction was cooled to room temperature overnight, the precipitate was filtered off, washed with $H_2O$ and dried in the Buchner funnel to give 7.55 g of a putty colored solid, 1-(2,4-difluoro-phenyl)-1H-indazol-3-ol (Intermediate 18) as the product: MS (APCI): (M+1)=247.

Intermediate 19 (2-[1-(2,4-difluoro-phenyl)-1H-indazol-3-yloxymethyl]-morpholine-4-carboxylic acid tert-butyl ester) was prepared according to the procedure described above for the preparation of Intermediate 3 using Intermediate 6 and Intermediate 18 as the starting materials and stirred at 100° C. for 3 hours. $[\alpha]_D^{24}$=+19.4° ($CHCl_3$, c=5.4), MS (APCI): 446 (M+H, 100%), 346 (90%).

The title product was prepared from Intermediate 19 according to the procedure described above for the preparation of Example 2.

Examples 4-13 were synthesized in a manner similar to that described for Example 1.

Example 14

(R)-1-phenyl-3-(pyrrolidin-3-ylmethoxy)-1H-indazole hydrochloride

To a slurry of isatoic anhydride (50.0 g, 308.3 mmol) in 514 ml EtOH, was added phenylhydrazine (30.33 ml, 308.3 mmol) and the slurry was heated to reflux. Upon reflux, all of the solid went into solution and the refluxing was continued for 1.5 hours. The reaction solution was allowed to cool to room temperature and stand overnight. The solid that precipitated was filtered off and washed with EtOH to give 46.55 g (66% yield) of a white solid as the desired hydrazide. The hydrazide (46.55 g, 204.8 mmol) was slurried into 442.3 ml 1M HCl solution. The slurry was cooled to 0° C. and sodium nitrite (28.26 g, 409.6 mmol) in 100 ml water was added. Next 582 ml EtOH was added and the slurry was heated to reflux for 2 hours, then cooled to room temperature and allowed to stand overnight. The resulting slurry was filtered to give 15 g of yellow solid. The filtrate volume was reduced and more solid was recovered. The solids were combined and recrystallized from 95:5 EtOH:iPrOH to afford 26.50 g (61%) of light yellow solid as Intermediate 28 (1-phenyl-1H-indazol-3-ol): MP=209-211° C.

Intermediate 29 ((R)-3-(1-phenyl-1H-indazol-3-yloxymethyl)-pyrrolidine-1-carboxylic acid tert-butyl ester) was prepared following the procedure described above for the preparation of Intermediate 3 using Intermediate 28 (0.250 g, 1.19 mmol) and (R)-3-methanesulfonyloxymethyl-pyrrolidine-1-carboxylic acid tert-butyl ester (0.370 g, 1.30 mmol, prepared according to *J. Med. Chem.* 1999, 42, 677) as the starting materials and 1.70 mmol of 95% NaH, heating at 100° C. for 18 hours, then adding 1.70 mmol of 60% NaH and heating at 100° C. for 20 hours. The residue oil was chromatographed on silica gel with 10% acetone in hexanes to give 0.275 g of Intermediate 29 as a clear oil.

MS(M+1)=394, 294 (M-BOC).

Intermediate 29 (0.275 g, 0.699 mmol) was dissolved in 2.3 ml EtOAc and 2.3 ml HCl (4M in dioxane) was added at room temperature. After stirring overnight, the solvent was evaporated. The residue was treated with ~30 ml of EtOAc and then concentrated. This was repeated to remove all the dioxane and HCl. The resultant white solid was triturated with ~20 ml of 1:2 EtOAc:ether, filtered, washed twice with 5 ml of ml of ether and dried in a vacuum oven at 60° C. overnight to afford the title product as a light tan powder (0.192 g, 83% yield):

Examples 15-26 were synthesized in a manner similar to that described for Example 14.

Example 27

1-(2,5-difluoro-phenyl)-3-(piperidin-4-yloxy)-1H-indazole hydrochloride

Intermediate 33 (1-(2,5-Difluoro-phenyl)-1H-indazol-3-ol) was prepared according to the procedure above for the preparation of Intermediate 28 using 2,5-difluorophenyl hydrazine (15.1 g, 105 mmol) and isatoic anhydride (17.0 g, 101 mmol) as starting materials and heating the reaction at reflux for 3.5 hours. The hydrazide was isolated as a light sand colored solid (15.6 g, 59% yield): MS (APCI): (M+1)=264, (M−1)=262. Following the same procedure, the hydrazide (15.6 g, 59.3 mmol) was converted to the Intermediate 33 (12.89 g, 88% yield) as a putty colored solid: MS (APCI): (M+1)=247, (M−1)=245.

To a solution of Intermediate 33 (0.300 g, 1.22 mmol) in 12 ml DMF was added 0.600 g (1.80 mmol) of cesium carbonate followed by the Intermediate 2 (0.370 g, 1.30 mmol). The mixture was heated to 80° C. for 24 hours and then cooled to room temperature. The reaction was quenched with saturated $NH_4Cl$ and some extra $H_2O$, then extracted 3 times with $Et_2O$. The extracts were washed once with $H_2O$, then once with brine, dried over $MgSO_4$, and concentrated to 0.515 g yellow oil. The product was purified by flash chromatography (5-10% EtOAc/Hexanes, 90 g silica) to isolate Intermediate 34 (4-[1-(2,5-difluoro-phenyl)-1H-indazol-3-yloxy]-piperidine-1-carboxylic acid tert-butyl ester) as a yellow oil (0.340 g, 65% yield): MS (M+1)=430 (minor), 330 (M-BOC).

Intermediate 34 (0.334 g, 0.778 mmol) was treated with HCl in dioxane/EtOAc according to the procedure for Intermediate 30, with stirring at room temperature for 3.5 hours. After the usual work-up, the solid was triturated with 20 ml of 1:1 EtOAc:ether, filtered, washed twice with 5 ml of ml of ether and dried in a vacuum oven at 60° C. to afford the title product as a white powder (0.240 g, 84% yield): MS (APCI): (M+1)=330.

Examples 28-40 were synthesized in a manner similar to that described for Example 27.

Example 41

1-(4-chloro-phenyl)-3-(piperidin-4-yloxy)-1H-indazole hydrochloride

4-Chlorophenylhydrazine hydrochloride (2.105 g, 14.76 mmol) was suspended in EtOH (25 ml), treated with di-isopropylethylamine (2.253 ml, 12.93 mmol) and stirred for 30 minutes. Isatoic anhydride (1.918 g, 11.76 mmol) was added and the mixture was heated to reflux for 3 hours. The reaction mixture was cooled to room temperature and stirred overnight. The material was concentrated to dryness and the resulting residue was partitioned between EtOAc (~25 ml) and 50% saturated NaCl (3×30 ml). The organic layer (also containing a small amount of emulsion which would not dissipate over 3 extractions) was dried over $MgSO_4$ and concentrated to an orange solid. The material was triturated with EtOAc, filtered and rinsed with additional EtOAc. The filtrate was concentrated to dryness and treated with DCM (dichloromethane). The mixture was stirred overnight. The mixture was filtered, rinsed with DCM and the solid dried to provide 1.538 g (50%) of 2-amino-benzoic acid N'-(4-chloro-phenyl)-hydrazide (Intermediate 40) as a mauve-colored solid. MS (APCI): (M+1)=262.1, (M−1)=260.0.

Intermediate 40 (1.538 g, 5.877 mmol) was suspended in 1M HCl (12 ml), cooled to 0° C. and treated dropwise with a solution of sodium nitrite (811 mg, 11.75 mmol) in water (5 ml). The mixture was stirred for 10 minutes at 0° C., diluted with 1:1 EtOH/$H_2O$ (25 ml), heated to reflux for 3 hours, then cooled to room temperature and stirred for about 1 hour. The mixture was filtered and rinsed with water. The isolated solid was treated with $Et_2O$ and EtOAc, followed by 1N NaOH. A large amount of solid remained that would not dissolve. The mixture was poured into a separatory funnel and allowed to separate. All of the solid partitioned into the organic layer, so the aqueous layer was drained (designated aqueous layer 1). The organic layer was then treated with additional 1N NaOH. The solid then partitioned into the aqueous layer and this too was drained (with solid—designated aqueous layer 2). Both of the aqueous layers were treated with concentrated HCl until approximately neutral. Aqueous layer 1 formed a nice solid that was filtered, rinsed with water and dried. The solid was dried in a vacuum oven at 50° C. for 2 days to afford 141 mg (9.8%) of 1-(4-chloro-phenyl)-1H-indazol-3-ol (Intermediate 41) as a tan solid. Aqueous layer 2, however, formed large clumps of emulsion-looking solids. This material was allowed to stand at room temperature for 2 days then stirred vigorously until all of the clumps broke up. Ethyl acetate was then added, the mixture was made basic with 1 N NaOH, and the solid was filtered and washed with EtOAc. The solid was dried in a vacuum oven at 50° C. over three days to afford 522 mg (36%) of Intermediate 41 as a white solid. MS (APCI): (M+1)=245.1, (M−1)=243.0.

Intermediate 41 (300 mg, 1.226 mmol) was combined with dry DMF (10 ml), treated with PS-BEMP resin (2-tert-butyl-imino-2-diethylamino-1,3-dimethyl-perhydro1,3,2-diazaphosphorine on polystyrene), (1.115 g) and stirred for 30 minutes. A solution of Intermediate 2 (377 mg, 1.349 mmol) in dry DMF (5 ml) was added slowly dropwise, and the mixture was heated to 70° C. overnight. The mixture was filtered to remove the resin, and the resin was washed with hot DMF. The filtrate was concentrated in vacuo. The crude material was chromatographed over 20 g silica gel, eluting with 8% EtOAc/Hexanes. The appropriate fractions were combined and concentrated to afford 212 mg (40%) of 4-[1-(4-chloro-phenyl)-1H-indazol-3-yloxy]-piperidine-1-carboxylic acid tert-butyl ester (Intermediate 42) as a colorless glass. MS (APCI): (M−1)=426.2.

Intermediate 42 (212 mg, 0.495 mmol) was dissolved in EtOAc (2 ml), treated with 4M HCl in dioxane (1.61 ml, 6.44 mmol) and stirred overnight at room temperature. The mixture was concentrated in vacuo, treated with EtOAc and concentrated again. This process was repeated 5 times. The resulting white solid was triturated with $Et_2O$, filtered, rinsed with $Et_2O$ and dried in a vacuum oven at 50° C. to afford 155 mg (86%) of the title product—1-(4-chloro-phenyl)-3-(piperidin-4-yloxy)-1H-indazole hydrochloride as a white solid.

Examples 42-43 were synthesized in a manner similar to that described for Example 41, except di-isopropylethylamine was replaced with triethylamine and ethanol was replaced with tetrahydrofuran (THF).

Example 44

(S)-(−)-3-(piperidin-3-ylmethoxy)-1-pyridin-2-yl-1H-indazole maleate

A mixture of isatoic anhydride (3.51 g, 2.15 mmol) and 2-hydrazinopyridine (2.40 g, 2.20 mmol) in 35 ml of EtOH was refluxed for 17 hours. After refluxing for 15 minutes, the suspension turned into a brown solution and gas evolution was observed. At the end of the 17 hour period, the reaction mixture was cooled to room temperature and the brown solution was concentrated on a rotary evaporator. The residue was chromatographed on silica gel with 65% EtOAc in hexanes. The fractions containing the product were collected and concentrated. The solid was triturated with ether (100 ml) for 15 minutes and collected by filtration. It was air-dried to give 2.68 g of 2-amino-benzoic acid N'-pyridin-2-yl-hydrazide (Intermediate 9) as a white solid. MS (APCI): 229 (M+1, 100%).

To a solution of Intermediate 9 (1.38 g, 6.04 mmol) in 21 ml of 1M HCl solution at 0° C. was added a solution of sodium nitrite (0.90 g, 1.31 mmol) in 5 ml water. A white precipitate was obtained on addition of the sodium nitrite solution. EtOH (30 ml) was then added and the mixture was refluxed for 2 hours. The white suspension turned into a yellow solution during reflux. After 2 hours, the mixture was cooled to room temperature. The orange color solution turned into an orange color suspension. The mixture was concentrated on a rotary evaporator. The solid residue was dissolved in a mixture of EtOAc (70 ml), THF (30 ml), saturated $NaHCO_3$ solution (80 ml) and water (40 ml). The mixture was stirred at room temperature for 15 minutes. The organic layer was collected and the aqueous layer was extracted twice with 70 ml of EtOAc. The combined organic layers were dried over $MgSO_4$ and concentrated to give 1.05 g of 1-pyridin-2-yl-1H-indazol-3-ol (Intermediate 10) as a pale yellow solid. MS (APCI): 212 (M+1, 100%).

Intermediate 11 ((S)-3-methanesulfonyloxymethyl-piperidine-1-carboxylic acid tert-butyl ester) was prepared according to the procedure described above for the preparation of Intermediate 2 using (S)-3-hydroxymethyl-1-N-Boc-piperidine (Astatech) as the starting material. (Boc=tert-butyloxycarbonyl). $[\alpha]_D^{24}$=+18.8° ($CHCl_3$, c=4.9), MS (APCI): 238 (100%), 194 (73%).

Intermediate 12 ((S)-3-(1-pyridin-2-yl-1H-indazol-3-yloxymethyl)-piperidine-1-carboxylic acid tert-butyl ester) was prepared according to the procedure described above for the preparation of Intermediate 3 using Intermediate 11 and Intermediate 10 as the starting materials and stirred at 100° C.

for 1.5 hours. $[\alpha]_D^{24}$=+21.8° (CHCl$_3$, c=5.5), MS (APCI): 409 (M+H, 100%), 309 (100%).

The title product was prepared from Intermediate 12 according to the procedure described above for the preparation of Example 2.

Example 45

(S)-(−)-5-fluoro-1-(2-fluorophenyl)-3-(piperidin-3-ylmethoxy)-1H-indazole maleate To a solution of 2-amino-5-fluorobenzoic acid (15.34 g, 98.86 mmol) and sodium carbonate (10.66 g, 100.6 mmol) in 260 ml of water at room temperature was added a 1.93 M phosgene solution in toluene (63 ml, 121.6 mmol) slowly with vigorous stirring. A yellow precipitate was formed during the addition. The mixture was stirred at room temperature for 30 minutes after the addition of phosgene was completed. The precipitate was collected by filtration and washed four times with 100 ml of water. The solid was air-dried for 30 minutes then it was washed with a 1:1 mixture of ether in hexanes (3×40 ml). The solid was again air-dried to give 17.36 g of Intermediate 21 (6-fluoro-1H-benzo[d][1,3]oxazine-2,4-dione) as a yellow solid. $^1$H NMR (400 MHz, DMSO-d$_6$) δ ppm 7.16 (dd, J=8.78, 3.90 Hz, 1H) 7.62 (dd, J=8.66, 3.29 Hz, 1H) 7.66 (m, 1H) 11.75 (s, 1H).

A mixture of Intermediate 21 (8.42 g, 46.48 mmol) and 2-fluorophenylhydrazine (6.00 g, 47.57 mmol) in 100 ml of anhydrous THF was refluxed for 4 hours. The reaction mixture turned gradually from a yellow suspension into an orange colored solution. At the end of the 4-hour period, the reaction mixture was cooled to room temperature and the mixture was concentrated on a rotary evaporator. The residue was triturated with a 1:1 mixture of ether in hexanes (2×15 ml) for 15 minutes and the solid was collected by filtration. It was air-dried to give 7.62 g of Intermediate 22 (2-amino-5-fluorobenzoic acid N'-(2-fluoro-phenyl)-hydrazide) as a white solid. MS (APCI): 264 (M+1, 100%).

To a suspension of Intermediate 22 (7.61 g, 28.92 mmol) in 65 ml of a 1M HCl solution at 0° C. was added a solution of sodium nitrite (4.20 g, 60.93 mmol) in 17 ml of water. Next EtOH (95 ml) was added and the slurry was refluxed for 2 hours. The reaction mixture was cooled to room temperature and then concentrated on a rotary evaporator. Saturated NaCl solution (40 ml), water (30 ml), EtOAc (150 ml) and THF (100 ml) were added to dissolve the solid material. The organic layer was collected and the aqueous layer was extracted with EtOAc (100 ml). The combined organic layers were dried over MgSO$_4$ and then concentrated on a rotary evaporator. The residue was triturated with ether (40 ml) and the solid was collected by filtration. The solid was washed again with a 1:1 mixture of ether in hexanes (2×10 ml) and air-dried to give 5.66 g of Intermediate 23 (5-fluoro-1-(2-fluoro-phenyl)-1H-indazol-3-ol) as an off-white powder. MS (APCI): 247 (M+1, 100%), 248 (27%).

Intermediate 24 ((S)-3-[5-fluoro-1-(2-fluoro-phenyl)-1H-indazol-3-yloxymethyl]-piperidine-1-carboxylic acid tert-butyl ester) was prepared according to the procedure described above for the preparation of Intermediate 3 using Intermediate 11 and Intermediate 23 as the starting materials and stirred at 100° C. for 4 hours.

The title product was prepared from the Intermediate 24 according to the procedure described above for the preparation of Example 2.

Example 46

(S)-(+)-5-fluoro-1-(2-fluorophenyl)-3-(morpholin-2-ylmethoxy)-1H-indazole maleate Intermediate 26 ((S)-2-[5-fluoro-1-(2-fluoro-phenyl)-1H-indazol-3-yloxymethyl]-morpholine-4-carboxylic acid tert-butyl ester) was prepared according to the procedure described above for the preparation of Intermediate 3 using Intermediate 6 and Intermediate 23 as the starting materials and stirred at 100° C. for 3 hours. $[\alpha]_D^{24}$=+18.2° (CHCl$_3$, c=5.1), MS (APCI): 446 (M+H, 86%), 447 (22%), 390 (21%), 346 (100%), 347 (20%).

The title product was prepared from Intermediate 26 according to the procedure described above for the preparation of Example 2.

Examples 47-49 were synthesized in a manner similar to that described for Example 45.

Example 50 was synthesized in a manner similar to that described for Example 45, except CDI (1,1'-Carbonyldiimidazole) was used in place of phosgene.

Example 51

5-fluoro-1-(2-fluoro-phenyl)-3-(piperidin-4-yloxy)-1H-indazole hydrochloride

Intermediate 23 (1.00 g, 4.10 mmol) was dissolved in 41 ml CH$_3$CN and 10 ml DMF. To the solution at 50° C. was added 2.0 g of cesium carbonate (6.10 mmol). After 10 minutes, Intermediate 2 (1.14 g, 4.06 mmol) was added and the mixture was heated to 80° C. After 22 hours, the reaction was cooled to room temperature, quenched with saturated NH$_4$Cl and some extra H$_2$O, then extracted three times with Et$_2$O. The extracts were washed once with H$_2$O, then once with brine, dried over MgSO$_4$, and concentrated to 2.61 g yellow oil. The crude product was purified by flash chromatography (1×10-20% EtOAc/hexanes, 1×10% EtOAc/hexanes) to isolate Intermediate 31 (4-[5-fluoro-1-(2-fluoro-phenyl)-1H-indazol-3-yloxy]-piperidine-1-carboxylic acid tert-butyl ester) as a yellow oil (1.13 g, 65%): MS (APCI): (M+1)=430, 330 (M-BOC).

Intermediate 31 (1.13 g, 2.63 mmol) was treated with HCl in dioxane/EtOAc according to the procedure for Example 14, with stirring at room temperature overnight. After the usual work-up, the solid was triturated with 40 ml Et$_2$O, filtered, and washed with 2 more portions of Et$_2$O to give the title product as a white solid (0.721 g, 75% yield): MS(M+1)=330.

Examples 56-57 were synthesized in a manner similar to that described for Example 51.

Example 52

5-fluoro-1-(2-fluoro-phenyl)-3-(1-methyl-piperidin-3-ylmethoxy)-1H-indazole hydrogen chloride To a room temperature solution of piperidine-1,3-dicarboxylic acid-1-tert-butyl ester (5.00 g, 21.81 mmol) in 20% MeOH/toluene (100 ml) was added 14.18 ml of (trimethylsilyl)diazomethane (2.0 M, 28.35 mmol) dropwise and the reaction was monitored by TLC until completion and then concentrated under reduced pressure to yield 4.44 g (83.7%) of piperidine-1,3-dicarboxylic acid 1-tert-butyl ester-3-methyl ester (Intermediate 53). $^1$H NMR (400 MHz, CDCl$_3$) δ ppm 1.4 (s, 9H), 1.6 (d, J=3.4 Hz, 1H), 1.6 (m, 1H), 1.7 (m, 1H), 2.0 (m, 1H), 2.4 (m, 1H), 2.8 (m, 1H), 3.0 (s, 1H), 3.7 (s, 3H), 3.9 (d, J=13.2 Hz, 1H), 4.1 (s, 1H).

To a −78 °C. stirred solution of Intermediate 53 (2.22 g, 9.13 mmol) in dry THF (30 ml) was added NaHMDS (sodium hexamethyldisilazane) (1.0 M in THF, 10.03 mmol) dropwise. The reaction was stirred at this temperature for 30 minutes and then iodomethane (0.682 ml, 10.95 mmol) was added dropwise. The reaction was allowed to warm to room temperature overnight with good stirring. The reaction was cooled and then quenched with saturated $NH_4Cl$. The layers were separated and the aqueous layer was extracted three times with 20 ml of EtOAc and the organic extracts were combined. The organic phase was dried over $Na_2SO_4$, filtered and concentrated under reduced pressure. The oil was purified by silica chromatography using hexanes/EtOAc (0→15%) to yield 2.25 g (95.8%) of 3-methyl-piperidine-1,3-dicarboxylic acid 1-tert-butyl ester 3-methyl ester (Intermediate 54). $^1$H NMR (400 MHz, $CDCl_3$) δ ppm 1.0 (s, 3H), 1.3 (s, 9H), 1.4 (m, 2H), 1.9 (m, 2H), 3.0 (d, J=13.2 Hz, 1H), 3.1 (m, 1H), 3.3 (m, 1H), 3.5 (s, 3H), 3.7 (d, J=13.4 Hz, 1H).

To a 0° C. stirred solution of Intermediate 54 (1.17 g, 4.56 mmol) in dry THF (20 ml) was added $LiAlH_4$ (1.0 M in THF, 9.11 ml, 9.11 mmol) dropwise and the reaction was allowed to warm to room temperature. Upon completion as indicated by TLC, the reaction was carefully quenched with saturated $NH_4Cl$ and EtOAc was added. The layers were separated, the aqueous layer was extracted with EtOAc (3×15 ml) and the organic extracts were combined. The organic phase was dried over $Na_2SO_4$, filtered and concentrated under reduced pressure to yield 0.844 g (42.1%) of 3-hydroxymethyl-3-methyl-piperidine-1-carboxylic acid tert-butyl ester (Intermediate 55). $^1$H NMR (400 MHz, $CDCl_3$) δ ppm 0.9 (s, 3H), 1.3 (m, 2H), 1.5 (s, 9H), 1.5 (m, 3H), 2.9 (s, 1H), 3.1 (s, 1H), 3.5 (d, J=11.5 Hz, 1H), 3.8 (m, 2H).

To a 0° C. stirred solution of Intermediate 55 (0.844 g, 3.68 mmol) in dry $CH_2Cl_2$ (25 ml) was added $Et_3N$ (0.513 ml, 3.682 mmol) and the reaction was stirred for 15 minutes. Methansulfonyl chloride (0.285 ml, 3.682 mmol) was added dropwise and the reaction was allowed to warm to room temperature overnight with good stirring. The reaction was complete by TLC, and $Et_2O$ (100 ml) was added. The mixture was filtered and the filter caked was washed with additional $Et_2O$. The filtrate was then concentrated under reduced pressure. The residue was chromatographed with hexanes/EtOAc (0→25%) to yield 1.05 g (93.1%) of 3-methanesulfonylmethyl-3-methyl-piperidine-1-carboxylic acid tert-butyl ester (Intermediate 56). $^1$H NMR (400 MHz, $CDCl_3$) δ ppm 1.0 (s, 3H), 1.4 (m, 1H), 1.4 (s, 9H), 1.6 (m, 3H), 3.0 (s, 3H), 3.2 (s, 1H), 3.5 (s, 2H), 4.0 (d, J=2.4 Hz, 2H).

To Intermediate 23 (0.300 g, 1.22 mmol) in dry DMF (10 ml) was added $Cs_2CO_3$ (0.596 g, 1.83 mmol) and the mixture was stirred for 30 minutes. Intermediate 56 (0.412 g, 1.34 mmol) was added and the reaction was heated to 80° C. overnight with good stirring. The reaction was not complete by HPLC (81% conversion), however, the heat was turned off and the reaction was allowed to cool to room temperature. The reaction was quenched with saturated $NH_4Cl$ followed by addition of small amount of $H_2O$ and then poured into $Et_2O$. The layers were separated and the aqueous phase was extracted with $Et_2O$ (3×15 ml). The organic extracts were combined, dried over $Na_2SO_4$, filtered and concentrated under reduced pressure. The oil was purified by silica chromatography using hexanes/EtOAc (0→10%) to yield 0.127 g (22.8%) of 3-[5-fluoro-1-(2-fluoro-phenyl)-1H-indazol-3-yloxymethyl]-3-methyl-piperidine-1-carboxylic acid tert-butyl ester (Intermediate 57). MS (APCI): (M+1)=458. $^1$H NMR (400 MHz, $CDCl_3$) δ ppm 1.1 (s, 3H), 1.4 (s, 9H), 1.5 (m, 1H) 1.6 (m, 2H), 1.7 (m, 1H), 3.3 (s, 1H), 3.5 (m, 3H), 4.2 (d, J=30.0 Hz, 2H), 7.2 (m, 2H), 7.3 (s, 1H), 7.3 (s, 1H), 7.3 (m, 2H), 7.6 (m, 1H).

To a room temperature stirred solution of Intermediate 57 (0.127 g, 0.278 mmol) in EtOAc (0.925 ml) was added 0.902 ml of a 4.0 M HCl solution in dioxane. The reaction was allowed to stir overnight at room temperature. Upon completion as indicated by HPLC, the reaction was concentrated under reduced pressure. EtOAc was added to the solid and then concentrated down under reduced pressure. This process was repeated five times. The solid was triturated with EtOAc/$Et_2O$ (2:1), the solid was filtered and then washed with $Et_2O$ (2×15 ml). The solid was placed in a drying oven under reduced pressure to yield 0.089 g (81.7%) of the title product.

Example 53

1-(2-fluoro-phenyl)-3-(3-methyl-piperidin-3-yl-methoxy)-1H-indazole hydrogen chloride The title product was synthesized in the same manner as Example 52 from Intermediate 1 to yield 0.121 g (76.1%) of product.

Example 54

5-fluoro-1-(2-fluoro-phenyl)-3-(4-methyl-piperdin-4-ylmethoxy)-1H-indazole hydrogen chloride The compound was synthesized in the same manner as Example 52 from 5-fluoro-1-(2-fluoro-phenyl)-1H-indazol-3-ol (Intermediate 23) and 4-methanesulfonyloxymethyl-4-methyl-piperidine-1-carboxylic acid tert-butyl ester, synthesized from piperidine-1,4-dicarboxylic acid mono-tert-butyl ester in the same manner as Intermediate 56, to yield 0.068 g (50.3%) of the title product.

Example 55

(R)-5-fluoro-1-(2-fluoro-phenyl)-3-(piperidin-3-ylmethoxy)-1H-indazole maleate

3-[5-fluoro-1-(2-fluoro-phenyl)-1H-indazol-3-yloxymethyl]-piperidine-1-carboxylic acid tert-butyl ester was prepared according to the procedure for Intermediate 57 from Intermediate 23 (0.500 g, 2.03 mmol) and (R)-3-methanesulfonyloxymethyl-piperidine-1-carboxylic acid tert-butyl ester (0.655 g, 2.23 mmol). A room temperature stirred solution of carbamate in EtOAc (5.43 ml) was treated with 5.30 ml of a 4.0 M HCl solution in dioxane. The reaction was allowed to stir overnight at room temperature and was concentrated under reduced pressure, triturated with EtOAc and again concentrated under reduced pressure. This process was repeated three times. Recrystallization of the foam was attempted from hexanes/EtOAc and acetone/hexanes without success. The free base was formed by adding Dowex 550A (OH) Anion Exchange Resin to a stirred solution of the salt in MeOH (10 ml). The mixture was stirred for 30 minutes, filtered and the beads washed three times with 20 of methanol. The organic phase was concentrated under reduced pressure to yield 0.3628 g of the free base as a yellow oil. To a stirred solution of the oil in EtOAc (10 ml) was added maleic acid (0.111 g, 1.0 equivalents). A solid precipitated out and the mixture was concentrated under reduced pressure. The solid was triturated with hexanes/$Et_2O$, filtered and washed with $Et_2O$. The white solid was dried in the oven under reduced pressure at 80° C. overnight to yield 0.390 g (69.6%) of the title maleate salt.

Example 58

5-chloro-1-(2,5-difluoro-phenyl)-3-(piperidin-4-yloxy)-1H-indazole hydrochloride

A solution of 2-amino-5-chloro-benzoic acid (3.0 g, 17.0 mmol) and (2,5-difluoro-phenyl)-hydrazine hydrochloride (3.2 g, 17.5 mmol) in dry THF (tetrahydrofuran) (20 ml) was treated with HOBT (1-hydroxybenzotriazole hydrate) (5.4 g, 35.0 mmol). The resulting mixture was cooled to about −12° C. N-Me-morpholine (3.7 g, 36.7 mmol) was added and the mixture was stirred for 5 minutes before adding EDAC-HCl (1-[3-(dimethylamino)propyl]-3-ethylcarbodiimide hydrochloride) (3.4 g, 17.5 mmol). The mixture was stirred at −12° C. for 1 hour and then allowed to warm to room temperature and stirred overnight. The reaction was partitioned between EtOAc (50 ml) and water (50 ml). The layers were separated and the organic layer was washed four times with saturated aqueous NaCl, dried over $MgSO_4$, and concentrated in vacuum. The resulting solid was triturated with ether, filtered and dried in the vacuum oven overnight at 70° C. and 15 mm Hg to provide Intermediate 36 (2-amino-5-chloro-benzoic acid N'-(2,5-difluoro-phenyl)-hydrazide) (4.0 g, 77% yield) as a light yellow solid: MS (APCI): (M+1)=298.0.

To a 0° C. solution of Intermediate 36 (3.9 g, 13.0 mmol) in 1M HCl (35 ml) was added slowly a solution of $NaNO_2$ in 10 ml water. The resulting mixture was stirred 10 minutes before diluting with 1:1 EtOH/$H_2O$ (50 ml). The mixture was heated to reflux for 3 hours, cooled to room temperature and let stir 1 hour. The solid was filtered off, washed twice with 20 ml of water, and dried in the vacuum oven overnight at 70° C. (15 mm Hg) to afford Intermediate 37 (5-chloro-1-(2,5-difluoro-phenyl)-1H-indazol-3-ol) (3.7 g, 95% yield) as a brown solid: MS (APCI): (M+1)=281.0.

Intermediate 38 was prepared according to the procedure for Intermediate 34 described above using Intermediate 37 (0.5 g, 1.8 mmol), and Intermediate 2 as starting materials to obtain the desired product, Intermediate 38 (4-[5-chloro-1-(2,5-difluoro-phenyl)-1H-indazol-3-yloxy]-piperidine-1-carboxylic acid tert-butyl ester) (0.48 g, 58% yield): MS (APCI): (M+1)=464.0.

Intermediate 39 was prepared according to the procedure for Example 14 described above using Intermediate 38 (0.45 g, 0.97 mmol), as the starting material to obtain desired title product 5-chloro-3-cyclohexyloxy-1-(2,5-difluoro-phenyl)-1H-indazole hydrochloride (0.35 g, 90% yield.

Examples 59-95 were synthesized in a manner similar to that described for Example 58 using the appropriate 2-aminobenzoic acid. Examples 96-97 were synthesized in a manner similar to that described for Example 58, except $CH_3CN$/DMF was used in place of DMF in the reaction of the indazol-3-ol with $Cs_2CO_3$. Example 98 was synthesized in a manner similar to that described for Example 58, except $Cs_2CO_3$ was replaced by NaH. Example 99 was synthesized in a manner similar to that described for Example 58, except pyridylhydrazine was used instead of phenylhydrazine.

Example 100

4-fluoro-1-(2-fluoro-phenyl)-3-(piperidin-4-yloxy)-1H-indazole hydrochloride

2-Amino-6-fluorobenzoic acid (2.00 g, 12.89 mmol) was combined with 2-fluorophenylhydrazine hydrochloride (2.096 g, 12.89 mmol) and HOBt (3.949 g, 25.79 mmol) in dry THF (75 ml) and cooled to about −12° C. N-Methylmorpholine (2.835 ml, 25.79 mmol) was added, the mixture was stirred for 5 minutes, then EDC hydrochloride (2.66 g, 13.88 mmol) was added. The mixture was maintained at a temperature between −14 and −10° C. for 1 hour, then allowed to slowly warm to room temperature and stirred for 18 hours. The mixture was cooled to 0° C., then filtered through CELITE® (diatomaceous earth). The filtrate was diluted with EtOAc, treated with saturated $NaHCO_3$ and the layers separated. The organic layer was washed twice with 50% saturated $NaHCO_3$ and then dried over $MgSO_4$ and concentrated. The resulting solid was triturated with dichloromethane, filtered, rinsed with a very small amount of dichloromethane and dried. The filtrate from the trituration was re-triturated with a small amount of dichloromethane, filtered, rinsed with a tiny amount of dichloromethane and dried. The filtrate was concentrated to dryness, triturated with a small amount of $Et_2O$, filtered, rinsed with a tiny amount of ether and dried. The three solids were combined to afford a total of 2.182 g (64%) of 2-amino-6-fluoro-benzoic acid N'-(2-fluoro-phenyl)-hydrazide (Intermediate 44) as an off-white solid. MS (APCI): (M−1)=262.0.

Intermediate 44 (2.182 g, 8.289 mmol) was suspended in 1M HCl (20 ml), cooled to 0° C. and treated dropwise with a solution of sodium nitrite (1.144 g, 16.58 mmol) in water (7 ml). The mixture was stirred for 10 minutes at 0° C., diluted with 1:1 EtOH/$H_2O$ (30 ml) and heated to reflux for 3 hours, then stirred at room temperature for 18 hours. The solid was filtered, rinsed with water and dried to afford 1.939 g (95%) of 4-fluoro-1-(2-fluoro-phenyl)-1H-indazol-3-ol (Intermediate 45) as a tan solid. MS (APCI): (M+1)=247.1, (M−1)=245.0.

4-[4-Fluoro-1-(2-fluoro-phenyl)-1H-indazol-3-yloxy]-piperidine-1-carboxylic acid tert-butyl ester (Intermediate 46) was prepared as described above for Intermediate 42 using Intermediate 45 (300 mg, 1.218 mmol), PS-BEMP resin (1.108 g) and 4-methanesulfonyloxy-piperidine-1-carboxylic acid tert-butyl ester (Intermediate 2) (374 mg, 1.34 mmol) in DMF (10 ml) to afford 265 mg (51%) of Intermediate 46 as a yellow oil. MS (M+1)=430.2.

The title product was prepared as described above for Example 41 using (Intermediate 46) (265 mg, 0.617 mmol) and 4 M HCl in dioxane (2.00 ml) in EtOAc (2 ml) to afford 202 mg (89%) as a white solid.

Examples 101-103 were synthesized in a manner similar to that described for Example 100.

Example 104

(S)-(−)-1-phenyl-3-(piperidin-3-ylmethoxy)-1H-pyrazolo[3,4-b]pyridine hydrochloride

To a solution of 2-chloronicotinoyl chloride (5.05 g, 2.87 mmol) in 50 ml of anhydrous methylene chloride at 0° C. was added triethylamine (4.5 ml, 3.23 mmol) followed by phenylhydrazine (2.9 ml, 2.95 mmol). The reaction mixture was concentrated on a rotary evaporator. Water (40 ml) was added and the mixture was extracted three times with 80 ml of EtOAc. The combined organic layers were dried over $MgSO_4$ and then concentrated. The solid residue was triturated with a 1:1 mixture of EtOAc and hexanes (60 ml). The solid was collected by filtration and then air-dried after washing twice with 10 ml of ether. The neat solid was then heated to 175° C. for approximately 15 minutes. The solid melted at 175° C. to an orange colored liquid initially and then solidified to give 1.84 g of a brown solid, Intermediate 14 (1-phenyl-1H-pyrazolo[3,4-b]pyridin-3-ol). MS (APCI): 212 (M+1, 100%).

Intermediate 15 (3-(1-phenyl-1H-pyrazolo[3,4-b]pyridin-3-yloxymethyl)-piperidine-1-carboxylic acid tert-butyl ester) was prepared according to the procedure described above for the preparation of Intermediate 3 using Intermediate 11 and Intermediate 14 as the starting materials and stirred at 100° C. for 1.5 hours. $[\alpha]_D^{24}$=+17.4° (CHCl$_3$, c=10.8), MS (APCI): 409 (M+H, 60%), 309 (100%).

To a solution of Intermediate 15 (0.72 g, 1.75 mmol) in 7 ml of EtOAc at room temperature was added a 4M HCl solution in dioxane (5 ml, 20.0 mmol). The pale yellow solution turned into a bright yellow solution and after stirring for 5 minutes, a precipitate formed. The mixture was stirred at room temperature for 2 hours. The solid was collected by filtration and washed with ether (5×10 ml). The yellow solid was dried overnight under vacuum at 90° C. to give 0.52 g of the title hydrochloride salt as a white solid.

Example 105 were synthesized in a manner similar to that described for Example 104.

Example 106

1-(2-fluorophenyl)-3-(piperidin-4-yloxy)-1H-indazole L-tartrate

To a stirred suspension of 2-fluorophenylhydrazine, hydrochloride (100 g, 0.614 moles) in ethanol (1.0 L) was added in a stream over a 10 minute period at 22-23° C., triethylamine (68.4 g, 0.68 moles). The suspension was stirred for 5 minutes and then isatoic anhydride (100 g, 0.614 moles) was added. The resulting suspension was stirred at temperatures reaching reflux (78° C.) over the next hour as a solution formed. The solution was stirred at reflux for 2.5 hours. It was then stirred at −10° C. for 2 hours and filtered. The solid was rinsed with ethyl acetate (100 ml) and pressed dry under suction. The solid was suspended in water (400 ml) and stirred at room temperature for 0.5 hour. The solid was filtered off, washed with water (5×30 ml) and pressed dry under suction. Further drying in vacuo at 33° C. for 17 hours afforded 63.3 g (42%) of Intermediate 48 (2-amino-benzoic acid N'-(2-fluoro-phenyl)-hydrazide). The organic filtrate was concentrated in vacuo to dryness. The residue was triturated with water (500 ml, then 3×200 ml) and suspended in ethanol:ethyl acetate (1:1, 150 ml). The solid was filtered off, rinsed with ethyl acetate (50 ml) and pressed dry under suction. Further drying in vacuo at 32° C. for 6 hours provided an additional 13.7 g (9%) of product. Total yield=77.0 g (51%). $^1$H NMR (DMSO-d$_6$) δ: 10.1 (s, 1H), 7.6 (m, 1H), 7.2 (t, 1H), 7.1 (m, 1H), 6.95 (m, 1H), 6.8 (t, 1H), 6.7 (m, 2H), 6.5 (t, 1H), 6.4 (s, 2H).

To a stirred suspension of Intermediate 48 (150 g, 0.257 moles) in 1 N HCl (560 ml) at −3° C. to −2° C. was added dropwise over a 40 minute period, a solution of sodium nitrite (35.5 g, 0.514 moles) in water (175 ml). Gas evolution was noted. The foamy suspension was stirred at 0° C. to −5° C. for 0.5 hour. Ethanol (1.05 L) was added and the solution was heated to reflux over a 45-minute period. The suspension was stirred at reflux for 1.5 hours. Ethanol (~250 ml) was distilled off at atmospheric pressure over the next 45 minutes. The suspension was cooled with stirring to −10° C. for 0.5 hour and filtered. The solid was rinsed four times with 30 ml of isopropanol and pressed dry under suction. Further drying in vacuo at 58° C. for 7 hours afforded 52.5 g (89.5%) of Intermediate 1 (1-(2-fluoro-phenyl)-1H-indazol-3-ol). $^1$H NMR (DMSO-d$_6$) δ: 7.7 (d, 1H), 7.6 (t, 1H), 7.3-7.5 (m, 4H), 7.2 (m, 1H), 7.1 (t, 1H).

To Intermediate 1 (52 g, 0.228 moles) in dimethylformamide (480 ml) was added cesium carbonate (111.5 g, 0.342 moles) with stirring. The mixture was stirred at room temperature for 0.5 hour. The 4-methanesulfonyloxy-piperidine-1-carboxylic acid tert-butyl ester Intermediate 2 (70 g, 0.251 moles) was added and the mixture was stirred at 80-85° C. for 18 hours. The resulting suspension was cooled to 10° C. with an ice-water bath. Saturated aqueous ammonium chloride (250 ml) was added in a stream over a 20-minute period. The mixture was poured into stirred ice-water (2 L). The mixture was extracted with ether (1 L, 500 ml). The extract was dried over magnesium sulfate and concentrated in vacuo to an orange-amber oil (124 g). This oil was dissolved in a mixture of hexane:ethyl acetate (1:8, 150 ml). Silica gel (230-400 mesh, 150 g) was added to the turbid solution. The slurry was poured onto a silica gel (230-400 mesh, 850 g) pad. The pad was eluted with ethyl acetate in hexane (5%→8%). The total volume of solvent used was 21 L. The combined eluates were concentrated in vacuo to 88 g (94%) of Intermediate 3 (4-[1-(2-Fluoro-phenyl)-1H-indazol-3-yloxy]-piperidine-1-carboxylic acid tert-butyl ester) as a pale yellow gum. $^1$H NMR (CDCl$_3$) δ: 7.7 (d, 1H), 7.6 (t, 1H), 7.4 (t, 1H), 7.2-7.4 (m, 4H), 7.15 (t, 1H), 5.1 (m,1H), 3.8 (m, 2H), 3.4 (m, 2H), 2.1 (m, 2H), 2.05 (s, 3H), 1.9 (m, 2H), 1.5 (s, 9H).

To a stirred solution of Intermediate 3 (85 g, 0.207 moles) in ethyl acetate (600 ml) at 21° C. was added in a narrow stream over a 35-minute period, 4M HCl in dioxane (600 ml) causing a temperature rise to 24° C. The solution was stirred at 22-23° C. for 3 hours. The solution was concentrated in vacuo to a thick oil which began to solidify. Ethyl acetate (200 ml) was added and the resulting thick suspension was stirred at 0° C. for 1 hour. The solid was filtered off, rinsed twice with 30 ml of ethyl acetate and pressed dry under suction. Further drying in vacuo at 35° C. for 16 hours afforded 66.5 g (93%) of 1-(2-fluoro-phenyl)-3-(piperidin-4-yloxy)-1H-indazole hydrochloride. $^1$H NMR (CD$_3$OD) δ: 7.7 (d, 1H), 7.6 (t, 1H), 7.5-7.6 (m, 2H), 7.3-7.5 (m, 2H), 7.25 (m, 1H), 7.2 (t, 1H), 5.2 (m, 1H), 3.4-3.5 (m, 2H), 3.2-3.3 (m, 2H), 2.3-2.4 (m, 2H), 2.2-2.3 (m, 2H). MS (APCI): (M+1)=311.

A mixture of 1-(2-fluoro-phenyl)-3-(piperidin-4-yloxy)-1H-indazole hydrochloride (9.0 g, 0.026 moles) in tetrahydrofuran (20 ml) and water (100 ml) was stirred at room temperature for 0.5 hour as a solution formed. Sodium carbonate (15 g, 0.142 moles) was added portion-wise over a 5-minute period, followed by ether (150 ml). The mixture was shaken and the layers were separated. The aqueous layer was extracted with ether (100 ml). The combined organic layers were dried over magnesium sulfate and concentrated in vacuo to a gum (8.0 g, 99% crude). To this gum was added, all at once, a solution of L-tartaric acid (4.0 g, 0.0267 mol) in water (80 ml). The mixture was stirred for ~2 minutes when a complete solution formed. Stirring was continued and after ~2 minutes solid began precipitating. The suspension was stirred at 0° C. for 3 hours and filtered. The solid was rinsed with water (15 ml) and pressed dry under suction. Further drying in vacuo at 50° C. for 16 hours provided 10.2 g (85.5%) of the L-tartrate salt—1-(2-fluoro-phenyl)-3-(piperidin-4-yloxy)-1H-indazole L-tartrate.

Example 107

(S)-5-fluoro-1-(2-fluorophenyl)-3-(piperidin-3-ylmethoxy)-1H-indazole L-tartrate 2-Amino-5-fluoro-benzoic acid (20.0 g, 129 mmol) was dissolved in dry THF (390 ml). 1,1'-Carbonyldiimidazole (CDI, 22.0 g, 135 mmol) was added in one portion. Some gas evolution was observed and a very thick beige solid precipitated out. The suspension was stirred for 1 hour 20 minutes at room temperature. Eventually, the precipitate thinned out. N,N-diisopropylethylamine (DIPEA, 27 ml, 155 mmol) was added, which caused the precipitate to fully dissolve, followed by the addition of (2-fluoro-phenyl)-hydrazine hydrochloride (23.1 g, 142 mmol). The mixture was stirred at room temperature for 18 hours. The reaction was carefully quenched with water (1 L) and ethyl acetate (500 ml) was added. The two layers were separated and the aqueous layer was washed twice with 200 ml of water, then twice with 100 ml of saturated, aqueous NaHCO$_3$ solution, then with saturated brine, and dried over MgSO$_4$. The solvent was removed to give 32.21 g (95% yield) of Intermediate 22 (2-amino-5-fluoro-benzoic acid N'-(2-fluoro-phenyl)-hydrazide) as a brown-red solid. MS (APCI): (M+1)=264. $^1$H and $^{19}$F NMR spectra agreed with the structure. The solid was used in the next step without any further purification.

A 500-ml, 3-necked, round bottomed-flask equipped with a magnetic stirrer, an addition funnel and a thermometer was charged with a suspension of Intermediate 22 (10.00 g, 38 mmol) in 1 N HCl (130 ml) and ethanol (130 ml). The suspension was heated to 76° C., which caused the solid to fully dissolve. A solution of NaNO$_2$ (5.24 g, 76 mmol) in water (12 ml) was added dropwise over 15 minutes. Gas evolution was observed and, after a few minutes, a beige solid crashed out of solution. When the NaNO$_2$ solution addition was complete, the mixture was refluxed for 1 hour. The mixture was allowed to cool to room temperature and the solid was filtered, washed with water (3×50 ml) and dried at 50° C. for 24 hours in a vacuum oven at 17 torr to give 4.18 g (92%) of Intermediate 23 (5-fluoro-1-(2-fluoro-phenyl)-1H-indazol-3-ol) as a beige solid. MS (APCI): (M+1)=247. $^1$H and $^{19}$F NMR spectra agreed with the structure. The solid was used in the next step without any further purification.

Intermediate 23 (9.86 g, 40 mmol) was dissolved in DMF (100 ml). K$_2$CO$_3$ (8.30 g, 60 mmol) was added and the mixture was stirred at room temperature for 10 minutes. Then a solution of (S)-3-methanesulfonyloxy-methyl-piperidine-1-carboxylic acid tert-butyl ester Intermediate 11 (11.75 g, 40 mmol) in 10 ml of DMF was added in one portion and the resulting mixture was stirred at 80-85° C. for 18 hours. Saturated, aqueous NH$_4$Cl solution (200 ml) and water (1 L) were added and the aqueous phase was extracted with MTBE (methyl tert-butyl ether) (3×200 ml). The combined organic extracts were washed twice with 100 ml of water, then saturated brine, and dried over MgSO$_4$. The solvent was removed under vacuum to give a brown solid that was passed through a plug of silica gel (hexanes/ethyl acetate 3/1 as mobile phase) to give 16.37 g (92% yield) of Intermediate 24 ((S)-3-[5-fluoro-1-(2-fluoro-phenyl)-1H-indazol-3-yloxymethyl]-piperidine-1-carboxylic acid tert-butyl ester) as a very thick yellow oil. MS (APCI): (M+1)=444. $^1$H and $^{19}$F NMR spectra agreed with the structure.

Intermediate 24 (20.6 g, 46 mmol) was dissolved in ethyl acetate (150 ml) and the solution was cooled in an ice water bath. 4 M HCl in dioxane (150 ml) was added in one portion and the mixture was allowed to warm up to room temperature. After 1 hour the solvent was removed under vacuum to give a very thick, pale yellow oil. Ethyl acetate was added to redissolve the oil and removed under vacuum to give a foamy, yellow solid. Diethyl ether (300 ml) was added to the oil and the suspension was slurried for 18 hours at room temperature. The resulting solid was filtered, washed twice with 50 ml of diethyl ether and dried in a vacuum oven at 50° C. for 24 hours to give 15.39 g (87%) of (S)-5-fluoro-1-(2-fluoro-phenyl)-3-(piperidin-3-ylmethoxy)-1H-indazole hydrochloride as a pale yellow solid. MS (APCI): (M+1)=344. $^1$H and $^{19}$F NMR spectra agreed with the structure.

(S)-5-Fluoro-1-(2-fluoro-phenyl)-3-(piperidin-3-ylmethoxy)-1H-indazole hydrochloride (14.0 g, 37 mmol) was suspended in ethyl acetate (100 ml) and a 1 M solution of K$_2$CO$_3$ in water (100 ml) was added. The resulting mixture was vigorously stirred, which caused the solid to dissolve completely. After 1 hour, the two layers were separated and the aqueous layer was extracted twice with 50 ml of ethyl acetate. The combined organic extracts were washed with brine and dried over MgSO$_4$. The solvent was removed under vacuum to give 11.9 g (94%) of the free base (S)-5-fluoro-1-(2-fluoro-phenyl)-3-(piperidin-3-ylmethoxy)-1H-indazole as a very thick yellow oil. $^1$H and $^{19}$F NMR spectra agreed with the structure.

The free base (20.9 g, 61 mmol) was dissolved in methanol (200 ml). L-tartaric acid (9.1 g, 61 mmol) was added in one portion and the mixture was stirred at room temperature for 10 minutes to give a clear solution. The solvent was removed under vacuum to give a pale yellow solid, which was slurried in diethyl ether (500 ml) for 2 hours. The solid was filtered, washed with diethyl ether (50 ml) and dried in vacuum oven at 50° C. and 17 torr for 2 hours and then at room temperature for 48 hours to give 27.8 g (93%) of the L-tartrate salt (S)-5-fluoro-1-(2-fluorophenyl)-3-(piperidin-3-ylmethoxy)-1H-indazole L-tartrate as a white solid. $^1$H and $^{19}$F NMR spectra agreed with the structure. HPLC: chemical purity: 98.7% a/a; chiral: 100% ee. Combustion (CHN) analysis: passed.

Examples 108-111 were synthesized in a manner similar to that described for Example 107, except Cs$_2$CO$_3$ was used instead of K$_2$CO$_3$ and HCl was used for deprotection and salt formation.

| Ex. # | NAME | MS MP (° C.) CHN NMR and $[\alpha]_D^{24}$ |
|---|---|---|
| 1 | 1-(2-Fluorophenyl)-3-(piperidin-4-yloxy)-1H-indazole hydrochloride | 210-211° C.<br>Found for C$_{18}$H$_{18}$FN$_3$O•HCl•0.25H$_2$O: C, 61.32; H, 5.59; N, 11.71; F, 5.39; Cl, 10.09<br>$^1$H NMR(400MHz, DMSO-D$_6$) δppm 2.06(m, 2H), 2.28(ddd, J=10.31, 7.02, 3.42Hz, 2H), 3.11(ddd, J=12.63, 8.60, 3.66Hz, 2H), 3.26(m, 2H), 5.11(ddd, J=11.35, 7.56, 3.54Hz, 1H), 7.19(t, J=7.44Hz, 1H), 7.27(dd, J=8.54, 3.42Hz, 1H), 7.37(dt, J=8.48, 4.18Hz, 1H), 7.46(dd, J=8.30, 0.98Hz, 1H), 7.49(m, 2H), 7.62(m, 1H), 7.75(d, J=8.05Hz, 1H), 9.09(s, 2H) |
| 2 | (S)-(+)-1-(2-Fluorophenyl)-3-(morpholin-2-ylmethoxy)-1H-indazole maleate | MS(APCI)M+1=328<br>158-160° C.<br>Found for C$_{18}$H$_{18}$FN$_3$O$_2$•C$_4$H$_4$O$_4$: C, 59.71; H, 4.84; N, 9.44; F, 4.44<br>$^1$H NMR(400MHz, DMSO-D6) δppm 3.03(td, J=12.20, 3.42Hz, 2H), 3.21(d, J=13.18Hz, 1H), 3.39(d, J=11.96Hz, 1H), 3.74(td, J=12.38, 2.56Hz, 1H), 4.03(dd, J=12.57, 3.05Hz, 1H), |

-continued

| Ex. # | NAME | MS MP (° C.) CHN NMR and $[\alpha]_D^{24}$ |
|---|---|---|
| | | 4.15(m, 1H), 4.45(ddd, J=14.76, 11.47, 4.76Hz, 2H), 5.99(m, 2H), 7.21(m, 1H), 7.28(dd, J=8.54, 3.66Hz, 1H), 7.38(m, 1H), 7.49(m, 3H), 7.61(m, 1H), 7.73(d, J=8.05Hz, 1H), 8.82(s, 2H) $[\alpha]_D^{24}$=+2.9 degrees(MeOH, c=6.5) |
| 3 | (S)-(+)-1-(2,4-Difluorophenyl)-3-(morpholin-2-ylmethoxy)-1H-indazole maleate | MS(APCI)M+1=346<br>150-151° C.<br>Found for $C_{18}H_{17}F_2N_3O_2 \cdot C_4H_4O_4$: C 57.09; H, 4.42; N, 8.99; F, 8.02<br>$[\alpha]_D^{24}$=+1.6 degrees(MeOH, c=5.1) |
| 4 | 1-(2-Fluorophenyl)-3-(piperidin-3-ylmethoxy)-1H-indazole hydrochloride | MS(APCI)M+1=326<br>131-133° C.<br>Found for $C_{19}H_{20}FN_3O \cdot HCl \cdot 0.4H_2O$: C, 61.87; H, 6.16; N, 11.37; F, 5.08; Cl, 9.61 |
| 5 | (R)-(−)-1-(2-Fluorophenyl)-3-(morpholin-2-ylmethoxy)-1H-indazole hydrochloride | MS(APCI)M+1=328<br>103-104° C.<br>Found for $C_{18}H_{18}FN_3O_2 \cdot HCl \cdot 0.15H_2O$: C, 59.00; H, 5.32; N, 11.12; F, 5.42; Cl, 9.55<br>$[\alpha]_D^{24}$=−4 degrees(MeOH, c=5.0) |
| 6 | (S)-(−)-1-(2-Fluorophenyl)-3-(piperidin-3-ylmethoxy)-1H-indazole hydrochloride | MS(APCI)M+1=326<br>196-197° C.<br>Found for $C_{19}H_{20}FN_3O \cdot HCl \cdot 0.2H_2O$: C, 62.45; H, 5.96; N, 11.22; F, 5.19; Cl, 9.69<br>$[\alpha]_D^{24}$=−15.7 degrees(MeOH, c=5.1) |
| 7 | (S)-(−)-1-(2-Fluorophenyl)-3-(pyrrolidin-3-ylmethoxy)-1H-indazole hydrochloride | MS(APCI)M+1=312<br>100-101° C.<br>Found for $C_{18}H_{18}FN_3O \cdot HCl \cdot 0.45H_2O$: C, 60.78; H, 5.70; N, 11.97; F, 5.43; Cl, 9.96<br>$[\alpha]_D^{24}$=−1 degree(MeOH, c=5.0) |
| 8 | (S)-1-(2,4-Difluorophenyl)-3-(pyrrolidin-3-ylmethoxy)-1H-indazole hydrochloride | MS(APCI)M+1=330.1<br>Found for $C_{18}H_{17}F_2N_3O \cdot HCl \cdot 0.47 H_2O$; C, 57.38; H, 4.91; N, 10.99; F, 9.78; Cl, 9.68<br>$^1$H NMR(400MHz, DMSO-D6) δppm 1.8(m, 1H), 2.1(m, 1H), 2.9(m, 1H), 3.1(dd, J=11.7, 7.1Hz, 1H), 3.2(m, 1H), 3.3(m, 1H), 3.4(dd, J=11.8, 8.2Hz, 1H), 4.4(m, 2H), 7.2(t, J=7.4Hz, 1H), 7.3(m, 2H), 7.5(m, 1H), 7.6(m, 1H), 7.7(td, J=8.9, 5.9Hz, 1H), 7.8(d, J=8.1Hz, 1H), 9.1(bs, 2H). |
| 9 | (R)-1-(2,4-Difluorophenyl)-3-(pyrrolidin-3-ylmethoxy)-1H-indazole hydrochloride | MS(APCI)M+1=330.1<br>Found for $C_{18}H_{17}F_2N_3O \cdot HCl \cdot 0.38 H_2O$; C, 57.64; H, 4.94; N, 11.16; F, 9.80; Cl, 9.61<br>$^1$H NMR(400MHz, DMSO-D6) δppm 1.8(m, 1H), 2.1(m, 1H), 2.9(m, 1H), 3.1(dd, J=11.7, 7.1Hz, 1H), 3.2(m, 1H), 3.3(m, 1H), 3.4(dd, J=11.6, 7.9Hz, 1H), 4.4(m, 2H), 7.2(m, 1H), 7.3(m, 2H), 7.5(m, 1H), 7.6(m, 1H), 7.7(td, J=8.9, 6.1Hz, 1H), 7.8(d, J=8.1Hz, 1H), 9.1(bs, 2H) |
| 10 | 1-(2,4-Difluorophenyl)-3-(piperidin-4-yloxy)-1H-indazole hydrochloride | MS(APCI)M+1=330.1<br>Found for $C_{18}H_{17}F_2N_3O \cdot 1.2$ HCl; C, 58.32; H, 4.88; N, 11.22; F, 9.61; Cl, 11.37<br>$^1$H NMR(400MHz, DMSO-D6) δppm 2.1(m, 2H), 2.3(m, 2H), 3.1(m, 2H), 3.3(m, 2H), 5.1(m, 1H), 7.2(m, 1H), 7.3(m, 2H), 7.5(m, 1H), 7.6(m, 1H), 7.7(td, J=8.9, 6.1Hz, 1H), 7.8(d, J=9.0Hz, 1H), 9.0(bs, 2H). |
| 11 | (R)-1-(2-Fluorophenyl)-3-(pyrrolidin-3-ylmethoxy)-1H-indazole hydrochloride | MS(APCI)M+1=312.1<br>Found for $C_{18}H_{18}F_1N_3O \cdot 1.05$ HCl$\cdot 0.46 H_2O$; C, 60.33; H, 5.59; N, 11.61; F, 5.40; Cl, 10.77<br>$^1$H NMR(400MHz, DMSO-D6) δppm 1.8(m, 1H), 2.1(m, 1H), 2.9(m, 1H), 3.1(m, 1H), 3.2(m, 1H), 3.3(m, 1H), 3.4(dd, J=11.5, 8.1Hz, 1H), 4.4(m, 2H), 7.2(t, J=7.6Hz, 1H), 7.3(dd, J=8.5, 3.7Hz, 1H), 7.4(m, 1H), 7.5(m, 3H), 7.6(t, J=7.8Hz, 1H), 7.8(d, J=7.8Hz, 1H), 9.2(bs, 2H). |
| 12 | (S)-(−)-1-(2-Fluorophenyl)-3-(pyrrolidin-2-yloxy)-1H-indazole hydrochloride | MS(APCI)M+1=298<br>130-131° C.<br>Found for $C_{17}H_{16}FN_3O \cdot 1.05HCl \cdot 0.3H_2O$: C, 59.98; H, 5.27; N, 12.26; F, 5.53; Cl, 10.76<br>$[\alpha]_D^{24}$=−10.5 degrees(MeOH, c=6.1) |
| 13 | (R)-(+)-1-(2-Fluorophenyl)-3-(pyrrolidin-2-yloxy)-1H-indazole maleate | MS(APCI)M+1=298<br>116-117° C.<br>Found for $C_{17}H_{16}FN_3O \cdot C_4H_4O_4$: C, 60.97; H, 4.81; N, 10.13; F, 4.67<br>$[\alpha]_D^{24}$=+10.1 degrees(MeOH, c=7.3) |
| 14 | (R)-1-Phenyl-3-(pyrrolidin-3-ylmethoxy)-1H-indazole | MS(APCI)M+1=294.1<br>Found for $C_{18}H_{19}N_3O \cdot 1.0$ HCl$\cdot 0.23 H_2O$; C, 64.35; H, 6.17; N, 12.21; Cl, 10.52<br>$^1$H NMR(400MHz, DMSO-D6) δppm 1.9(m, 1H), 2.2(m, 1H), |

-continued

| Ex. # | NAME | MS MP (° C.) CHN NMR and $[\alpha]_D^{24}$ |
|---|---|---|
|  | hydrochloride | 2.9(m, 1H), 3.1(m, 1H), 3.2(m, 1H), 3.3(m, 1H), 3.4(dd, J=11.7, 8.1Hz, 1H), 4.5(m, 2H), 7.2(m, 1H), 7.3(t, J=7.9Hz, 1H), 7.5(m, 3H), 7.7(d, J=8.8Hz, 2H), 7.8(dd, J=15.7, 8.9Hz, 2H), 9.2(bs, 2H). |
| 15 | (±)-1-Phenyl-3-(piperidin-3-yloxy)-1H-indazole hydrochloride | MS(APCI)M+1=294<br>183-184° C.<br>Found for $C_{18}H_{19}N_3O\cdot HCl$: C, 65.31; H, 6.15; N, 12.66; Cl, 10.72 |
| 16 | (±)-1-Phenyl-3-(piperidin-3-ylmethoxy)-1H-indazole hydrochloride | MS(APCI)M+1=308<br>215-216° C.<br>Found for $C_{19}H_{21}N_3O\cdot HCl$: C, 66.41; H, 6.43; N, 12.05; Cl, 10.40 |
| 17 | (±)-1-Phenyl-3-(piperidin-4-ylmethoxy)-1H-indazole hydrochloride | MS(APCI)M+1=308<br>218-219° C.<br>Found for $C_{19}H_{21}N_3O\cdot HCl$: C, 66.22; H, 6.56; N, 12.01; Cl, 10.32 |
| 18 | (R)-(+)-1-Phenyl-3-(piperidin-3-ylmethoxy)-1H-indazole hydrochloride | MS(APCI)M+1=308<br>163-164° C.<br>Found for $C_{19}H_{21}N_3O\cdot HCl$: C, 66.04; H, 6.50; N, 12.13; Cl, 10.35<br>$[\alpha]_D^{24}$=+14.4 degrees(MeOH, c=5.0) |
| 19 | (S)-(−)-1-Phenyl-3-(piperidin-3-ylmethoxy)-1H-indazole hydrochloride | MS(APCI)M+1=308<br>165-166° C.<br>Found for $C_{19}H_{21}N_3O\cdot HCl$: C, 66.02; H, 6.49; N, 12.04; Cl, 10.11<br>$[\alpha]_D^{24}$=−17.1 degrees(MeOH, c=4.9) |
| 20 | 1-Phenyl-3-(piperidin-4-yloxy)-1H-indazole hydrochloride | MS(APCI)M+1=294<br>154-156° C.<br>Found for $C_{18}H_{19}N_3O\cdot HCl$: C, 65.28; H, 6.05; N, 12.58; Cl, 10.90 |
| 21 | (S)-(+)-3-(Morpholin-2-ylmethoxy)-1-phenyl-1H-indazole hydrochloride | MS(APCI)M+1=310<br>165-166° C.<br>Found for $C_{18}H_{19}N_3O_2\cdot HCl$: C, 62.22; H, 5.79; N, 12.00; Cl, 10.54<br>$[\alpha]_D^{24}$=+3.3 degrees(MeOH, c=10.2) |
| 22 | (S)-1-Phenyl-3-(pyrrolidin-3-ylmethoxy)-1H-indazole hydrochloride | MS(APCI)M+1=294.1<br>Found for $C_{18}H_{19}N_3O\cdot 1.05$ HCl$\cdot 0.39$ H$_2$O; C, 63.79; H, 5.96; N, 12.12; Cl, 11.16<br>$^1$H NMR(400MHz, DMSO-D6) δppm 1.9(m, 1H), 2.2(m, 1H), 2.9(m, 1H), 3.1(m, 1H), 3.2(m, 1H) 3.3(m, 1H), 3.4(dd, J=11.6, 7.9Hz, 1H), 4.5(m, 2H), 7.2(m, 1H), 7.3(t, J=7.4Hz, 1H), 7.5(m, 3H), 7.7(d, J=7.6Hz, 2H), 7.8(dd, J=14.9, 8.3Hz, 2H), 9.3(bs, 2H). |
| 23 | (S)-1-(3,4-Difluorophenyl)-3-(morpholin-2-ylmethoxy)-1H-indazole hydrochloride | 177-179° C.<br>Found for $C_{18}H_{17}F_2N_3O_2\cdot 1.05$ HCl$\cdot 0.15$ H$_2$O; C, 55.67; H, 4.43; N, 10.67; Cl, 9.38; F, 10.00 |
| 24 | (S)-1-(2,6-Difluorophenyl)-3-(morpholin-2-ylmethoxy)-1H-indazole hydrochloride | 217-218° C.<br>Found for $C_{19}H_{19}F_2N_3O_1\cdot 1.0$ HCl; C, 56.45; H, 4.55; N, 10.95; Cl, 9.26<br>$[\alpha]_D^{24}$=+2.2 degrees(MeOH, c=7.2) |
| 25 | (S)-1-(2,6-Difluorophenyl)-3-(piperidin-3-ylmethoxy)-1H-indazole maleate | 139-141° C.<br>Found for $C_{19}H_{19}F_2N_3O_1\cdot 1.0$ $C_4H_4O_4$; C, 59.76; H, 5.02; N, 8.99; F, 8.27<br>$[\alpha]_D^{24}$=−8.9 degrees(MeOH, c=7.2) |
| 26 | (S)-1-(2,5-Difluorophenyl)-5-fluoro-3-(morpholin-2-ylmethoxy)-1H-indazole maleate | 169-170° C.<br>Found for $C_{18}H_{16}F_3N_3O_2\cdot C_4H_4O_4$: C, 55.10; H, 4.14; N, 8.67; F, 11.91<br>$[\alpha]_D^{24}$=+4.2 degrees(MeOH, c=8.8) |
| 27 | 1-(2,5-Difluorophenyl)-3-(piperidin-4-yloxy)-1H-indazole hydrochloride | MS(APCI)M+1=330.1<br>Found for $C_{18}H_{17}F_2N_3O\cdot 1.0$ HCl; C, 58.78; H, 4.79; N, 11.35; F, 10.24; Cl, 9.92<br>$^1$H NMR(400MHz, DMSO-D6) δppm 2.1(m, 2H), 2.3(m, 2H), 3.1(m, 2H), 3.3(m, 2H), 5.1(m, 1H), 7.2(t, J=7.9Hz, 1H), 7.4(m, 2H), 7.5(m, 3H), 7.8(d, J=8.1Hz, 1H), 8.8(bs, 2H). |
| 28 | (S)-(+)-1-(2,5-Difluorophenyl)-3-(morpholin-2-ylmethoxy)-1H-indazole maleate | MS(APCI)M+1=346<br>156-157° C.<br>Found for $C_{18}H_{17}F_2N_3O_2\cdot C_4H_4O_4$: C, 57.44; H, 4.64; N, 9.08; F, 8.26<br>$[\alpha]_D^{24}$=+3.8 degrees(MeOH, c=5.5) |

-continued

| Ex. # | NAME | MS MP (° C.) CHN NMR and $[\alpha]_D^{24}$ |
|---|---|---|
| 29 | 1-(3,5-Dichloro-phenyl)-3-(piperidin-4-yloxy)-1H-indazole hydrochloride | MS(APCI)M+1=362.1<br>$^1$H NMR(400MHz, DMSO-D6) δppm 2.1(m, 2H), 2.3(m, 2H), 3.2(ddd, J=12.6, 8.6, 3.7Hz, 2H), 3.3(m, 2H), 5.2(ddd, J=7.6, 4.1, 3.9Hz, 1H), 7.3(m, 1H), 7.5(t, J=1.8Hz, 1H), 7.6(ddd, J=8.5, 7.1, 1.0Hz, 1H), 7.8(m, 3H), 7.9(d, J=8.5Hz, 1H), 8.8(s, 2H). |
| 30 | (R)-1-(2,5-Difluoro-phenyl)-3-(pyrrolidin-3-ylmethoxy)-1H-indazole hydrochloride | MS(APCI)M+1=330.1<br>$^1$H NMR(400MHz, DMSO-D6) δppm 1.8(m, 1H), 2.1(m, 1H), 2.9(m, 1H), 3.1(dd, J=11.7, 7.1Hz, 1H), 3.2(m, 1H), 3.3(m, 1H), 3.4(dd, J=11.6, 7.9Hz, 1H), 4.4(m, 2H), 7.2(t, J=7.2Hz, 1H), 7.4(m, 2H), 7.6(m, 3H), 7.8(d, J=8.1Hz, 1H), 9.1(bs, 2H). |
| 31 | (±)-1-(2,5-Difluoro-phenyl)-3-(piperidin-3-ylmethoxy)-1H-indazole hydrochloride | MS(APCI)M+1=344.2<br>Found for $C_{19}H_{19}F_2N_3O$•1.0 HCl•0.03 $H_2O$; C, 59.72; H, 5.36; N, 10.78; F, 9.59; Cl, 9.38<br>$^1$H NMR(400MHz, DMSO-D6) δppm 1.4(m, 1H), 1.7(m, 1H), 1.9(m, 2H), 2.4(m, 1H), 2.8(m, 2H), 3.2(d, J=11.5Hz, 1H), 3.4(d, J=11.5Hz, 1H), 4.3(dd, J=10.4, 7.2Hz, 1H), 4.4(m, 1H), 7.2(t, J=7.4Hz, 1H), 7.4(m, 2H), 7.6(m, 3H), 7.8(d, J=8.1Hz, 1H), 9.0(m, 1H), 9.1(m, 1H). |
| 32 | (S)-1-(2,5-Difluoro-phenyl)-3-(pyrrolidin-3-ylmethoxy)-1H-indazole hydrochloride | MS(APCI)M+1=330.1<br>Found for $C_{18}H_{17}F_2N_3O$•1.0 HCl•0.40 $H_2O$; C, 58.30; H, 4.96; N, 11.12; F, 9.79; Cl, 9.81<br>$^1$H NMR(400MHz, DMSO-D6) δppm 1.8(m, 1H), 2.1(m, 1H), 2.9(m, 1H), 3.1(m, 1H), 3.2(m, 1H), 3.3(m, 1H), 3.4(m, 1H), 4.4(m, 2H), 7.2(t, J=7.4Hz, 1H), 7.4(m, 2H), 7.6(m, 3H), 7.8(d, J=8.1Hz, 1H), 9.3(bs, 2H). |
| 33 | (S)-1-(3,4-Difluoro-phenyl)-3-(piperidin-3-ylmethoxy)-1H-indazole hydrochloride | MS(APCI)M+1=344.2<br>$^1$H NMR(400MHz, DMSO-D6) δppm 1.36(m, 1H), 1.77(m, 3H), 2.38(m, 2H), 2.77(m, 2H), 3.20(d, J=12.45Hz, 1H), 3.36(d, J=11.96Hz, 1H), 4.33(m, 2H), 7.20(t, J=7.45Hz, 1H), 7.53(m, 3H), 7.75(m, 3H), 9.06(s, 2H). |
| 34 | 1-(3,4-Difluoro-phenyl)-3-(piperidin-4-yloxy)-1H-indazole hydrochloride | MS(APCI)M+1=330.2<br>$^1$H NMR(400MHz, DMSO-D6) δppm 2.04(m, 2H), 2.27(m, 2H), 3.10(m, 2H), 3.24(dd, J=7.32, 4.15Hz, 2H), 5.14(m, 1H), 7.20(t, J=7.20Hz, 1H), 7.54(m, 3H), 7.76(m, 3H), 9.05(bs, 2H) |
| 35 | (S)-1-(3,4-Difluoro-phenyl)-3-(pyrrolidin-3-ylmethoxy)-1H-indazole hydrochloride | MS(APCI)M+1=330.2<br>$^1$H NMR(400MHz, DMSO-D6) δppm 1.79(m, 1H), 2.11(m, 1H), 2.85(m, 1H), 3.06(dd, J=11.47, 7.08Hz, 1H), 3.14(m, 1H), 3.24(m, 1H), 3.35(dd, J=11.60, 7.93Hz, 1H), 4.43(m, 2H), 7.20(t, J=7.20Hz, 1H), 7.54(m, 3H), 7.76(m, 3H), 9.15(bs, 2H). |
| 36 | 1-(2,6-Difluoro-phenyl)-3-(piperidin-4-yloxy)-1H-indazole hydrochloride | MS(APCI)M+1=330.2<br>$^1$H NMR(400MHz, DMSO-D6) δppm 2.00(m, 2H), 2.23(m, 2H), 3.07(m, 2H), 3.24(m, 2H), 5.04(m, 1H), 7.17(m, 2H), 7.36(t, J=8.42Hz, 2H), 7.44(m, 1H), 7.60(m, 1H), 7.73(d, J=8.06Hz, 1H), 9.01(bs, 2H). |
| 37 | (S)-1-(2,6-Difluoro-phenyl)-3-(pyrrolidin-3-ylmethoxy)-1H-indazole hydrochloride | MS(APCI)M+1=330.2<br>$^1$H NMR(400MHz, DMSO-D6) δppm 1.78(m, 1H), 2.08(m, 1H), 2.81(m, 1H), 3.19(m, 4H), 4.34(m, 2H), 7.17(m, 2H), 7.36(t, J=8.30Hz, 2H), 7.44(m, 1H), 7.60(m, 1H), 7.73(m, J=8.06Hz, 1H), 9.32(bs, 2H). |
| 38 | (S)-1-(2,5-Difluoro-phenyl)-3-(piperidin-3-ylmethoxy)-1H-indazole hydrochloride | MS(APCI)M+1=344.2<br>$^1$H NMR(400MHz, DMSO-D6) δppm 1.4(m, 1H), 1.7(m, 1H), 1.9(m, 2H), 2.4(m, 1H), 2.8(m, 2H), 3.2(d, J=12.7Hz, 1H), 3.4(m, J=12.6, 2.6Hz, 1H), 4.3(m, 2H), 7.2(t, J=7.4Hz, 1H), 7.4(m, 2H), 7.6(m, 3H), 7.8(d, J=7.8Hz, 1H), 8.9(bs, 2H). |
| 39 | 1-(2,5-Difluoro-phenyl)-5-fluoro-3-(piperidin-4-yloxy)-1H-indazole hydrochloride | MS(APCI)M+1=348.2<br>$^1$H NMR(400MHz, DMSO-D6) δppm 2.1(m, 2H), 2.3(m, 2H), 3.1(m, 2H), 3.3(m, 2H), 5.1(dq, J=7.4, 3.7Hz, 1H), 7.4(m, 3H), 7.6(m, 3H), 9.1(s, 1H). |
| 40 | (R)-1-(2,5-Difluoro-phenyl)-5-fluoro-3-(pyrrolidin-3-ylmethoxy)-1H-indazole hydrochloride | MS(APCI)M+1=348.2<br>$^1$H NMR(400MHz, DMSO-D6) δppm 1.8(m, 1H), 2.1(td, J=13.2, 7.8Hz, 1H), 2.9(dt, J=14.3, 7.1Hz, 1H), 3.1(dd, J=11.6, 7.0Hz, 1H), 3.2(m, 1H), 3.3(m, 2H), 4.4(ddd, J=17.1, 10.4, 6.7Hz, 2H), 7.4(m, 3H), 7.5(m, 3H), 9.3(s, 1H). |
| 41 | 1-(4-Chloro-phenyl)-3-(piperidin-4-yloxy)-1H-indazole hydrochloride | MS(APCI)M+1=328.1<br>$^1$H NMR(400MHz, DMSO-D6) δppm 2.1(m, 2H), 2.3(m, 2H), 3.1(ddd, J=12.6, 8.5, 3.8Hz, 2H), 3.3(m, 2H), 5.2(ddd, J=7.5, 4.0, 3.8Hz, 1H), 7.2(t, J=7.4Hz, 1H), 7.5(ddd, J=8.5, 7.1, 1.2Hz, 1H), 7.6(m, 2H), 7.8(m, 4H), 8.9(s, 1H) |
| 42 | 1-(4-Fluoro-phenyl)-3-(piperidin-4-yloxy)-1H-indazole | MS(APCI)M+1=312.2<br>$^1$H NMR(400MHz, DMSO-D6) δppm 2.0(m, 2H), 2.3(m, 2H), 3.1(ddd, J=12.7, 8.6, 3.5Hz, 2H), 3.3(m, 2H), 5.1(dt, J=7.6, 3.9Hz, |

-continued

| Ex. # | NAME | MS MP (° C.) CHN NMR and $[\alpha]_D^{24}$ |
|---|---|---|
| | hydrochloride | 1H), 7.2(t, J=7.2Hz, 1H), 7.4(m, 2H), 7.5(ddd, J=8.4, 7.1, 1.1Hz, 1H), 7.7(m, 4H), 8.8(s, 2H) |
| 43 | 1-(3-Fluoro-phenyl)-3-(piperidin-4-yloxy)-1H-indazole hydrochloride | MS(APCI)M+1=312.2<br>$^1$H NMR(400MHz, DMSO-D6) δppm 2.0(m, 2H), 2.3(m, 2H), 3.1(m, 2H), 3.3(m, 2H), 5.2(m, 1H), 7.1(m, 1H), 7.2(m, 1H), 7.6(m, 4H), 7.8(d, J=7.8Hz, 1H), 7.9(d, J=8.5Hz, 1H), 8.7(s, 2H) |
| 44 | (S)-(−)-3-(Piperidin-3-ylmethoxy)-1-pyridin-2-yl-1H-indazole maleate | MS(APCI)M+1=309<br>181-183° C.<br>Found for $C_{18}H_{20}N_4O \cdot C_4H_4O_4$: C, 62.24; H, 5.38; N, 13.12<br>$[\alpha]_D^{24}$=−12.1 degrees(MeOH, c=6.6) |
| 45 | (S)-(−)-5-Fluoro-1-(2-fluorophenyl)-3-(piperidin-3-ylmethoxy)-1H-indazole maleate | MS(APCI)M+1=344<br>141-142° C.<br>Found for $C_{19}H_{19}F_2N_3O \cdot C_4H_4O_4$: C, 59.76; H, 5.04; N, 9.10; F, 8.10<br>$^1$H NMR(400MHz, DMSO-D6) δppm 1.39(m, 1H), 1.63(m, 1H), 1.84(m, 2H), 2.31(m, 1H), 2.81(m, 2H), 3.25(d, J=13.18Hz, 1H), 3.43(dd, J=12.20, 3.66Hz, 1H), 4.26(dd, J=10.49, 7.08Hz, 1H), 4.35(m, 1H), 5.99(s, 2H), 7.35(m, 3H), 7.51(m, 3H), 7.61(m, 1H), 8.45(s, 2H)<br>$[\alpha]_D^{24}$=−11.0 degrees(MeOH, c=5.8) |
| 46 | (S)-(+)-5-Fluoro-1-(2-fluorophenyl)-3-(morpholin-2-ylmethoxy)-1H-indazole maleate | MS(APCI)M+1=346<br>155-156° C.<br>Found for $C_{18}H_{17}F_2N_3O_2 \cdot C_4H_4O_4$: C, 57.35; H, 4.55; N, 9.04; F, 8.10<br>$^1$H NMR(400MHz, DMSO-D6) δppm 3.03(m, 2H), 3.21(d, J=12.69Hz, 1H), 3.38(d, J=11.47Hz, 1H), 3.73(td, J=12.44, 2.44Hz, 1H), 4.02(dd, J=12.81, 3.05Hz, 1H), 4.14(ddd, J=11.35, 6.83, 4.76Hz, 1H), 4.44(ddd, J=13.97, 11.41, 4.64Hz, 2H), 5.99(s, 2H), 7.37(m, 3H), 7.51(m, 3H), 7.62(m, 1H), 8.82(s, 2H)<br>$[\alpha]_D^{24}$=+3.8 degrees(MeOH, c=6.1) |
| 47 | (S)-(−)-5-Fluoro-1-(2-fluorophenyl)-3-(piperidin-3-ylmethoxy)-1H-indazole hydrochloride | MS(APCI)M+1=326<br>205-207° C.<br>Found for $C_{19}H_{20}FN_3O \cdot HCl$: C, 62.75; H, 5.62; N, 11.49; F, 5.39; Cl, 9.96<br>$[\alpha]_D^{24}$=−13.1 degrees(MeOH, c=7.0) |
| 48 | (S)-(+)-1-(2,4-Difluorophenyl)-5-fluoro-3-(morpholin-2-ylmethoxy)-1H-indazole maleate | MS(APCI)M+1=364<br>151-152° C.<br>Found for $C_{18}H_{16}F_3N_3O_2 \cdot C_4H_4O_4$: C, 54.88; H, 4.14; N, 8.72; F, 12.29<br>$[\alpha]_D^{24}$=+3.2 degrees(MeOH, c=7.4) |
| 49 | (S)-(−)-1-(2,4-Difluorophenyl)-5-fluoro-3-(piperidin-3-ylmethoxy)-1H-indazole hydrochloride | MS(APCI)M+1=362<br>201-203° C.<br>Found for $C_{19}H_{18}F_3N_3O \cdot HCl$: C, 57.20; H, 4.75; N, 10.48; F, 14.37; Cl, 8.99<br>$[\alpha]_D^{24}$=−11.8 degrees(MeOH, c=5.6) |
| 50 | (S)-1-(2,6-Difluoro-phenyl)-5-fluoro-3-(morpholin-2-ylmethoxy)-1H-indazole hydrochloride | 247-249° C.<br>Found for $C_{18}H_{16}F_3N_3O_2 \cdot 1.0\ HCl$: C, 54.06; H, 4.19; N, 10.44; F, 14.41; Cl, 8.84<br>$[\alpha]_D^{24}$=+2.1 degrees(MeOH, c=7.1) |
| 51 | 5-Fluoro-1-(2-fluoro-phenyl)-3-(piperidin-4-yloxy)-1H-indazole hydrochloride | MS(APCI)M+1=330.1<br>Found for $C_{18}H_{17}F_2N_3O1 \cdot 1.0\ HCl \cdot 0.85\ H_2O$: C, 56.34; H, 5.30; N, 10.87; F, 9.99; Cl, 9.41<br>$^1$H NMR(400MHz, DMSO-D6) δppm 2.1(m, 2H), 2.3(m, 2H), 3.1(m, 2H), 3.3(m, 2H), 5.1(m, 1H), 7.4(m, 3H), 7.5(m, 2H), 7.6(dd, J=8.4, 2.3Hz, 1H), 7.6(t, J=7.8Hz, 1H), 9.1(bd, J=21.0Hz, 2H). |
| 52 | 5-Fluoro-1-(2-fluoro-phenyl)-3-(1-methyl-piperidin-3-ylmethoxy)-1H-indazole hydrogen chloride | MS(APCI)M+1=358<br>$^1$H NMR(400MHz, METHANOL-D4) δppm 1.3(s, 3H), 1.6(m, 1H), 1.9(m, 3H), 3.2(m, 4H), 3.3(s, 1H), 4.3(m, 2H), 7.3(m, 2H), 7.4(m, 2H), 7.6(m, 1H). |
| 53 | 1-(2-Fluoro-phenyl)-3-(3-methyl-piperidin-3-ylmethoxy)-1H-indazole hydrogen chloride | MS(APCI)M+1=340<br>$^1$H NMR(400MHz, METHANOL-D4) δppm 1.3(s, 3H), 1.7(m, 1H), 1.9(m, 3H), 3.2(m, 3H), 3.3(s, 1H), 4.4(m, 2H), 7.2(m, 2H), 7.4(m, 2H), 7.5(m, 2H), 7.6(m, 1H), 7.7(d, J=8.1Hz, 1H). |
| 54 | 5-Fluoro-1-(2-fluoro-phenyl)-3-(4-methyl-piperdin-4- | MS(APCI)M+1=358<br>$^1$H NMR(400MHz, METHANOL-D4) δppm 1.3(s, 3H) 1.8(m, 2H), 2.0(m, 2H) 3.2(m, 3H) 3.3(m, 2H) 4.3(s, 2H) 7.3(m, 2H) |

| Ex. # | NAME | MS MP (° C.) CHN NMR and $[\alpha]_D^{24}$ |
|---|---|---|
| | ylmethoxy)-1H-indazole hydrogen chloride | 7.4(m, 3H) 7.5(m, 1H) 7.6(m, 1H). |
| 55 | (R)-5-Fluoro-1-(2-fluoro-phenyl)-3-(piperidin-3-ylmethoxy)-1H-indazole maleate | MS(APCI)M+1=344<br>$^1$H NMR(400MHz, METHANOL-D4) δppm 1.5(m, 1H), 1.8(m, 1H), 2.0(d, J=12.2Hz, 2H), 2.4(m, 1H), 3.0(m, 2H), 3.4(d, J=12.9Hz, 1H), 3.6(d, J=15.9Hz, 1H), 4.3(m, 1H), 4.5(m, 1H), 6.2(s, 2H), 7.3(m, 2H), 7.4(m, J=25.4Hz, 3H), 7.5(m, 1H), 7.6(m, 1H). |
| 56 | 1-(2,4-Difluoro-phenyl)-5-fluoro-3-(piperidin-4-yloxy)-1H-indazole hydrochloride | MS(APCI)M+1=348.1<br>Found for $C_{18}H_{16}F_3N_3O1$•1.0 HCl•0.12 $H_2O$; C, 55.62; H, 4.31; N, 10.61; F, 14.57; Cl, 9.11<br>$^1$H NMR(400MHz, DMSO-D$_6$) δppm 2.1(m, 2H), 2.2(m, 2H), 3.1(m, 2H), 3.3(m, 2H), 5.1(m, 1H), 7.3(m, 2H), 7.4(td, J=9.0, 2.4Hz, 1H), 7.6(m, 2H), 7.7(td, J=8.8, 6.0Hz, 1H), 8.9(bs, 2H). |
| 57 | (±)-5-Fluoro-1-(2-fluoro-phenyl)-3-(piperidin-3-ylmethoxy)-1H-indazole hydrochloride | MS(APCI)M+1=344.1<br>Found for $C_{19}H_{19}F_2N_3O1$•1.0 HCl•0.29 $H_2O$; C, 58.87; H, 5.23; N, 10.87; F, 9.62; Cl, 9.49<br>$^1$H NMR(400MHz, DMSO-D6) δppm 1.4(m, 1H), 1.8(m, 3H), 2.4(m, 1H), 2.8(m, 2H), 3.2(d, J=12.2Hz, 1H), 3.4(dd, J=12.3, 3.0Hz, 1H), 4.3(dd, J=10.4, 7.0Hz, 1H), 4.4(m, 1H), 7.4(m, 3H), 7.5(m, 2H), 7.6(dd, J=8.4, 2.1Hz, 1H), 7.6(m, 1H), 9.1(bs, 2H). |
| 58 | 5-Chloro-1-(2,5-difluoro-phenyl)-3-(piperidin-4-yloxy)-1H-indazole hydrochloride | MS(APCI)M+1=364.1<br>$^1$H NMR(400MHz, DMSO-D$_6$) δppm 2.1(m, 2H), 2.2(m, 2H), 2.3(d, J=3.9Hz, 1H), 3.1(ddd, J=12.4, 8.1, 3.9Hz, 2H), 3.3(m, 2H), 5.1(ddd, J=7.2, 3.8, 3.7Hz, 1H), 7.4(m, 2H), 7.5(m, 3H), 7.9(d, J=1.5Hz, 1H), 9.1(s, 2H) |
| 59 | 7-Methyl-1-phenyl-3-(piperidin-4-yloxy)-1H-indazole hydrochloride | MS(APCI)M+1=308.2<br>$^1$H NMR(400MHz, DMSO-D6) δppm 2.0(m, 5H), 2.2(m, 2H), 3.1(td, J=8.7, 4.4Hz, 2H), 3.2(m, 2H), 5.0(ddd, J=7.7, 4.0, 3.9Hz, 1H), 7.0(m, 1H), 7.2(d, J=7.1Hz, 1H), 7.5(m, 5H), 7.5(d, J=7.8Hz, 1H), 8.7(s, 2H) |
| 60 | 7-Methoxy-1-phenyl-3-(piperidin-4-yloxy)-1H-indazole hydrochloride | MS(APCI)M+1=324.2<br>$^1$H NMR(400MHz, DMSO-D6) δppm 2.0(m, 2H), 2.2(ddd, J=10.4, 7.1, 3.5Hz, 2H), 3.1(ddd, J=12.7, 8.7, 3.5Hz, 2H), 3.2(m, 2H), 3.7(s, 3H), 5.0(m, 1H), 7.0(d, J=7.1Hz, 1H), 7.1(t, J=7.8Hz, 1H), 7.3(m, 2H), 7.4(m, 4H), 8.9(s, 2H) |
| 61 | 7-Chloro-1-phenyl-3-(piperidin-4-yloxy)-1H-indazole hydrochloride | MS(APCI)M+1=328.1<br>$^1$H NMR(400MHz, DMSO-D6) δppm 2.0(m, 2H), 2.2(m, 2H), 3.1(m, 2H), 3.3(m, 2H), 5.1(dt, J=7.6, 3.9Hz, 1H), 7.2(m, 1H), 7.4(m, 5H), 7.5(m, 1H), 7.7(dd, J=8.1, 1.0Hz, 1H), 8.8(s, 2H) |
| 62 | 4-Methyl-1-phenyl-3-(piperidin-4-yloxy)-1H-indazole hydrochloride | MS(APCI)M+1=308.2<br>$^1$H NMR(400MHz, DMSO-D6) δppm 2.1(m, 2H), 2.3(m, 2H), 2.6(s, 3H), 3.2(m, 4H), 5.2(dt, J=6.6, 3.4Hz, 1H), 6.9(d, J=7.1Hz, 1H), 7.3(m, 2H), 7.5(m, 3H), 7.7(dt, J=8.6, 1.7Hz, 2H), 9.0(s, 2H) |
| 63 | 6-Fluoro-1-(2-fluoro-phenyl)-3-(piperidin-4-yloxy)-1H-indazole hydrochloride | MS(APCI)M+1=330.1<br>$^1$H NMR(400MHz, DMSO-D6) δppm 2.0(m, 2H), 2.2(ddd, J=10.3, 7.1, 3.7Hz, 2H), 3.1(m, 2H), 3.2(m, 2H), 5.1(ddd, J=7.7, 4.0, 3.9Hz, 1H), 7.1(m, 2H), 7.3(m, 1H), 7.5(m, 2H), 7.6(m, 1H), 7.8(dd, J=8.8, 5.4Hz, 1H), 9.0(s, 2H) |
| 64 | 6-Chloro-1-phenyl-3-(piperidin-4-yloxy)-1H-indazole hydrochloride | MS(APCI)M+1=328.1<br>$^1$H NMR(400MHz, DMSO-D6) δppm 2.0(m, J=14.2, 7.3, 3.7, 3.5Hz, 2H), 2.2(m, 2H), 3.1(m, 2H), 3.3(m, 2H), 5.1(dt, J=7.3, 3.6Hz, 1H), 7.3(m, 1H), 7.5(m, 3H), 7.7(dt, J=8.7, 1.6Hz, 2H), 7.8(d, J=9.8Hz, 1H), 7.8(d, J=1.5Hz, 1H), 8.9(s, 2H) |
| 65 | 1-(2-fluorophenyl)-3-(piperidin-4-yloxy)-7-(trifluoromethyl)-1H-indazole hydrochloride | MS(APCI)M+1=380.1<br>$^1$H NMR(400MHz, DMSO-D6) δppm 2.0(m, 2H), 2.2(m, 2H), 3.1(m, 2H), 3.2(m, 2H), 5.0(ddd, J=7.8, 4.2, 4.0Hz, 1H), 7.3(m, 3H), 7.6(m, J=7.7, 7.7, 5.7, 1.8Hz, 2H), 7.8(d, J=7.3Hz, 1H), 8.1(d, J=7.8Hz, 1H), 8.9(s, 2H) |
| 66 | (±)-1-(3-Fluoro-phenyl)-3-(piperidin-3-ylmethoxy)-1H-indazole hydrochloride | MS(APCI)M+1=326.2<br>$^1$H NMR(400MHz, DMSO-D6) δppm 1.4(m, 1H), 1.7(m, 1H), 1.9(m, 2H), 2.4(m, 1H), 2.8(m, 2H), 3.2(m, 1H), 3.4(dd, J=12.2, 3.4Hz, 1H), 4.3(dd, J=10.5, 7.1Hz, 1H), 4.4(m, 1H), 7.1(m, 1H), 7.2(m, 1H), 7.6(m, 4H), 7.8(d, J=7.8Hz, 1H), 7.9(d, J=8.8Hz, 1H), 8.7(s, 1H) |
| 67 | (±)-1-(4-Fluoro-phenyl)-3-(piperidin-3-ylmethoxy)-1H-indazole hydrochloride | MS(APCI)M+1=326.2<br>$^1$H NMR(400MHz, DMSO-D6) δppm 1.4(m, 1H), 1.7(m, 1H), 1.8(m, 2H), 2.4(m, 1H), 2.8(m, 2H), 3.2(m, 1H), 3.4(dd, J=12.2, 4.1Hz, 1H), 4.3(dd, J=10.5, 7.1Hz, 1H), 4.4(m, 1H), 7.2(m, 1H), 7.4(m, 2H), 7.5(ddd, J=8.5, 7.1, 1.2Hz, 1H), 7.7(m, 4H), 8.7(s, 2H) |

-continued

| Ex. # | NAME | MS MP (° C.) CHN NMR and [α]$_D^{24}$ |
|---|---|---|
| 68 | (±)-1-(4-Chloro-phenyl)-3-(piperidin-3-ylmethoxy)-1H-indazole hydrochloride | MS(APCI)M+1=342.2<br>$^1$H NMR(400MHz, DMSO-D6) δppm 1.4(qd, J=12.3, 3.8Hz, 1H), 1.7(m, 1H), 1.8(m, 2H), 2.4(m, 1H), 2.8(m, 2H), 3.2(d, J=12.2Hz, 1H), 3.4(dd, J=12.5, 3.4Hz, 1H), 4.3(dd, J=10.5, 7.1Hz, 1H), 4.4(m, 1H), 7.2(m, 1H), 7.5(m, 3H), 7.7(m, 3H), 7.8(d, J=8.5Hz, 1H), 8.8(s, 2H) |
| 69 | (±)-5-Chloro-1-phenyl-3-(piperidin-3-ylmethoxy)-1H-indazol hydrochloride | MS(APCI)M+1=342.2<br>$^1$H NMR(400MHz, DMSO-D6) δppm 1.4(m, 1H), 1.6(m, 1H), 1.8(m, 2H), 2.3(m, 1H), 2.8(m, 2H), 3.2(m, 1H), 3.4(dd, J=12.2, 3.7Hz, 1H), 4.3(dd, J=10.5, 7.1Hz, 1H), 4.4(m, 1H), 7.3(m, 1H), 7.5(m, 3H), 7.7(ddd, J=8.7, 1.7, 1.6Hz, 2H), 7.8(m, 2H), 8.7(s, 2H) |
| 70 | (±)-6-Fluoro-1-(2-fluoro-phenyl)-3-(piperidin-3-ylmethoxy)-1H-indazole hydrochloride | MS(APCI)M+1=344.1<br>$^1$H NMR(400MHz, DMSO-D6) δppm 1.4(td, J=12.2, 8.5Hz, 1H), 1.7-1.8(m, 3H), 2.4(d, J=9.8Hz, 1H), 2.8(m, 2H), 3.2(d, J=12.0Hz, 1H), 3.3(s, 1H), 3.4(m, 1H), 4.3(dd, J=10.5, 7.1Hz, 1H), 4.3(m, 1H), 7.1(m, 2H), 7.4(m, 1H), 7.5(m, 2H), 7.6(t, J=7.9Hz, 1H), 7.8(dd, J=8.8, 5.1Hz, 1H), 9.0(s, 2H) |
| 71 | 6-Methyl-1-phenyl-3-(piperidin-4-yloxy)-1H-indazole hydrochloride | MS(APCI)M+1=308.2<br>$^1$H NMR(400MHz, DMSO-D6) δppm 2.0(m, 2H), 2.3(m, 2H), 2.4(s, 3H), 3.1(ddd, J=12.7, 8.7, 3.8Hz, 2H), 3.3(m, 2H), 5.1(ddd, J=7.4, 3.9, 3.8Hz, 1H), 7.0(d, J=8.3Hz, 1H), 7.3(m, 1H), 7.5(m, 2H), 7.6(s, 1H), 7.6(d, J=8.3Hz, 1H), 7.7(dt, J=8.6, 1.7Hz, 2H), 8.8(s, 2H) |
| 72 | 1-(2-Fluoro-phenyl)-6-methyl-3-(piperidin-4-yloxy)-1H-indazole hydrochloride | MS(APCI)M+1=326.2<br>$^1$H NMR(400MHz, DMSO-D6) δppm 2.0(m, 2H), 2.3(ddd, J=10.4, 7.1, 3.3Hz, 2H), 2.4(s, 3H), 3.1(ddd, J=12.6, 8.7, 3.7Hz, 2H), 3.3(dd, J=7.7, 4.5Hz, 2H), 5.1(ddd, J=7.7, 4.0, 3.9Hz, 1H), 7.0(m, 2H), 7.4(ddd, J=8.4, 5.4, 3.1Hz, 1H), 7.5(m, 2H), 7.6(m, 2H), 8.8(s, 2H) |
| 73 | 5-Chloro-1-(2-fluoro-phenyl)-3-(piperidin-3-ylmethoxy)-1H-indazole hydrochloride | Found for C$_{19}$H$_{19}$ClFN$_3$O•0.6HCl: C, 54.94; H, 4.54; N, 9.92.<br>$^1$H NMR(400MHz, DMSO-D6) δppm 1.4(m, 1H), 1.7(m, 1H), 1.8(m, 2H), 2.3(m, 1H), 2.8(m, 2H), 3.2(m, 1H), 3.4(m, 1H), 4.3(m, 1H), 4.4(m, 1H), 7.4(m, 2H), 7.5(m, 3H), 7.8(s, 1H), 8.9(s, 2H). |
| 74 | 1-(2-Fluoro-phenyl)-6-methyl-3-(piperidin-3-ylmethoxy)-1H-indazole hydrochloride | MS(APCI)M+1=340.2<br>$^1$H NMR(400MHz, DMSO-D6) δppm 1.4(m, 1H), 1.7(m, 1H), 1.8(m, 2H), 2.3(m, 1H), 2.4(m, 3H), 2.8(m, 2H), 3.2(m, 1H), 3.4(m, 1H), 4.2(dd, J=10.5, 7.1Hz, 1H), 4.3(m, 1H), 7.0(dd, J=8.3, 0.7Hz, 1H), 7.0(d, J=3.4Hz, 1H), 7.4(m, 1H), 7.5(m, 2H), 7.6(t, J=7.9Hz, 2H), 8.8(s, 2). |
| 75 | 5,6-Difluoro-1-(2-fluoro-phenyl)-3-(piperidin-4-yloxy)-1H-indazole hydrochloride | MS(APCI)M+1=348.1<br>$^1$H NMR(400MHz, DMSO-D6) δppm 2.0(m, 2H), 2.2(m, 2H), 3.1(m, 2H), 5.1(m, 1H), 7.4(m, 1H), 7.5(m, 3H), 7.6(m, 1H), 7.9(m, 1H), 8.8(m, 2H). |
| 76 | 5,6-Difluoro-1-(2-fluoro-phenyl)-3-(piperidin-3-ylmethoxy)-1H-indazole hydrochloride | MS(APCI)M+1=362.1<br>$^1$H NMR(400MHz, DMSO-D6) δppm 1.4(m, 1H), 1.7(m, 1H), 1.8(m, 2H), 2.8(s, 2H), 3.4(s, 1H), 4.3(m, 2H), 7.36-7.52(m, 5H), 7.60-7.64(m, 1H), 7.81-7.64(m, 1H), 8.7(s, 2H). |
| 77 | 5-Fluoro-1-(3-fluoro-phenyl)-3-(piperidin-4-yloxy)-1H-indazole hydrochloride | MS(APCI)M+1=330.1<br>$^1$H NMR(400MHz, DMSO-D6) δppm 2.1(m, 2H), 2.3(m, 2H), 3.1(m, 2H), 3.3(m, 2H), 5.2(dt, J=7.4, 3.8Hz, 1H), 7.1(m, 1H), 7.4(td, J=9.2, 2.7Hz, 1H), 7.6(m, 4H), 7.9(dd, J=9.3, 3.9Hz, 1H), 8.8(s, 2H). |
| 78 | (S)-5-Fluoro-1-(3-fluoro-phenyl)-3-(piperidin-3-ylmethoxy)-1H-indazole hydrochloride | MS(APCI)M+1=344.1<br>$^1$H NMR(400MHz, DMSO-D6) δppm 1.4(m, 1H), 1.7(m, 1H), 1.8(m, 2H), 2.4(m, 1H), 2.8(m, 2H), 3.2(m, 1H), 3.4(dd, J=12.4, 3.2Hz, 1H), 4.3(dd, J=10.5, 7.1Hz, 1H), 4.4(m, 1H), 7.1(m, 1H), 7.4(td, J=9.2, 2.4Hz, 1H), 7.6(m, 4H), 7.9(dd, J=9.3, 3.9Hz, 1H), 8.9(s, 2H). |
| 79 | 5-Fluoro-1-(4-fluoro-phenyl)-3-(piperidin-4-yloxy)-1H-indazole hydrochloride | MS(APCI)M+1=330.1<br>$^1$H NMR(400MHz, DMSO-D6) δppm 2.0(m, 2H), 2.2(m, 2H), 3.1(m, 2H), 3.3(m, 2H), 5.1(ddd, J=7.4, 3.9, 3.8Hz, 1H), 7.4(m, 3H), 7.6(dd, J=8.4, 2.1Hz, 1H), 7.7(m, 3H), 8.7(s, 2H). |
| 80 | (S)-5-Fluoro-1-(4-fluoro-phenyl)-3-(piperidin-3-ylmethoxy)-1H-indazole hydrochloride | MS(APCI)M+1=344.1<br>$^1$H NMR(400MHz, DMSO-D6) δppm 1.4(m, 1H), 1.7(m, 1H), 1.8(m, 2H), 2.3(m, 1H), 2.8(q, J=11.5Hz, 2H), 3.2(d, J=12.5Hz, 1H), 3.4(m, 1H), 4.3(dd, J=10.5, 7.1Hz, 1H), 4.4(m, 1H), 7.4(m, 3H), 7.5(dd, J=8.3, 2.4Hz, 1H), 7.7(m, 3H), 8.8(s, 2H). |
| 81 | 4-Fluoro-1-(3-fluoro-phenyl)-3-(piperidin-4-yloxy)-1H-indazole | MS(APCI)M+1=330.1<br>$^1$H NMR(400MHz, DMSO-D6) δppm 2.0(m, 2H), 2.3(m, 2H), 3.1(m, 2H), 3.2(m, 2H), 5.2(ddd, J=7.7, 4.0, 3.9Hz, 1H), |

-continued

| Ex. # | NAME | MS MP (° C.) CHN NMR and $[\alpha]_D^{24}$ |
|---|---|---|
|  | hydrochloride | 7.0(dd, J=10.4, 7.7Hz, 1H), 7.2(m, 1H), 7.5(m, 2H), 7.6(dt, J=6.9, 1.7Hz, 2H), 7.6(d, J=8.5Hz, 1H), 8.9(s, 2H). |
| 82 | (S)-4-Fluoro-1-(3-fluoro-phenyl)-3-(piperidin-3-ylmethoxy)-1H-indazole hydrochloride | MS(APCI)M+1=344.1<br>$^1$H NMR(400MHz, DMSO-D6) δppm 1.4(m, 1H), 1.7(m, 1H), 1.8(m, 2H), 2.4(m, 1H), 2.8(m, 2H), 3.2(d, J=12.5Hz, 1H), 3.4(m, 1H), 4.3(m, 2H), 7.0(dd, J=10.3, 7.8Hz, 1H), 7.2(m, 1H), 7.5(m, 4H), 7.6(d, J=8.5Hz, 1H), 9.0(s, 2H). |
| 83 | 4-Fluoro-1-(4-fluoro-phenyl)-3-(piperidin-4-yloxy)-1H-indazole hydrochloride | MS(APCI)M+1=330.2<br>$^1$H NMR(400MHz, DMSO-D6) δppm 2.0(m, 2H), 2.2(m, 2H), 3.1(m, 2H), 3.2(m, 2H), 5.1(m, 1H), 6.9(m, 1H), 7.4(m, 2H), 7.4(m, 2H), 7.7(m, 2H), 8.8(s, 2H). |
| 84 | (S)-4-Fluoro-1-(4-fluoro-phenyl)-3-(piperidin-3-ylmethoxy)-1H-indazole hydrochloride | MS(APCI)M+1=344.2<br>$^1$H NMR(400MHz, DMSO-D6) δppm 1.3(m, 1H), 1.6(m, 1H), 1.8(m, 2H), 2.3(m, 1H), 2.8(m, 2H), 3.2(m, 1H), 3.3(m, 1H), 4.3(dd, J=10.5, 7.3Hz, 1H), 4.3(m, 1H), 6.9(m, 1H), 7.4(m, 2H), 7.4(m, 2H), 7.7(m, 2H), 8.7(s, 1H). |
| 85 | (S)-4-Fluoro-1-(2-fluoro-phenyl)-3-(piperidin-3-ylmethoxy)-1H-indazole hydrochloride | MS(APCI)M+1=344.2<br>$^1$H NMR(400MHz, DMSO-D6) δppm 1.3(m, 1H), 1.7(m, 1H), 1.8(m, 2H), 2.3(m, 1H), 2.7(m, 2H), 3.2(d, J=12.5Hz, 1H), 3.3(m, 1H), 4.2(dd, J=10.5, 7.3Hz, 1H), 4.3(m, 1H), 6.9(dd, J=10.5, 7.8Hz, 1H), 7.0(dd, J=8.4, 3.3Hz, 1H), 7.4(m, 2H), 7.5(m, 2H), 7.6(td, J=7.9, 1.5Hz, 1H), 8.8(s, 1H). |
| 86 | 5,6-Difluoro-1-phenyl-3-(piperidin-3-ylmethoxy)-1H-indazole hydrochloride | MS(APCI)M+1=344.2<br>$^1$H NMR(400MHz, DMSO-D6) δppm 1.4(m, 1H), 1.7(m, 1H), 1.8(m, 2H), 2.4(m, 1H), 2.8(m, 2H), 3.2(m, 1H), 3.4(m, 1H), 4.3(m, 1H), 4.4(m, 1H), 7.3(m, 1H), 7.5(m, 2H), 7.7(m, 2H), 7.9(m, 2H), 8.9(br s, 2H). |
| 87 | 5,6-Difluoro-1-phenyl-3-(piperidin-4-yloxy)-1H-indazole hydrochloride | MS(APCI)M+1=330.2<br>$^1$H NMR(400MHz, DMSO-D6) δppm 2.1(m, 2H), 2.3(m, 2H), 3.1(m, 2H), 3.3(m, 2H), 5.1(m, 1H), 7.3(m, 1H), 7.5(m, 2H), 7.7(m, 2H), 7.9(m, 2H), 9.0(br s, 2H). |
| 88 | 1-(2,4-Difluoro-phenyl)-4-fluoro-3-(piperidin-4-yloxy)-1H-indazole hydrochloride | MS(APCI)M+1=348.2<br>$^1$H NMR(400MHz, DMSO-D6) δppm 2.0(m, 2H), 2.2(m, 2H), 3.1(m, 2H), 3.2(m, 2H), 5.1(m, 1H), 7.0(dd, J=10.5, 7.8Hz, 1H), 7.1(dd, J=8.5, 2.7Hz, 1H), 7.3(m, 1H), 7.4(td, J=8.2, 5.1Hz, 1H), 7.6(ddd, J=11.2, 8.8, 2.9Hz, 1H), 7.7(td, J=8.8, 6.0Hz, 1H), 8.7(s, 1H). |
| 89 | (S)-1-(2,4-Difluoro-phenyl)-4-fluoro-3-(piperidin-3-ylmethoxy)-1H-indazole hydrochloride | MS(APCI)M+1=362.2<br>$^1$H NMR(400MHz, DMSO-D6) δppm 1.4(m, 1H), 1.6(m, 1H), 1.8(m, 2H), 2.3(m, 1H), 2.8(t, J=12.1Hz, 2H), 3.2(m, 1H), 3.4(m, 1H), 4.3(dd, J=10.5, 7.3Hz, 1H), 4.3(m, 1H), 7.0(dd, J=10.6, 7.4Hz, 1H), 7.1(dd, J=8.4, 2.8Hz, 1H), 7.3(m, 1H), 7.4(td, J=8.2, 5.1Hz, 1H), 7.6(m, 1H), 7.7(td, J=8.9, 5.9Hz, 1H), 8.5(s, 1H). |
| 90 | 1-(2,5-Difluoro-phenyl)-4-fluoro-3-(piperidin-4-yloxy)-1H-indazole hydrochloride | MS(APCI)M+1=348.2<br>$^1$H NMR(400MHz, DMSO-D6) δppm 2.0(m, 2H), 2.3(m, 2H), 3.1(m, 2H), 3.2(m, 2H), 5.1(m, 1H), 7.0(dd, J=10.5, 7.6Hz, 1H), 7.2(dd, J=8.4, 3.5Hz, 1H), 7.4(m, 1H), 7.5(m, J=8.2, 5.1Hz, 1H), 7.6(m, 2H), 8.6(s, 1H). |
| 91 | (S)-1-(2,5-Difluoro-phenyl)-4-fluoro-3-(piperidin-3-ylmethoxy)-1H-indazole hydrochloride | MS(APCI)M+1=362.2<br>$^1$H NMR(400MHz, DMSO-D6) δppm 1.3(m, 1H), 1.6(m, 1H), 1.8(m, 2H), 2.3(m, 1H), 2.7(t, J=11.7Hz, 2H), 3.2(m, 1H), 3.4(m, 1H), 4.3(m, 2H), 7.0(dd, J=10.5, 7.6Hz, 1H), 7.1(dd, J=8.5, 3.4Hz, 1H), 7.4(m, 1H), 7.4(td, J=8.2, 5.1Hz, 1H), 7.5(m, 2H), 8.5(s, 1H). |
| 92 | (R)-1-(2,4-Difluoro-phenyl)-4-fluoro-3-(pyrrolidin-3-ylmethoxy)-1H-indazole hydrochloride | MS(APCI)M+1=348.2<br>$^1$H NMR(400MHz, DMSO-D6) δppm 1.8(m, 1H), 2.1(m, 1H), 2.8(ddd, J=14.5, 7.2, 7.1Hz, 1H), 3.0(dd, J=11.7, 7.1Hz, 1H), 3.2(m, 1H), 3.2(m, 2H), 4.4(ddd, J=17.6, 10.4, 7.0Hz, 2H), 6.9(dd, J=10.4, 7.7Hz, 1H), 7.1(dd, J=8.5, 2.7Hz, 1H), 7.3(m, 1H), 7.4(td, J=8.2, 5.1Hz, 1H), 7.6(ddd, J=11.1, 8.8, 2.8Hz, 1H), 7.7(td, J=8.9, 6.1Hz, 1H), 9.2(s, 1H). |
| 93 | (R)-1-(2,5-Difluoro-phenyl)-4-fluoro-3-(pyrrolidin-3-ylmethoxy)-1H-indazole hydrochloride | MS(APCI)M+1=348.2<br>$^1$H NMR(400MHz, DMSO-D6) δppm 1.8(m, 1H), 2.1(m, 1H), 2.9(m, 1H), 3.0(dd, J=11.6, 7.2Hz, 1H), 3.2(m, 1H), 3.3(m, 2H), 4.4(ddd, J=17.2, 10.3, 7.0Hz, 2H), 7.0(dd, J=10.5, 7.8Hz, 1H), 7.1(dd, J=8.5, 3.7Hz, 1H), 7.4(m, 1H), 7.5(td, J=8.2, 5.1Hz, 1H), 7.6(m, 2H), 9.2(s, 1H). |
| 94 | (S)-1-(2,4-Difluoro-phenyl)-4-fluoro-3-(morpholin-2-ylmethoxy)-1H-indazole hydrochloride | 172-174° C.<br>Found for $C_{18}H_{16}F_3N_3O_2$•1.0 HCl; C, 53.94; H, 4.08; N, 10.31; F, 14.03; Cl, 8.76<br>$[\alpha]_D^{24}$=+1.8 degrees(MeOH, c=8.4) |

-continued

| Ex. # | NAME | MS MP (° C.) CHN NMR and $[\alpha]_D^{24}$ |
|---|---|---|
| 95 | (S)-1-(2,5-Difluoro-phenyl)-4-fluoro-3-(morpholin-2-ylmethoxy)-1H-indazole hydrochloride | 190-192° C.<br>Found for $C_{18}H_{16}F_3N_3O_2 \cdot 1.0$ HCl: C, 54.04; H, 3.98; N, 10.31; F, 14.08; Cl, 8.84<br>$[\alpha]_D^{24}$=+3.7 degrees(MeOH, c=8.4) |
| 96 | (±)-1-(3,4-Difluoro-phenyl)-5-fluoro-3-(piperidin-3-ylmethoxy)-1H-indazole hydrochloride | MS(APCI)M+1=362.2<br>Found for $C_{19}H_{18}F_3N_3O1 \cdot 1.0$ HCl; C, 57.19; H, 4.79; N, 10.42; F, 13.95; Cl, 8.95<br>$^1$H NMR(400MHz, CD3CN) δppm 1.5(m, 1H), 1.7(m, 1H), 1.9(m, 2H), 2.4(m, 1H), 2.9(m, 2H), 3.3(m, 1H), 3.5(m, 1H), 4.3(m, 1H), 4.4(m, 1H), 7.3(td, J=9.2, 2.6Hz, 1H), 7.4(m, 3H), 7.6(m, 1H), 7.7(dd, J=9.3, 3.9Hz, 1H). |
| 97 | 1-(3,4-Difluoro-phenyl)-5-fluoro-3-(piperidin-4-yloxy)-1H-indazole hydrochloride | MS(APCI)M+1=348.1<br>Found for $C_{18}H_{16}F_3N_3O1 \cdot 1.1$ HCl•0.35 H$_2$O; C, 54.58; H, 4.17; N, 10.51; F, 14.08; Cl, 9.15<br>$^1$H NMR(400MHz, DMSO-D6) δppm 2.1(m, 2H), 2.3(m, 2H), 3.1(m, 2H), 3.3(m, 2H), 5.2(m, 1H), 7.4(td, J=9.2, 2.4Hz, 1H), 7.6(m, 3H), 7.8(m, 1H), 7.9(dd, J=9.0, 3.9Hz, 1H), 9.0(bs, 2H). |
| 98 | (S)-(+)-4-Fluoro-1-(2-fluorophenyl)-3-(morpholin-2-ylmethoxy)-1H-indazole maleate | 139-140° C.<br>Found for $C_{18}H_{17}F_2N_3O_2 \cdot C_4H_4O_4$: C, 57.54; H, 4.51; N, 9.04; F, 8.60<br>$[\alpha]_D^{24}$=+3.2 degrees(MeOH, c=7.6) |
| 99 | 5-Fluoro-3-(piperidin-3-ylmethoxy)-1-pyridin-2-yl-1H-indazole hydrochloride | MS(APCI)M+1=327.2<br>$^1$H NMR(400MHz, DMSO-D6) δppm 1.4(m, 1H), 1.7(m, 1H), 1.9(m, 2H), 2.4(m, 1H), 2.8(m, 2H), 3.2(m, 1H), 3.4(m, 1H), 4.3(dd, J=10.5, 7.1Hz, 1H), 4.4(m, 1H), 7.2(ddd, J=6.7, 5.6, 1.0Hz, 1H), 7.5(td, J=9.2, 2.6Hz, 1H), 7.6(dd, J=8.2, 2.6Hz, 1H), 7.8(d, J=8.3Hz, 1H), 7.9(m, 1H), 8.5(m, 1H), 8.7(dd, J=9.2, 4.5Hz, 1H), 8.8(m, 1H), 9.0(m, 1H). |
| 100 | 4-Fluoro-1-(2-fluoro-phenyl)-3-(piperidin-4-yloxy)-1H-indazole hydrochloride | MS(APCI)M+1=330.1<br>$^1$H NMR(400MHz, DMSO-D6) δppm 2.0(m, 2H), 2.3(d, J=13.7Hz, 2H), 3.1(ddd, J=12.8, 8.7, 3.7Hz, 2H), 3.2(m, 2H), 5.1(dt, J=7.9, 4.0Hz, 1H), 6.9(dd, J=10.5, 7.8Hz, 1H), 7.1(dd, J=8.4, 3.1Hz, 1H), 7.4(m, 2H), 7.5(m, 2H), 7.6(m, 1H), 8.9(s, 2H) |
| 101 | 5-Chloro-1-phenyl-3-(piperidin-4-yloxy)-1H-indazole hydrochloride | MS(APCI)M+1=328.1<br>$^1$H NMR(400MHz, DMSO-D6) δppm 2.1(m, 2H), 2.2(m, 2H), 3.1(m, 2H), 3.3(m, 2H), 5.1(dt, J=7.1, 3.5Hz, 1H), 7.3(t, J=7.3Hz, 1H), 7.5(m, 3H), 7.7(m, 2H), 7.8(d, J=9.0Hz, 1H), 7.9(d, J=1.5Hz, 1H), 8.9(s, 2H) |
| 102 | 5-Chloro-1-(2-fluoro-phenyl)-3-(piperidin-4-yloxy)-1H-indazole hydrochloride | MS(APCI)M+1=346.1<br>$^1$H NMR(400MHz, DMSO-D6) δppm 2.0(m, 2H), 2.2(m, 2H), 3.1(ddd, J=12.4, 8.0, 3.8Hz, 2H), 3.3(dd, J=8.1, 3.9Hz, 2H), 5.1(m, 1H), 7.3(dd, J=9.0, 3.4Hz, 1H), 7.4(ddd, J=8.3, 5.3, 3.3Hz, 1H), 7.5(m, 3H), 7.6(t, J=7.8Hz, 1H), 7.9(d, J=2.2Hz, 1H), 9.0(s, 2H) |
| 103 | 4-Fluoro-1-phenyl-3-(piperidin-4-yloxy)-1H-indazole hydrochloride | MS(APCI)M+1=312.1<br>$^1$H NMR(400MHz, DMSO-D6) δppm 2.1(m, 2H), 2.3(m, 2H), 3.1(ddd, J=12.7, 8.7, 3.5Hz, 2H), 3.2(m, 2H), 5.1(ddd, J=7.4, 4.2, 3.8Hz, 1H), 6.9(dd, J=10.5, 7.8Hz, 1H), 7.3(t, J=7.4Hz, 1H), 7.4(td, J=8.2, 5.1Hz, 1H), 7.5(m, 3H), 7.7(m, 2H), 8.9(s, 2H) |
| 104 | (S)-(−)-1-Phenyl-3-(piperidin-3-ylmethoxy)-1H-pyrazolo[3,4-b]pyridine hydrochloride | MS(APCI)M+1=309<br>247-249° C.<br>Found for $C_{18}H_{20}N_4O \cdot HCl$: C, 62.41; H, 5.96; N, 16.01; Cl, 10.50<br>$[\alpha]_D^{24}$=−14.3 degrees(MeOH, c=5.3) |
| 105 | (S)-(+)-3-(Morpholin-2-ylmethoxy)-1-phenyl-1H-pyrazolo[3,4-b]pyridine hydrochloride | MS(APCI)M+1=311<br>109-115° C.(dec)<br>Found for $C_{17}H_{18}N_4O_2 \cdot HCl \cdot 0.25H_2O$: C, 58.07; H, 5.52; N, 15.86; Cl, 10.06<br>$[\alpha]_D^{24}$=+5.7 degrees(MeOH, c=7.2) |
| 106 | 1-(2-Fluorophenyl)-3-(piperidin-4-yloxy)-1H-indazole L-tartrate | MS(APCI)M+1=150, 311<br>$^1$H NMR(DMSO) δppm 7.7(d, 1H), 7.6(t, 1H), 7.47.5(m, 3H), 7.3-7.4(m, 1H), 7.25(m, 1H), 7.2(t, 1H), 5.1(m, 1H), 3.3(m, 2H), 3.1(m, 2H), 2.2(m, 2H), 2.0(m, 2H). |
| 107 | (S)-5-Fluoro-1-(2-fluorophenyl)-3-(piperidin-3-ylmethoxy)-1H-indazole L-tartrate | MS(APCI)M+1=344<br>181-182° C. |
| 108 | 1-(2,6-Difluoro-phenyl)-5-fluoro-3- | MS(APCI)M+1=348.2<br>$^1$H NMR(400MHz, DMSO-D6) δppm 2.0(m, 2H), 2.2(m, 2H), |

| Ex. # | NAME | MS MP (° C.) CHN NMR and $[\alpha]_D^{24}$ |
|---|---|---|
| | (piperidin-4-yloxy)-1H-indazole hydrochloride | 3.1(m, 2H), 3.3(m, 2H), 5.1(m, 1H), 7.3(dd, J=9.0, 3.7Hz, 1H), 7.4(m, 3H), 7.6(m, 2H), 8.9(bs, 2H). |
| 109 | 1-(2,6-Difluoro-phenyl)-4-fluoro-3-(piperidin-4-yloxy)-1H-indazole hydrochloride | MS(APCI)M+1=348.2<br>$^1$H NMR(400MHz, DMSO-D6) δppm 2.0(m, 2H), 2.3(m, 2H), 3.1(m, 2H), 3.2(m, 2H), 5.1(m, 1H), 7.0(dd, J=10.4, 7.7Hz, 1H), 7.5(td, J=8.2, 5.1Hz, 1H), 7.6(m, 3H), 7.8(ddd, J=11.8, 7.2, 2.2Hz, 1H), 8.9(s, 1H). |
| 110 | (S)-1-(2,6-Difluoro-phenyl)-4-fluoro-3-(piperidin-3-ylmethoxy)-1H-indazole hydrochloride | MS(APCI)M+1=362.2<br>$^1$H NMR(400MHz, DMSO-D6) δppm 1.3(m, 1H), 1.7(m, 1H), 1.8(m, 2H), 2.4(m, 1H), 2.8(t, J=12.0Hz, 2H), 3.2(m, 1H), 3.4(m, 1H), 4.3(m, 2H), 7.0(dd, J=10.3, 7.6Hz, 1H), 7.5(m, 1H), 7.6(m, 3H), 7.8(ddd, J=11.8, 7.1, 2.1Hz, 1H), 8.8(s, 1H). |
| 111 | (S)-1-(2,6-Difluoro-phenyl)-5-fluoro-3-(piperidin-3-ylmethoxy)-1H-indazole hydrochloride | MS(APCI)M+1=362.2<br>$^1$H NMR(400MHz, DMSO-D6) δppm 1.4(m, 1H), 1.7(m, 1H), 1.9(m, 2H), 2.3(m, 1H), 2.8(m, 2H), 3.2(d, J=12.9Hz, 1H), 3.4(dd, J=12.6, 3.0Hz, 1H), 4.3(m, 2H), 7.3(dd, J=9.2, 3.8Hz, 1H), 7.4(m, 3H), 7.6(m, 2H), 9.0(bs, 2H). |

Example 112

1-(2-Fluoro-phenyl)-3-(piperidin-4-yloxy)-1H-indazole, L-tartrate

A. Preparation of 4-methanesulfonyloxy-piperidine-1-carboxylic acid tert-butyl ester A stirred solution of 250 g (1.24 mole) of 4-hydroxy-piperidine-1-carboxylic acid tert-butyl ester in 2.3 L of dichloromethane was cooled to −10° C. 188 g (1.86 mole) of triethylamine was added in a narrow stream over a 20 minute period. There was no significant temperature change. The resulting solution was stirred at −10° C. for 30 minutes and then 172 g (1.50 mole) of methanesulfonyl chloride was added dropwise over a 30 minute period. The temperature rose to 0° C. during the addition. The resulting suspension was stirred at temperatures reaching 21° C. over the next 18 hours. The mixture was filtered and the solid was washed with 800 mL of ethyl acetate. The washing was added to the filtrate which was concentrated by approximately 2 L. The residual suspension was diluted with 1 L of ethyl acetate and filtered. The solid was washed with 500 mL of ethyl acetate. The washing was added to the filtrate which was passed through a silica gel (230-400 mesh) pad containing 350 g of adsorbent. The pad was washed with 600 mL of ethyl acetate. The washing was added to the filtrate which was concentrated to approximately 800 mL and diluted with 400 mL of hexane. The suspension was stirred at −10° C. for 2 hours and filtered. The solid was rinsed with ethyl acetate:hexane (2:1, 300 mL) and pressed dry under suction. Further drying in vacuo at 32° C. for 19 hours provided 307 g (89%) of product.

B. Preparation of 2-amino-benzoic acid N'-(2-fluoro-phenyl)-hydrazide

A stirred suspension of 845 g (5.03 mole) of 97% (2-fluoro-phenyl)-hydrazine, hydrochloride in 7.6 L of ethanol at 21-22° C. was added in a stream 563 g (5.57 mole) of triethylamine over a 20 minute period. A whitish gas formed initially. The resulting dark mixture was stirred at 21° C. for 20 minutes and then 854 g (5.03 mole) of 96% 1H-benzo[d][1,3]oxazine-2,4-dione was added. The resulting mixture was heated up to reflux (78° C.) over the next 1 hour. During this period, vigorous gas evolution was noted. Reflux was maintained for 2 hours and then the suspension was stirred at room temperature for 16 hours. The solid was collected by filtration, rinsed once with 150 mL of ethanol, then once with 150 mL of ethanol: ethyl acetate (1:1), and pressed dry under suction. Further drying in vacuo at 35° C. for 7 hours provided 498 g (40%) of product. A second crop of 51 g (4%) of material was obtained from the mother liquor.

C. Preparation of 1-(2-fluoro-phenyl)-1H-indazol-3-ol

A stirred suspension of 105 g (0.429 mole) of 2-amino-benzoic acid N'-(2-fluoro-phenyl)-hydrazide in 1250 mL of ethanol and 1250 mL of 1N hydrochloric acid was heated to 55° C. A solution of 59 g (0.858 mole) of sodium nitrite in 200 mL of water was added dropwise over a 30 minute period. Approximately 10 minutes into the addition a solid began separating. External heating was continued until the reaction temperature reached 65° C. and then it was turned off. The temperature remained at 65-68° C. during the addition and gas evolution became vigorous approximately halfway through the addition. Toward the end of the addition, gas evolution slowed and the temperature dropped below 65° C. External heating was reapplied and the mixture was stirred at 70° C. for 3 hours. The mixture was cooled to −10° C. and filtered. The solid was rinsed once with 50 mL of ethanol, then once with 100 mL of water, and pressed dry under suction. Further drying in vacuo at 35° C. for 7 hours afforded 92 g (94%) of product.

D. Preparation of 4-[1-(2-Fluoro-phenyl)-1H-indazol-3-yloxy]-piperidine-1-carboxylic acid tert-butyl ester To a stirred solution of 173 g (0.76 mole) of 1-(2-fluoro-phenyl)-1H-indazol-3-ol in 1.5 L of N,N-dimethylformamide at room temperature was added 371 g (1.14 mole) of cesium carbonate. The resulting mixture was stirred at room temperature for 2 hours and then 230 g (0.83 mole) of 4-methane-sulfonyloxy-piperidine-1-carboxylic acid tert-butyl ester was added. The resulting mixture was stirred at 85-90° C. for 17 hours, cooled to room temperature, and then concentrated in vacuo by approximately 1 L. The residue was quenched by the dropwise addition of 500 mL of saturated aqueous ammonium chloride. The resulting mixture was stirred at room temperature for 15 minutes and then poured into 2.5 L of stirred ice-water. The resulting mixture was extracted once with 1.5 L dichloromethane and then twice with 0.75 L portions of dichloromethane. Some emulsion formation occurred during these extractions. The combined extracts were dried over magnesium sulfate and concentrated in vacuo to an oil. A vacuum pump was used to remove remaining N,N-dimethylformamide. The residue was taken up in 1.2 L of ether. The mixture was stirred at room temperature for 10 minutes and filtered. The insoluble solid was rinsed with ether and the rinsing added to the filtrate. The solid was dried in vacuo at 30° C. for 6 hours to afford 11.6 g of recovered 1-(2-fluoro-phenyl)-1H-indazol-3-ol. The filtrate was concentrated in vacuo to 268 g (86%) of the product as a viscous, red oil.

E. Preparation of 1-(2-Fluoro-phenyl)-3-(piperidin-4-yloxy)-1H-indazole, hydrochloride To a stirred solution of 187 g (0.456 mole) of 4-[1-(2-fluoro-phenyl)-1H-indazol-3-yloxy]-piperidine-1-carboxylic acid tert-butyl ester in 600 mL of ethyl acetate was added 300 mL of 4M hydrogen chloride in dioxane dropwise over a 30 minute period. The temperature rose to 24° C. from 21° C. during the addition. When the addition was complete, gas evolution was observed and the temperature rose to 28° C. A cold water bath was used to lower the temperature to 18° C. After stirring for approximately 40 min, a solid began separating. Stirring was continued at 18-20° C. for 3 hours and then at −10° C. (ice-acetone bath) for 1 hour. The solid was collected by filtration, rinsed with 60 mL of ethyl acetate and pressed dry under suction. Further drying in vacuo at 30° C. for 16 hours afforded 87.3 g (55%) of product. The combined filtrate and washing was concentrated in vacuo to near dryness. The residue was taken up in 250 mL of ethyl acetate and the suspension was stirred at −10° C. for 2 hours. The solid was collected by filtration, rinsed with 30 mL of ethyl acetate and pressed dry under suction. Further drying in vacuo at 30° C. for 16 hours provided an additional 23.2 g (15%) of product. Total yield=110.5 g (70%). $^1$H NMR (CD$_3$OD) δ ppm: 7.7 (d, 1H), 7.6 (t, 1H), 7.5-7.6 (m, 2H), 7.3-7.5 (m, 2H), 7.25 (m, 1H), 7.2 (t, 1H), 5.2 (m, 1H), 3.4-3.5 (m, 2H), 3.2-3.3 (m, 2H), 2.3-2.4 (m, 2H), 2.2-2.3 (m, 2H).

F. Preparation of 1-(2-Fluoro-phenyl)-3-(piperidin-4-yloxy)-1H-indazole, L-tartrate A mixture of 276 g (0.794 mole of 1-(2-fluoro-phenyl)-3-(piperidin-4-yloxy)-1H-indazole, hydrochloride in 525 mL of tetrahydrofuran and 3.0 L of water was stirred until most (>98%) of the solid dissolved. The solution was filtered from the small amount of insoluble material. To the stirred filtrate was added 135 g (1.28 mole) of sodium carbonate slowly. The resulting mixture was stirred vigorously for 5 minutes and then was extracted twice with 2 L of ether and then once with 1 L of ether. The combined extracts were dried over magnesium sulfate and concentrated in vacuo to dryness. The residual viscous oil (236 g, 96%) was dissolved in 600 mL of tetrahydrofuran. A solution of L-tartaric acid in 2.4 L of water was added to the stirred tetrahydrofuran solution. The resulting solution was concentrated in vacuo to remove the tetrahydrofuran as a solid separated. The resulting suspension was stirred at 5° C. for 1 hour and filtered. The solid was rinsed once with 30 mL of tetrahydrofuran, then once with 100 mL of water, and pressed dry under suction. Further drying in vacuo at 35° C. for 16 hours afforded 234.8 g (67%) of product. A second crop of 35.5 g (10%) was obtained from the mother liquor. Total yield=270.3 g (77%). $^1$H NMR (DMSO) δ ppm: 7.7 (d,1H), 7.6 (t, 1H), 7.4-7.5 (m, 3H), 7.3-7.4 (m, 1H), 7.25 (m, 1H), 7.2 (t, 1H), 5.1 (m, 1H), 3.3 (m, 2H), 3.1 (m, 2H), 2.2 (m, 2H), 2.0 (m, 2H).

Example 113

Synthesis of Salts of 1-(2-fluorophenyl)-3-(piperidin-4yloxy)-1H-indazole

A. 1-(2-fluorophenyl)-3-(piperidin-4-yloxy)-1H-indazole L-tartrate 65.9 mg of L-tartaric acid was added to 136.68 mg of 1-(2-fluorophenyl)-3-(piperidin-4-yloxy)-1H-indazole (clear oil) in 12.45 ml of methanol. The mixture was place under a stream of N$_2$ gas until only approximately 1 ml of solution remained. Precipitation of the salt was observed during this step. Approximately 5 ml of acetone was added and the subsequent solution was then stirred briefly (~2 min). A white solid was recovered using vacuum filtration with a membrane filter. The solid was dried in a vacuum dessicator at ambient temperature (pressure not controlled).

B. 1-(2-fluorophenyl)-3-(piperidin-4-yloxy)-1H-indazole edisylate 3.145 mg of ethanedisulfonic acid was added to 0.56 ml of a solution of 1-(2-fluorophenyl)-3-(piperidin-4-yloxy)-1H-indazole in MeOH (methanol) (concentration=10.3 mg/ml). The solution was heated and stirred in uncapped vials and then placed under a stream of N$_2$ gas. These steps were repeated until approximately 0.100 ml or less of solution remained. Approximately 0.500 ml of MTBE (methyl tert-butyl ether) was then added. Precipitation was observed and the suspension was capped and stirred for 3 hours or less. The vial was then uncapped and allowed to stir for approximately 16 hours. A dry white solid remained.

C. 1-(2-fluorophenyl)-3-(piperidin-4-yloxy)-1H-indazole fumarate 2.162 mg of fumaric acid was added to 0.58 ml of a solution of 1-(2-fluorophenyl)-3-(piperidin-4-yloxy)-1H-indazole in MeOH (concentration=10.3 mg/ml). The solution was heated and stirred in uncapped vials and then placed under a stream of N$_2$ gas. These steps were repeated until approximately 0.100 ml or less of solution remained. Approximately 0.500 ml of MTBE was then added. Precipitation was observed and the suspension was capped and stirred for 3 hours or less. The vial was then uncapped and allowed to stir for approximately 16 hours. A dry white solid remained.

D. 1-(2-fluorophenyl)-3-(piperidin-4-yloxy)-1H-indazole hydrobromide 4.840 mg of concentrated hydrobromic acid was added to 0.89 ml of a solution of 1-(2-fluorophenyl)-3-(piperidin-4-yloxy)-1H-indazole in MeOH (concentration=10.3 mg/ml). The solution was placed under a stream of N$_2$ gas until no solvent remained. Approximately 0.5 ml of MTBE was added and the sample was left open and stirred overnight. A white solid remained upon recovery.

E. 1-(2-fluorophenyl)-3-(piperidin-4-yloxy)-1H-indazole hemi L-tartrate 9.94 mg of L-tartaric acid was added to 4 ml of a solution of 1-(2-fluorophenyl)-3-(piperidin-4-yloxy)-1H-indazole in MeOH (concentration=10.3 mg/ml). The solution was placed under a stream of $N_2$ gas until approximately 0.2 ml of solution was left. Approximately 0.75 ml of IPA (isopropyl alcohol) was then added and solution was returned to aforementioned gas stream for less than 1 minute. Precipitation was observed and the suspension was capped. The suspension was stirred overnight, and the solution had become a gel. Approximately 3 ml of acetone was added and precipitation was observed. A solid was recovered on a membrane filter using vacuum filtration.

F. 1-(2-fluorophenyl)-3-(piperidin-4yloxy)-1H-indazole L-malate 2.383 mg of L-malic acid was added to 0.55 ml of a solution of 1-(2-fluorophenyl)-3-(piperidin-4-yloxy)-1H-indazole in MeOH (concentration=10.3 mg/ml). The solution was heated and stirred in uncapped vials and then placed under a stream of $N_2$ gas. These steps were repeated until approximately 0.100 ml or less of solution remained. Approximately 0.500 ml of MTBE was then added. Precipitation was observed and the suspension was capped and stirred for 3 hours or less. Spheres of gel were observed and no solid was seen. The vial was then uncapped and allowed to stir for approximately 16 hours. A dry white solid remained. Subsequent attempts at repeating this procedure on a larger scale did not generate solid material.

G. 1-(2-fluorophenyl)-3-(piperidin-4yloxy)-1H-indazole phosphate 2.09 mg of concentrated phosphoric acid was added to 0.58 ml of a solution of 1-(2-fluorophenyl)-3-(piperidin-4-yloxy)-1H-indazole in MeOH (concentration=10.3 mg/ml). The solution was heated and stirred in uncapped vials and then placed under a stream of $N_2$ gas. These steps were repeated until approximately 0.100 ml or less of solution remained. Approximately 0.500 ml of MTBE was then added. Precipitation was observed and the suspension was capped and stirred for 3 hours or less. The vial was then uncapped and allowed to stir for approximately 16 hours. A dry white solid remained.

H. 1-(2-fluorophenyl)-3-(piperidin-4-yloxy)-1H-indazole sulfate 1.9 mg of concentrated sulfuric acid was added to 0.58 ml of a solution of 1-(2-fluorophenyl)-3-(piperidin-4-yloxy)-1H-indazole in MeOH (concentration=10.3 mg/ml). The solution was heated and stirred in uncapped vials and then placed under a stream of $N_2$ gas. These steps were repeated until approximately 0.100 ml or less of solution remained. Approximately 0.500 ml of MTBE was then added. Precipitation was observed and the suspension was capped and stirred for 3 hours or less. The vial was then uncapped and allowed to stir for approximately 16 hours. A dry white solid remained.

I.

Citric acid, benzene acid, camphorsulfonic acid, and methane sulfonic acid aliquots were added to equimolar aliquots of 1-(2-fluorophenyl)-3-(piperidin-4-yloxy)-1H-indazole similarly to the aforementioned methods. Solids were not generated using these conditions.

Example 114

Powder X-ray Diffraction (PXRD)

The experimental powder x-ray diffraction spectra of several 1-(2-fluorophenyl)-3-(piperidin-4-yloxy)-1H-indazole salts from Example 114 were determined out utilizing a Bruker D8 X-ray powder diffractometer with GADDS (General Area Diffraction Detector System) C2 system with a single Goebel mirror configuration. The scans were run with the detector at 15.0 cm. Theta 1, or the collimator, was at 7° and Theta 2, or the detector, was at 17°. The scan axis was 2-omega with a width of 3°. At the end of each scan theta 1 is at 10° and theta 2 is at 14°. Samples were run for 60 seconds at 40 kV and 40 mA with CuKα (λ=1.5419 Å) radiation. Scans were integrated from 6.4° to 41° 2 q. The samples were run in ASC-6 sample holders purchased from Gem Dugout (State College, PA). The samples were placed in the cavity in the middle of the sample holder, and flattened with a spatula to be even with the surface of the holder. All analyses were conducted at room temperature (generally 20° C.-30° C.). Scan was evaluated using DiffracPlus software, release 2003, with Eva version 9.0.0.2. The PXRD spectra are reported in FIGS. 1-8: 1-(2-fluorophenyl)-3-(piperidin-4-yloxy)-1H-indazole L-tartrate (FIG. 1); 1-(2-fluorophenyl)-3-(piperidin-4-yloxy)-1H-indazole edisylate (FIG. 2); 1-(2-fluorophenyl)-3-(piperidin-4-yloxy)-1H-indazole fumarate (FIG. 3); 1-(2-fluorophenyl)-3-(piperidin-4-yloxy)-1H-indazole hydrobromide (FIG. 4); 1-(2-fluorophenyl)-3-(piperidin-4-yloxy)-1H-indazole hemi-L-tartrate (FIG. 5); 1-(2-fluorophenyl)-3-(piperidin-4-yloxy)-1H-indazole L-malate (FIG. 6); 1-(2-fluorophenyl)-3-(piperidin-4-yloxy)-1H-indazole phosphate (FIG. 7); and 1-(2-fluorophenyl)-3-(piperidin-4-yloxy)-1H-indazole sulfate (FIG. 8).

Summaries of the angle (2theta) values and intensity values (as a % of the value of the tallest peak) are reported in Tables 1-8 below.

TABLE 1

1-(2-fluorophenyl)-3-(piperidin-4-yloxy)-1H-indazole L-tartrate

| Angle (2theta) | Intensity % |
|---|---|
| 37.8° | 16.7 |
| 33.8° | 17.5 |
| 16.8° | 17.5 |
| 11.9° | 17.6 |
| 13.2° | 18.5 |
| 29.0° | 18.9 |
| 19.5° | 20.9 |
| 27.6° | 21 |
| 31.9° | 21.1 |
| 25.5° | 21.7 |
| 17.9° | 22.2 |
| 23.8° | 22.6 |
| 20.1° | 23.4 |
| 26.0° | 27.6 |
| 23.2° | 28.6 |
| 29.6° | 30 |
| 21.4° | 30.5 |
| 22.0° | 37.3 |
| 20.9° | 49.4 |
| 18.6° | 100 |

TABLE 2

1-(2-fluorophenyl)-3-(piperidin-4-yloxy)-1H-indazole edisylate

| Angle (2theta) | Intensity % |
|---|---|
| 33.0° | 26.8 |
| 15.7° | 27.3 |
| 12.4° | 27.4 |
| 14.1° | 34.1 |
| 28.2° | 35 |
| 30.1° | 39 |
| 17.3° | 46.4 |
| 27.1° | 46.7 |
| 19.0° | 56.2 |
| 25.5° | 57.9 |
| 24.1° | 58.2 |
| 11.6° | 79.5 |
| 22.5° | 94.8 |
| 20.0° | 97.5 |
| 21.2° | 100 |

TABLE 3

1-(2-fluorophenyl)-3-(piperidin-4-yloxy)-1H-indazole fumarate

| Angle (2theta) | Intensity % |
|---|---|
| 12.7° | 22 |
| 31.5° | 24.6 |
| 11.7° | 25.3 |
| 27.8° | 29.6 |
| 22.4° | 31 |
| 26.6° | 31 |
| 20.9° | 35.1 |
| 17.2° | 36.1 |
| 15.9° | 36.3 |
| 29.5° | 45.8 |
| 28.4° | 50.4 |
| 25.3° | 52.2 |
| 18.1° | 67.9 |
| 24.6° | 70.6 |
| 20.1° | 85.8 |
| 23.2° | 100 |

TABLE 4

1-(2-fluorophenyl)-3-(piperidin-4-yloxy)-1H-indazole hydrobromide

| Angle (2theta) | Intensity % |
|---|---|
| 18.0° | 20.5 |
| 21.6° | 20.5 |
| 38.0° | 22.2 |
| 15.4° | 23.8 |
| 14.1° | 25 |
| 30.4° | 25.8 |
| 26.3° | 28.1 |
| 33.5° | 32 |
| 28.0° | 34.9 |
| 25.6° | 37.9 |
| 12.6° | 38.1 |
| 29.3° | 44.3 |
| 20.1° | 57.7 |
| 24.0° | 67.9 |
| 23.8° | 70.3 |
| 16.8° | 71.2 |
| 25.1° | 92.7 |
| 20.9° | 100 |

TABLE 5

1-(2-fluorophenyl)-3-(piperidin-4-yloxy)-1H-indazole hemi-L-tartrate

| Angle (2theta) | Intensity % |
|---|---|
| 10.3° | 24.9 |
| 14.9° | 51.3 |
| 15.7° | 10.2 |
| 17.0° | 23.8 |
| 19.0° | 100 |
| 20.5° | 20.3 |
| 21.6° | 58.9 |
| 22.7° | 20.7 |
| 23.9° | 32.7 |
| 24.7° | 15.7 |
| 25.6° | 14.4 |
| 27.7° | 8.6 |
| 29.8° | 16.7 |
| 32.6° | 9.9 |
| 34.5° | 15.2 |
| 36.2° | 12.5 |
| 39.2° | 8.7 |

TABLE 6

1-(2-fluorophenyl)-3-(piperidin-4-yloxy)-1H-indazole L-malate

| Angle (2theta) | Intensity % |
|---|---|
| 36.8° | 16.9 |
| 24.5° | 17.7 |
| 26.3° | 20.7 |
| 28.7° | 20.8 |
| 12.2° | 21.5 |
| 25.2° | 22.3 |
| 23.1° | 23 |
| 18.2° | 24.5 |
| 30.4° | 25.1 |
| 27.3° | 28.9 |
| 14.7° | 34.7 |
| 20.9° | 34.8 |
| 11.4° | 36.1 |
| 19.2° | 39.9 |
| 16.7° | 50.1 |
| 21.9° | 51.3 |
| 21.5° | 51.5 |
| 20.1° | 100 |

TABLE 7

1-(2-fluorophenyl)-3-(piperidin-4-yloxy)-1H-indazole phosphate

| Angle (2theta) | Intensity % |
|---|---|
| 12.1° | 20.2 |
| 34.7° | 20.3 |
| 14.0° | 20.7 |
| 30.9° | 21 |
| 25.6° | 22.2 |
| 29.3° | 23.5 |
| 33.4° | 28 |
| 16.9° | 32.1 |
| 20.6° | 34.6 |
| 15.6° | 34.9 |
| 26.9° | 43.1 |
| 22.8° | 46.5 |
| 20.0° | 48.1 |
| 27.3° | 49.3 |
| 17.9° | 56.3 |
| 21.2° | 72.5 |
| 24.3° | 74.2 |
| 23.2° | 100 |

TABLE 8

1-(2-fluorophenyl)-3-(piperidin-4-yloxy)-1H-indazole sulfate

| Angle (2theta) | Intensity % |
|---|---|
| 26.7° | 14.8 |
| 27.6° | 16 |
| 17.2° | 19.3 |
| 21.4° | 20.6 |
| 25.4° | 21.5 |
| 29.7° | 24.4 |
| 16.4° | 27.9 |
| 15.0° | 32.6 |
| 20.0° | 35.7 |
| 18.3° | 37.9 |
| 23.0° | 44.1 |
| 24.3° | 44.5 |
| 20.2° | 49.8 |
| 12.1° | 100 |

Example 115

Differential Scanning Calorimetry (DSC)

Differential Scanning Calorimetry (DSC) was carried out on the L-tartrate, edisylate, fumarate, hydrobromide, hemi L-tartrate, L-malate, phosphate, and the sulfate salts of 1-(2-fluorophenyl)-3-(piperidin-4-yloxy)-1H-indazole of Example 113 on a TA Instruments DSC Q1000 V8.1 Build 261 (TA Instruments, New Castle, Del.). Samples were prepared by weighing 2-4 mg of sample into an aluminum pan which was then covered with a pierced aluminum lid (TA Instruments' part nos. 900786.901 (bottoms) and 900779.901 (top)). Data was analyzed using Universal Analysis 2000 for Windows 95/98/2000/NT/Me/XP version 3.8B, Build 3.8.019.

The rate of temperature increase for all experiments was the same for all samples except for the L-tartrate salt. The experiments started at ambient temperature and heated the sample at 20° C./minute under a nitrogen gas purge (flow rate was 50 ml/min). The L-tartrate salt was heated at 10° C./minute.

The edisylate, hydrobromide, hemi L-tartrate, and sulfate salts were heated to 350° C. The fumarate, L-malate, and phosphate salts were heated to 250° C. The L-tartrate salt was heated to 300° C. The melting point onset (° C.) for the salts are reported in Table 9:

TABLE 9

| Name | Melting Peak Onset (° C.) |
|---|---|
| 1-(2-fluorophenyl)-3-(piperidin-4-yloxy)-1H-indazole L-tartrate | 199.98° C. |
| 1-(2-fluorophenyl)-3-(piperidin-4-yloxy)-1H-indazole edisylate | Inconclusive |
| 1-(2-fluorophenyl)-3-(piperidin-4-yloxy)-1H-indazole fumarate | 185.68° C. |
| 1-(2-fluorophenyl)-3-(piperidin-4-yloxy)-1H-indazole hydrobromide | 134.46° C. |
| 1-(2-fluorophenyl)-3-(piperidin-4-yloxy)-1H-indazole hemi L-tartrate | 178.74° C. |
| 1-(2-fluorophenyl)-3-(piperidin-4-yloxy)-1H-indazole L-malate | 145.55° C. |
| 1-(2-fluorophenyl)-3-(piperidin-4-yloxy)-1H-indazole phosphate | 192.97° C. |
| 1-(2-fluorophenyl)-3-(piperidin-4-yloxy)-1H-indazole sulfate | Inconclusive |

Example 116

Single Crystal X-ray Data and Calculated PXRD for 1-(2-fluorophenyl)-3-(piperidin-4-yloxy)-1H-indazole L-tartrate The single crystal structure of 1-(2-fluorophenyl)-3-(piperidin-4-yloxy)-1H-indazole L-tartrate was solved from material synthesized as described above in Example 113. The data were collected at room temperature using an APEX (Bruker-AXS) diffractometer. The structure was solved in the orthorhombic space group $P2_1$ with Z=4 (a=9.585(3)) Å, b=14.978(5)) Å, c=14.952(5)) Å. The structure solution contains two free-form L-tartrate counterion pairs in the asymmetric unit. Hydrogen atoms located on hetero-atoms were found experimentally, the remaining hydrogen atoms were placed in calculated positions. The crystal structure shows that there is one L-tartrate counter ion per 1-(2-fluorophenyl)-3-(piperidin-4-yloxy)-1H-indazole.

The crystal structure (not shown) is consistent with the molecular formula of 1-(2-fluorophenyl)-3-(piperidin-4-yloxy)-1H-indazole L-tartrate. The final model was refined to a goodness fit of 1.009 with $R_1$=0.0481 (I>2sigma(I)) and $wR_2$=0.0863 (I>2sigma(I)). The stereochemistry of 1-(2-fluorophenyl)-3-(piperidin-4-yloxy)-1H-indazole was determined from the known stereochemistry of the L-tartrate counterion. A calculated PXRD pattern was obtained from Material Studios software suite (FIG. 16) using a Reitveld refinement. A summary of the angle (2theta) values and intensity values (as a % of the value of the tallest peak) from the calculated spectrum is reported below in Table 10.

TABLE 10

| Angle (2Theta) | Intensity % |
|---|---|
| 20.1° | 16.0 |
| 21.2° | 16.5 |
| 29.7° | 17.1 |
| 21.4° | 19.2 |
| 17.9° | 20.0 |
| 22.1° | 20.7 |
| 20.7° | 21.1 |
| 23.4° | 21.3 |
| 20.9° | 31.9 |
| 13.2° | 32.7 |
| 11.8° | 66.1 |
| 18.7° | 100.0 |

BIOLOGICAL EXAMPLE 1 hNET Receptor Binding:

Cell pastes of HEK-293 cells transfected with a human norepinephrine transporter cDNA were prepared. The cell pastes were resuspended in 400 to 700 ml of Krebs-HEPES assay buffer (25 mM HEPES, 122 mM NaCl, 3 mM KCl, 1.2 mM $MgSO_4$, 1.3 mM $CaCl_2$, and 11 mM glucose, pH 7.4) with a Polytron homogenizer at setting 7 for 30 seconds. Aliquots of membranes (5 mg/ml protein) were stored in liquid nitrogen until used.

The binding assay was set up in Beckman deep-well polypropylene plates with a total volume of 250 μl containing: test compound ($10^{-5}$M to $10^{-12}$M), cell membranes, and 50 pM [$^{125}$I]-RTI-55 (Perkin Elmer, NEX-272; specific activity 2200 Ci/mmol). The reaction was incubated by gentle agitation for 90 minutes at room temperature and was terminated by filtration through Whatman GF/C filter plates using a Brandel 96-well plate harvester. Scintillation fluid (100 μl) was added to each well, and bound [$^{125}$I]-RTI-55 was determined using a Wallac Trilux Beta Plate Counter. Test compounds were run in duplicate, and specific binding was defined as the difference between binding in the presence and absence of 10 μM desipramine.

Excel and GraphPad Prism software were used for data calculation and analysis. $IC_{50}$ values were converted to $K_i$ values using the Cheng-Prusoff equation. The $K_i$ values (nM) for the hNET are reported below in Table 11.

hSERT Receptor Binding

Cell pastes of HEK-293 cells transfected with a human serotonin transporter cDNA were prepared. The cell pastes were resuspended in 400 to 700 ml of Krebs-HEPES assay buffer (25 mM HEPES, 122 mM NaCl, 3 mM KCl, 1.2 mM $MgSO_4$, 1.3 mM $CaCl_2$, and 11 mM glucose, pH 7.4) with a Polytron homogenizer at Setting 7 for 30 seconds. Aliquots of membranes (~2.5 mg/ml protein) were stored in liquid nitrogen until used.

Assays were set up in FlashPlates pre-coated with 0.1% PEI in a total volume of 250 μl containing: test compound ($10^{-5}$M to $10^{-12}$M), cell membranes, and 50 pM [$^{125}$I]-RTI-55 (Perkin Elmer, NEX-272; specific activity 2200 Ci/mmol). The reaction was incubated and gently agitated for 90 minutes at room temperature, and terminated by removal of assay volume. Plates were covered, and bound [$^{125}$I]-RTI-55 was determined using a Wallac Trilux Beta Plate Counter. Test compounds were run in duplicate, and specific binding was defined as the difference between binding in the presence and absence of 10 μM citalopram.

Excel and GraphPad Prism software were used for data calculation and analysis. $IC_{50}$ values were converted to $K_i$ values using the Cheng-Prusoff equation. The $K_i$ values (nM) for the hSERT are reported below in Table 11:

TABLE 11

| Ex. # | NET $K_i$ | SERT $K_i$ |
|---|---|---|
| 1 | 3.14 | 51.11 |
| 2 | 9.28 | 1622.00 |
| 3 | 3.40 | 831.50 |
| 4 | 3.00 | 270.33 |
| 5 | 84.00 | 1607.00 |
| 6 | 1.65 | 191.50 |
| 7 | 5.30 | 54.72 |
| 8 | 5.19 | 39.03 |
| 9 | 5.63 | 81.57 |
| 10 | 14.30 | 36.09 |
| 11 | 13.96 | 279.00 |
| 12 | 12.50 | 1010.00 |
| 13 | 131.00 | 5289.00 |
| 14 | 13.05 | 100.37 |
| 15 | 329.00 | 1458.50 |
| 16 | 21.50 | 224.00 |
| 17 | 150.50 | 28.00 |
| 18 | 95.50 | 121.00 |
| 19 | 5.43 | 486.00 |
| 20 | 20.17 | 122.32 |
| 21 | 12.50 | 1120.50 |
| 22 | 25.69 | 68.22 |
| 23 | 11.48 | 1526.75 |
| 24 | 9.65 | 5427.33 |
| 25 | 3.20 | 670.50 |
| 26 | 6.90 | 346.00 |
| 27 | 6.34 | 42.29 |
| 28 | 5.10 | 640.00 |
| 29 | 4055.00 | 342.30 |
| 30 | 4.44 | 64.64 |
| 31 | 6.58 | 133.50 |
| 32 | 3.41 | 33.56 |

TABLE 11-continued

| Ex. # | NET $K_i$ | SERT $K_i$ |
|---|---|---|
| 33 | 19.16 | 197.90 |
| 34 | 30.02 | 80.95 |
| 35 | 24.04 | 82.60 |
| 36 | 5.16 | 82.72 |
| 37 | 6.05 | 104.80 |
| 38 | 6.09 | 199.40 |
| 39 | 9.57 | 34.35 |
| 40 | 5.02 | 30.75 |
| 41 | 299.00 | 79.66 |
| 42 | 25.86 | 80.99 |
| 43 | 17.92 | 137.60 |
| 44 | 100.00 | 365.00 |
| 45 | 3.20 | 47.50 |
| 46 | 5.70 | 413.00 |
| 47 | 13.00 | 47.00 |
| 48 | 10.20 | 297.50 |
| 49 | 98.50 | 20.50 |
| 50 | 5.20 | 1141.50 |
| 51 | 11.86 | 53.74 |
| 52 | 35.69 | 45.35 |
| 53 | 54.09 | 145.70 |
| 54 | 274.10 | 28.46 |
| 55 | 71.17 | 125.60 |
| 56 | 6.13 | 9.99 |
| 57 | 18.13 | 52.19 |
| 58 | 55.98 | 133.60 |
| 59 | 69.14 | 32.72 |
| 60 | 221.00 | 76.75 |
| 61 | 20.43 | 21.67 |
| 62 | 495.00 | 313.80 |
| 63 | 39.54 | 19.42 |
| 64 | 512.40 | 271.90 |
| 65 | 4327.00 | 81.22 |
| 66 | 16.93 | 120.50 |
| 67 | 19.72 | 190.50 |
| 68 | 219.50 | 359.30 |
| 69 | 98.03 | 339.40 |
| 70 | 33.58 | 199.50 |
| 71 | 95.50 | 20.51 |
| 72 | 27.38 | 9.76 |
| 73 | 29.34 | 303.80 |
| 74 | 60.50 | 791.70 |
| 75 | 36.39 | 39.77 |
| 76 | 40.36 | 157.80 |
| 77 | 24.81 | 49.55 |
| 78 | 10.16 | 39.92 |
| 79 | 32.81 | 23.72 |
| 80 | 15.04 | 23.88 |
| 81 | 49.80 | 448.70 |
| 82 | 23.23 | 635.40 |
| 83 | 49.26 | 191.40 |
| 84 | 38.13 | 486.80 |
| 85 | 12.50 | 1007.00 |
| 86 | 113.90 | 100.90 |
| 87 | 197.30 | 56.98 |
| 88 | 16.26 | 88.08 |
| 89 | 22.43 | 402.80 |
| 90 | 10.16 | 142.10 |
| 91 | 7.88 | 610.20 |
| 92 | 28.47 | 126.30 |
| 93 | 16.35 | 224.50 |
| 94 | 40.25 | 2848.75 |
| 95 | 5.47 | 3465.67 |
| 96 | 49.53 | 172.30 |
| 97 | 28.51 | 39.52 |
| 98 | 27.33 | 3856.50 |
| 99 | 319.20 | 258.70 |
| 100 | 4.63 | 101.50 |
| 101 | 607.00 | 304.00 |
| 102 | 71.54 | 129.30 |
| 103 | 34.15 | 292.80 |
| 104 | 89.00 | 1579.50 |
| 105 | 294.25 | 4239.75 |
| 106 | | |
| 107 | | |
| 108 | 5.72 | 42.97 |

TABLE 11-continued

| Ex. # | NET $K_i$ | SERT $K_i$ |
|---|---|---|
| 109 | 46.17 | 279.00 |
| 110 | 16.33 | 422.50 |

BIOLOGICAL EXAMPLE 2

Compounds of the present invention may be assayed for their ability to alleviate capsaicin-induced mechanical allodynia in a rat model (e.g., Sluka (2002) *J of Neuroscience*, 22(13): 5687-5693). For example, a rat model of capsaicin-induced mechanical allodynia was carried out as follows:

On day 0, male Sprague-Dawley rats (~150 g) in the dark cycle were placed in suspended wire-bottom cages and allowed to acclimate for 0.5 hour in a darkened, quiet room. The day 0 paw withdrawal threshold (PWT) was determined on the left hind paw by Von Frey hair assessment using the Dixon up and down method. After assessment, the plantar muscle of the right hind paw was injected with 100 µl capsaicin (0.25% (w/v) in 10% ethanol, 10% Tween 80, in sterile saline). On day 6 the PWT of the left hindpaw (contralateral from injection site) was determined for each animal. Animals from the day 6 prereads with PWT≦11.7 g were considered allodynic responders and were regrouped so that each cage had similar mean PWT values.

Subcutaneous Dosing:

On day 7, responders were dosed subcutaneously with 30 mg of the compound of Example 7/kg body weight, 10 mg of the compound of the compound of Example 48/kg body weight, or with vehicle alone. The vehicle was phosphate buffered saline containing 2% Cremophor® EL (BASF).

Example 7 Dosed Animals:

For the animals dosed with the compound of Example 7, the contralateral PWT values were determined at 2 hour after the single dose, with the investigator blinded to the dosing scheme.

For each animal, the day 6 PWT value was subtracted from the 2 hour PWT value for the 10 mg/kg doses to give a delta PWT value that represents the change in PWT due to the 1 hour drug treatment. In addition, the day 6 PWT was subtracted from the day 0 PWT to give the baseline window of allodynia present in each animal. To determine % inhibition of allodynia of each animal normalized for vehicle controls, the following formula was used: % Inhibition of Allodynia=100×[(Delta PWT(drug)−mean Delta PWT(vehicle))/(Baseline−mean Delta PWT(vehicle))].

The mean percent inhibition of allodynia value (for eight animals assayed) is shown in Table 12. Compounds exhibiting a greater than 30% inhbition in allodynia assay are considered active.

Example 48 Dosed Animals:

For the animals dosed with the compound of Example 48, the contralateral PWT values were determined at 1 hour after the single dose, with the investigator blinded to the dosing scheme.

For each animal, the day 6 PWT value was subtracted from the 1 hour PWT value for the 10 mg/kg doses to give a delta PWT value that represents the change in PWT due to the 1 hour drug treatment. In addition, the day 6 PWT was subtracted from the day 0 PWT to give the baseline window of allodynia present in each animal. To determine % inhibition of allodynia of each animal normalized for vehicle controls, the following formula was used: % Inhibition of Allodynia=100×[(Delta PWT(drug)−mean Delta PWT(vehicle))/(Baseline−mean Delta PWT(vehicle))].

The mean percent inhibition of allodynia value (for eight animals assayed) is shown in Table 12 +/− the standard error of the mean (SEM). Compounds exhibiting a greater than 30% inhbition in allodynia assay are considered active.

TABLE 12

| Ex. # | Dose (mg compound/ kg body weight) | % Inhibition of Allodynia +/− SEM |
|---|---|---|
| 7 | 30 mg/kg | 71.5 +/− 4.6 |
| 48 | 10 mg/kg | 74.9% +/− 14.8 |

Oral Dosing:

On day 7, responders were dosed orally with 10 mg compound/kg body weight, or with vehicle alone. The vehicle was in phosphate buffered saline containing 0.5% HPMC (hydroxy-propylmethylcellulose) and 0.2% TWEEN™ 80. The test compounds were formulated in the vehicle for administration. The contralateral PWT values were determined at 2 hours after the single dose, with the investigator blinded to the dosing scheme.

For each animal, the day 6 PWT value was subtracted from the 2 hour PWT value to give a delta PWT value that represents the change in PWT due to the 2 hour drug treatment. In addition, the day 6 PWT was subtracted from the day 0 PWT to give the baseline window of allodynia present in each animal. To determine % inhibition of allodynia of each animal normalized for vehicle controls, the following formula was used: % Inhibition of Allodynia=100×[(Delta PWT(drug)−mean Delta PWT(vehicle))/(Baseline−mean Delta PWT(vehicle))].

The mean percent inhibition of allodynia values (for eight animals assayed for each compound) +/− the standard error of the mean (SEM) are shown in Table 13. Compounds exhibiting a greater than 30% inhbition in allodynia assay are considered active.

TABLE 13

| Ex. # | % inhibition +/− SEM |
|---|---|
| 1 | 67.7 +/− 8.3 |
| 7 | 12.2 +/− 8.3 |
| 8 | 11.5 +/− 9.0 |
| 9 | 34.1 +/− 8.7 |
| 14 | 30.8 +/− 9.7 |
| 20 | 27.5 +/− 10.4 |
| 20 | 41.1 +/− 9.1 |
| 20 | 27.3 +/− 6.3 |
| 27 | 27.0 +/− 3.0 |
| 30 | 68.0 +/− 13 |
| 30 | 67.7 +/− 13.5 |
| 31 | 47.0 +/− 13.0 |
| 31 | 46.7 +/− 13.2 |
| 32 | 60.7 +/− 15.1 |
| 42 | 31.7 +/− 9.9 |
| 43 | 55.4 +/− 16.7 |
| 45 | 46.2 +/− 10.7 |
| 51 | 26.0 +/− 7.0 |
| 56 | 11.0 +/− 10.0 |
| 57 | 26.0 +/− 23.0 |
| 57 | 25.7 +/− 22.8 |
| 100 | 8.7 +/− 9.2 |

It is understood that the examples and embodiments described herein are for illustrative purposes only and that various modifications or changes in light thereof will be suggested to persons skilled in the art and are to be included within the spirit and purview of this application and the scope of the appended claims. All publications, patents, and patent applications cited herein are hereby incorporated by reference in their entirety for all purposes.

What is claimed is:

1. A compound (S)-1-(2,5-difluoro-phenyl)-5-fluoro-3-(morpholin-2-ylmethoxy)-1H-indazole, or a pharmaceutically acceptable salt thereof.

2. A compound as in claim 1, wherein the pharmaceutically acceptable salt of (S)-1-(2,5-difluoro-phenyl)-5-fluoro-3-(morpholin-2-ylmethoxy)-1H-indazole is an acetate, aspartate, benzoate, benzenesulfonate, bicarbonate/carbonate, bisulfate, caprylate, camphor sulfonate, chlorobenzoate, citrate, 1,2-ethane disulfonate, dihydrogenphosphate, dinitrobenzoate, ethane sulfonate, fumarate, gluceptate, gluconate, glucoronate, hibenzate, hydrochloride/chloride, hydrobromide/bromide, hydroiodide/iodide, isobutyrate, monohydrogen phosphate, isethionate, D-lactate, L-lactate, malate, maleate, malonate, mandelate, methanesulfonate, metaphosphate, methylbenzoate, methylsulfate, 2-naphthalene sulfonate, nicotinate, nitrate, orotate, oxalate, palmoate, phenylacetate, phosphate, phthalate, propionate, pyrophosphate, pyrosulfate, saccharate, sebacate, stearate, suberate, succinate sulfate, sulfite, D-tartrate, L-tartrate, toluene sulfonate, xinafoate, arginate, gluconate, or galacturonate salt.

3. A pharmaceutical composition comprising: a therapeutically effective amount of the compound according to claim 2, or the pharmaceutically acceptable salt thereof, and a pharmaceutically acceptable carrier.

4. A pharmaceutical composition comprising: a therapeutically effective amount of the compound according to claim 1, or a pharmaceutically acceptable salt thereof, and a pharmaceutically acceptable carrier.

5. A method of acutely or chronically treating attention deficit hyperactivity disorder comprising administering to a mammal in need of such treatment a therapeutically effective amount of the compound according to claim 1, or a pharmaceutically acceptable salt thereof.

6. A method of acutely or chronically treating a disorder or condition selected from the group consisting of: neuropathic pain, stress urinary incontinence, anxiety, depression, fibromyalgia, pain associated with fibromyalgia, pain associated with oseoarthritis, pain associated with rheumatoid arthritis, bipolar disorder, and schizophrenia comprising administering to a mammal in need of such treatment a therapeutically effective amount of the compound according to claim 1, or a pharmaceutically acceptable salt thereof.

7. A method of claim 5 of acutely or chronically treating attention deficit hyperactivity disorder comprising administering to a mammal in need of such treatment a therapeutically effective amount of a salt of (S)-1-(2,5-difluoro-phenyl)-5-fluoro-3-(morpholin-2-ylmethoxy)-1H-indazole wherein the salt is an acetate, aspartate, benzoate, benzenesulfonate, bicarbonate/carbonate, bisulfate, caprylate, camphor sulfonate, chlorobenzoate, citrate, 1,2-ethane disulfonate, dihydrogenphosphate, dinitrobenzoate, ethane sulfonate, fumarate, gluceptate, gluconate, glucoronate, hibenzate, hydrochloride/chloride, hydrobromide/bromide, hydroiodide/iodide, isobutyrate, monohydrogen phosphate, isethionate, D-lactate, L-lactate, malate, maleate, malonate, mandelate, methanesulfonate, metaphosphate, methylbenzoate, methylsulfate, 2-naphthalene sulfonate, nicotinate, nitrate, orotate, oxalate, palmoate, phenylacetate, phosphate, phthalate, propionate, pyrophosphate, pyrosulfate, saccharate, sebacate, stearate, suberate, succinate sulfate, sulfite, D-tartrate, L-tartrate, toluene sulfonate, xinafoate, arginate, gluconate, or galacturonate salt.

8. A method of claim 6 of acutely or chronically treating a disorder or condition selected from the group consisting of: neuropathic pain, stress urinary incontinence, anxiety, depression, fibromyalgia, pain associated with fibromyalgia, pain associated with osteoarthritis, pain associated with rheumatoid arthritis, bipolar disorder, Alzheimer's disease, and schizophrenia, the method comprising administering to a mammal in need of such treatment a therapeutically effective amount of a salt of (S)-1-(2,5-difluoro-phenyl)-5-fluoro-3-(morpholin-2-ylmethoxy)-1H-indazole wherein the salt is an acetate, aspartate, benzoate, benzenesulfonate, bicarbonate/carbonate, bisulfate, caprylate, camphor sulfonate, chlorobenzoate, citrate, 1,2-ethane disulfonate, dihydrogenphosphate, dinitrobenzoate, ethane sulfonate, fumarate, gluceptate, gluconate, glucoronate, hibenzate, hydrochloride/chloride, hydrobromide/bromide, hydroiodide/iodide, isobutyrate, monohydrogen phosphate, isethionate, D-lactate, L-lactate, malate, maleate, malonate, mandelate, methanesulfonate, metaphosphate, methylbenzoate, methylsulfate, 2-naphthalene sulfonate, nicotinate, nitrate, orotate, oxalate, palmoate, phenylacetate, phosphate, phthalate, propionate, pyrophosphate, pyrosulfate, saccharate, sebacate, stearate, suberate, succinate sulfate, sulfite, D-tartrate, L-tartrate, toluene sulfonate, xinafoate, arginate, gluconate, or galacturonate salt.

9. A compound of claim 1 which is (S)-1-(2,5-difluoro-phenyl)-5-fluoro-3-(morpholin-2-ylmethoxy)-1H-indazole maleic acid salt.

10. A pharmaceutical composition of claim 4 wherein the compound of claim 1 is (S)-1-(2,5-difluoro-phenyl)-5-fluoro-3-(morpholin-2-ylmethoxy)-1H-indazole maleic acid salt.

11. The method according to claim 5, wherein the compound of claim 1 is (S)-1-(2,5-difluoro-phenyl)-5-fluoro-3-(morpholin-2-ylmethoxy)-1H-indazole maleic acid salt.

12. The method according to claim 6, wherein the compound of claim 1 is (S)-1-(2,5-difluoro-phenyl)-5-fluoro-3-(morpholin-2-ylmethoxy)-1H-indazole maleic acid salt.

* * * * *